United States Patent [19]
Milstein et al.

[11] Patent Number: 5,601,846
[45] Date of Patent: Feb. 11, 1997

[54] PROTEINOID MICROSPHERES AND METHODS FOR PREPARATION AND USE THEREOF

[75] Inventors: Sam J. Milstein, Brooklyn; Martin L. Kantor, Mamaroneck, both of N.Y.

[73] Assignee: Emisphere Technologies, Inc., Hawthorne, N.Y.

[21] Appl. No.: 437,698

[22] Filed: May 9, 1995

Related U.S. Application Data

[60] Division of Ser. No. 920,346, Jul. 27, 1992, Pat. No. 5,443,841, which is a continuation-in-part of Ser. No. 898,909, Jun. 15, 1992, abandoned.

[51] Int. Cl.$^6$ .............................. A61K 9/16; A61K 9/26; A61K 9/50; A61K 9/54
[52] U.S. Cl. ..................... 424/499; 424/451; 424/469
[58] Field of Search ..................... 424/451, 499

[56] References Cited

U.S. PATENT DOCUMENTS

| | | |
|---|---|---|
| Re. 24,899 | 11/1960 | Green . |
| 2,671,451 | 3/1954 | Bolger ........................ 128/260 |
| 2,862,918 | 12/1956 | Meyer et al. .................. 260/123.5 |
| 2,868,740 | 1/1959 | Luce ........................... 260/8 |
| 2,971,916 | 2/1961 | Schleicher et al. ............. 252/62.5 |
| 3,016,308 | 1/1962 | Macaulay ...................... 177/37 |
| 3,052,655 | 9/1962 | Fox et al. ..................... 260/78 |
| 3,057,344 | 10/1962 | Abella et al. .................. 128/2 |
| 3,076,790 | 2/1963 | Fox et al. ..................... 260/78 |
| 3,170,802 | 2/1965 | Fukushima ..................... 99/145 |
| 3,190,837 | 6/1965 | Brynko et al. ................. 252/316 |
| 3,474,777 | 10/1969 | Figge et al. ................... 128/2 |
| 3,491,093 | 1/1970 | Pachter et al. ................. 260/247.5 |
| 3,565,559 | 2/1971 | Sato ........................... 424/37 |
| 3,567,650 | 3/1971 | Bakan .......................... 252/316 |
| 3,574,832 | 4/1971 | Engel et al. ................... 424/183 |
| 3,576,758 | 4/1971 | Emrick ......................... 252/316 |
| 3,725,113 | 4/1973 | Chang .......................... 117/82 |

(List continued on next page.)

FOREIGN PATENT DOCUMENTS

| | | | |
|---|---|---|---|
| 1077842 | 8/1976 | Canada ........................ | A61K 9/50 |
| 0000667A1 | 2/1979 | European Pat. Off. ........ | A61K 9/50 |
| 0036145A1 | 9/1981 | European Pat. Off. ........ | A61K 31/62 |
| 0105804 | 4/1984 | European Pat. Off. ........ | C12N 15/00 |
| 0130162A2 | 1/1985 | European Pat. Off. ........ | B01J 13/02 |
| 0170540A1 | 2/1986 | European Pat. Off. ........ | A61K 9/52 |
| 0342056A2 | 11/1989 | European Pat. Off. ........ | A61K 7/06 |
| 0342054A2 | 11/1989 | European Pat. Off. ........ | A61K 7/06 |
| 0365183 | 4/1990 | European Pat. Off. ........ | A61K 31/18 |
| 0366277 | 5/1990 | European Pat. Off. ........ | A61K 9/107 |
| 0448057 | 9/1991 | European Pat. Off. ........ | C12P 21/08 |
| 0452161 | 10/1991 | European Pat. Off. ........ | A61K 7/48 |

(List continued on next page.)

OTHER PUBLICATIONS

Airaudo, C. B. et al. (1987) *Journal of Food Science*, vol. 52(6), pp. 1750–1752.
Andini, S. et al. (1975) *Origins of Life*, vol. 6, pp. 147–153.
Brooke, S. 1 et al. (1977) *BioSystems*, vol. 9, pp. 1–22.
Chen et al. (1975) "Evidence for Hemiacetal Formation", *Biochemistry*, vol. 18, No. 5, pp. 921–925.
Davis et al. (1983) "Leucinal Inhibits . . . ", *Pharmacology Biochemistry Behavior*, vol. 19, pp. 791–794.
Dose, K. (1974) *Origins of Life*, vol. 5, pp. 239–252.
Fasman et al. (1964) *Biochemistry*, vol. 3, No. 11, pp. 1665–1674.

(List continued on next page.)

*Primary Examiner*—Edward J. Webman
*Attorney, Agent, or Firm*—Darby & Darby, P.C.

[57] ABSTRACT

Improved proteinoid microspheres and methods for their preparation and use as oral delivery systems for pharmaceutical agents are described. The proteinoid microspheres are soluble within selected pH ranges within the gastrointestinal tract and display enhanced stability towards least one of photolysis or decomposition over time. The proteinoid microspheres are prepared from proteinoids having between 2 and 8 amino acids and having a molecular weight of about 1000 daltons.

22 Claims, 13 Drawing Sheets

U.S. PATENT DOCUMENTS

| | | | |
|---|---|---|---|
| 3,748,277 | 7/1973 | Wagner | 252/316 |
| 3,794,561 | 2/1974 | Matsukawa et al. | 195/29 R |
| 3,795,739 | 3/1974 | Birkmayer et al. | 424/274 |
| 3,822,348 | 7/1974 | Higashi et al. | 424/95 |
| 3,849,550 | 11/1974 | Teitelbaum | 424/78 |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 424/250 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,402,856 | 9/1983 | Schnoring et al. | 428/402.22 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,919,939 | 4/1990 | Baker | 424/493 |
| 4,925,673 | 5/1990 | Steiner | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,039,481 | 8/1991 | Pacifici et al. | 422/4 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 5/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen et al. | 530/317 |
| 5,244,653 | 9/1993 | Berke et al. | 424/70 |
| 5,250,236 | 10/1993 | Gasco | 264/4.4 |
| 5,271,961 | 12/1993 | Mathiowitz et al. | 427/213.31 |
| 5,278,148 | 1/1994 | Branca et al. | 514/19 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,379 | 2/1995 | Dirix et al. | 424/451 |
| 5,418,010 | 5/1995 | Janda et al. | 427/213.31 |

FOREIGN PATENT DOCUMENTS

| | | | |
|---|---|---|---|
| 0459795 | 12/1991 | European Pat. Off. | A61K 37/02 |
| 0467389 | 1/1992 | European Pat. Off. | A61K 9/52 |
| 0490549A1 | 6/1992 | European Pat. Off. | A61K 47/12 |
| 0517211A1 | 9/1992 | European Pat. Off. | A61K 47/12 |
| 0616799A1 | 9/1994 | European Pat. Off. | A61K 7/00 |
| 1351358 | 3/1964 | France . | |
| 1468601 | 2/1967 | France . | |
| 2133926 | 12/1972 | France | A61K 27/00 |
| 2326934 | 5/1977 | France | A61K 47/00 |
| 2565102 | 12/1985 | France | A61K 9/52 |
| 2424169 | 12/1974 | Germany | A61K 9/00 |
| 3202255 | 10/1982 | Germany | C08L 89/00 |
| 3612102.9 | 10/1986 | Germany | C07K 15/00 |
| 71258/2 | 12/1987 | Israel . | |
| 48-24246 | of 1973 | Japan . | |
| 56-68612 | 6/1981 | Japan | A61K 31/19 |
| 58-35111 | of 1983 | Japan | A61K 9/66 |
| 280826 | 12/1964 | Netherlands . | |
| 280825 | 12/1964 | Netherlands . | |
| B-146698 | 11/1982 | Norway | A61K 37/26 |
| 1236885 | of 0000 | United Kingdom . | |
| 929401 | 6/1963 | United Kingdom . | |
| 1075952 | 8/1967 | United Kingdom . | |
| 1567763 | 5/1980 | United Kingdom | A61K 9/22 |
| WO85/02772 | of 1985 | WIPO | A61K 49/00 |
| WO85/00110 | 1/1985 | WIPO | A61K 47/00 |
| WO85/00105 | 1/1985 | WIPO | A61K 9/52 |
| WO87/04076 | 7/1987 | WIPO | A61K 45/02 |
| WO88/01213 | 2/1988 | WIPO | B23B 5/16 |
| WO92/19263 | 12/1992 | WIPO | A61K 39/00 |
| WO93/18754 | 9/1993 | WIPO | A61K 9/16 |
| WO93/25583 | 12/1993 | WIPO | C07K 15/00 |
| WO94/14420 | 7/1994 | WIPO | A61K 9/16 |
| WO94/21234 | 9/1994 | WIPO | A61K 7/00 |
| WO94/18997 | 9/1994 | WIPO | A61K 37/00 |
| WO94/18950 | 9/1994 | WIPO | A61K 9/127 |
| WO94/24291 | 10/1994 | WIPO | A61K 39/015 |
| WO94/23702 | 10/1994 | WIPO | A61K 9/16 |
| WO94/23767 | 10/1994 | WIPO | A61L 9/16 |
| WO94/28878 | 12/1994 | WIPO | A61K 9/14 |
| WO95/11690 | 5/1995 | WIPO | A61K 37/00 |

OTHER PUBLICATIONS

Fox, S. W. et al. (1976) *BioSystems*, vol. 8, pp. 40–44.

Fox, S. W. et al., *Molecular Evolution and the Origin of Life*, Maxel Decker, New York (1977).

Fox, S. W. et al. (1988) *Biochim. Biophys. Acta,* vol. 160, pp. 246–249.

Fox, S. W. (1976) *Origins of Life,* vol. 7, pp. 49–68.

Fox, S. W. (1980) *Naturwissenschaften,* vol. 67, pp. 378–383.

Fox, S. W. et al. (1960) *Archives of Biochemistry and Biophysics,* vol. 86, pp. 281–285.

Fox, S. W. et al. (1974) *Origins of Life,* vol. 5, pp. 227–237.

Fox, S. W. (1984) *Origins of Life,* vol. 14, pp. 485–488.

Gol'dovskii, A. M. (1978) *Zhurnal Evolyutsionnoi Biokhimii i Fiziologii,* vol. 14(6), pp. 437–439.

Gurrieri, S. et al. (1973) *Thermochimica Acta,* vol. 7, pp. 231–239.

Harada, K. et al. (1979) *BioSystems,* vol. 11, pp. 47–53.

Harada et al., (1960) *Archives of Biochemistry and Biophysics,* vol. 86, pp. 274–280.

Hare (1970) *Etude Cenetique De La Polycondensation Thermique D'χ–Amino Acides,* vol. 45, pp. 330–339.

Heinrich, M. R. et al. (1969) *Archives of Biochemistry and Biophysics,* vol. 130, pp. 441–448.

Heinz, B. et al. (1981) *BioSystems,* vol. 14, pp. 33–40.

Hennon, G. et al. (1975) *Biochimie,* vol. 57, pp. 1395–1396.

Hsu, L. L. et al. (1976) *BioSystems,* vol. 8, pp. 89–101.

Hsu, L. L. et al. (1971) *Currents in Modern Biology,* vol. 4, pp. 12–25.

Ishima, Y. et al. (1981), *BioSystems,* vol. 14, pp. 243–251.

Jackson et al. (1991) "Pharmacological . . . ", *J. Pharm. & Exp. Thera.,* vol. 261, No. 1, pp. 546–552.

Jungck, J. R. et al. (1973) *Naturwissenschaften,* vol. 60, pp. 425–427.

Kokufuta, E. et al. (1984) *BioSystems,* vol. 16, pp. 175–181.

Krampitz, G. et al. (1967) *Naturwissenschaften,* pp. 516–517.

Krampitz, G. et al. (1968) *Naturwissenschaften,* pp. 345 and 346.

Krampitz, G. et al. (1966) *Naturwissenschaften,* pp. 7 and 8.

Lacey, Jr., J. C. et al. (1979) *BioSystems,* vol. 11, pp. 9–17.

Lacey, Jr., J. C. et al. (1979) *BioSystems,* vol. 11, pp. 1–7.

Martinez Luque–Romero, M. et al. (1986) *BioSystems,* vol. 19, pp. 267–272.

Masinovsky, Z. et al. (1989) *BioSystems,* vol. 22, pp. 305–310.

Matsuno, K. (1982) *BioSystems,* vol. 15, pp. 1–11.

Matsuno, K. (1984) *BioSystems,* vol. 17, pp. 11–14.

Matsuno, K. (1981) *BioSystems,* vol. 14, pp. 163–170.

McAlhaney, W. W. et al. (1976) *BioSystems,* vol. 8, pp. 45–50.

Melius, P. et al. (1987) *BioSystems,* vol. 20, pp. 213–217.

Melius, P. et al. (1975) *Bioorganic Chemistry,* vol. 4, pp. 385–391.

Melius, P. (1979) *BioSystems,* vol. 11, pp. 125–132.

Miquel, J. et al. (1971) *Currents in Modern Biology,* vol. 3, pp. 299–306.

Nakashima, T. et al. (1980) *J. Mol. Evol.,* vol. 15, pp. 161–168.

Nakashima, T. et al. (1981) *BioSystems,* vol. 14, pp. 151–161.

Novak, V. J. A. (1984) *Origins of Life,* vol. 14, pp. 513–522.

Olafsson, P. G. et al. (1971) *Polymer Letters,* vol. 9, pp. 521–528.

Phillips, R. D. et al. (1974) *Int. J. Peptide Protein Res.,* vol. 6, pp. 309–319.

Przybylski, A. T. et al. (1982) *Die Naturwissenschaften,* vol. 69, pp. 561–563.

Przybylski, A. T. et al. (1984) *Applied Biochemistry and Biotechnology,* vol. 10, pp. 301–307.

Przybylski, A. T. (1985) *BioSystems,* vol. 17, pp. 281–288.

Rohlfing, D. L. (1975) *Origins of Life,* vol. 6, pp. 203–209.

Rohlfing, D. L. (1970) *Science,* vol. 169, pp. 998–1000.

Rohlfing, D. L. (1967) *Archives of Biochemistry and Biophysics,* vol. 118, pp. 468–474.

Rohlfing, D. L. et al. *Catalytic Activities of Thermal Polyanhydro–αAmino Acids,* pp. 373–418.

Rohlfing, D. L. et al. (1976) *BioSystems,* vol. 8, pp. 139–145.

Ryan, J. W. et al. (1973) *BioSystems,* vol. 5, pp. 115–118.

Saunders, M. A. et al. (1974) *BioSystems,* vol. 6, pp. 81–92.

Snyder, W. D. et al. (1975) *BioSystems,* vol. 7, pp. 222–229.

Sokol, P. E. (1974) *Journal of the American Oil Chemists' Society,* vol. 52, pp. 101–102.

Tschager et al. (1988) *Milchwirtschaftliche Berichte,* vol. 95. pp. 79–83.

Vaughan, G. et al. (1987) *BioSystems,* vol. 20, pp. 219–223.

Vol'kenshtein, M. V. (1989) *Molekulyarnaya Biologiya,* vol. 23(1), pp. 23–37.

Waehneldt, T. V. et al. (1968) *Biochim. Biophys. Acta,* vol. 160, pp. 239–245.

Williams et al. (1991) *J. Biol. Chem.,* vol. 266, No. 8, pp. 5182–5190.

Yuki, A. et al. (1969) *Biochemical and Biophysical Research Communications,* vol. 36(4), pp. 657–663.

Zulaski et al. (1983) "New Carboxyalkyl Inhibitors of Brain Enkenphalinase", *J. Med. Chem.,* 26, pp. 60–65.

(1965) *Chemical Abstracts,* vol. No. 105(1), Abstract No. 12027p.

(1985) *Chemical Abstracts,* vol. No. 102(6), Abstract No. 50870d.

Chemical Abstract, vol. 80(9) Abst. No. 52392a.

Bergeron, Raymond J., et al. (1994) "Macromolecular Self–Assembly of Diketopiperazine Tetrapeptides", *Journal of the American Chemical Society,* vol. 116, pp. 8479–8484.

Bergeron, Raymond J., et al. (1993) "A Comparative Study of the Iron–Clearing Properties of Desferrithiocin Analogues With Desferrioxamine B in a *Cebus* Monkey Model", *Blood,* vol. 81, No. 8, pp. 2166–2173.

Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood,* vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry,* vol. 34, No. 7, pp. 2072–2078.

Bergeron, Raymond et al., "A Comparative Evaluation of Iron Clearance Models", *Annals New York Academy of Sciences,* pp. 278–393.

Andriuoli, G., et al. (1990), *Haemostasis* 20 (suppl. 1):154–158.

Caramazza, I., et al. (1991), *Thrombosis Research* 62:785–789.

Guarini, S., et al. (1983), *Experimentia* 41:350–352.

Guarini, S., et al. (1985), *Pharmacological Research Communications* 17(8):685–697.

Dal Pozzo, A., et al. (1989), *Thrombosis Research* 56:119–124.

Gelb, R., et al (1983), *Lite Sciences* 33(1):83–85.

Watterberg et al. (1988), *Pediatric Research,* vol. 23, No. 4, part 2, p. 570A, column 1, abstract No. 2209.

Bernstein (1985), *Chest* 87(1):68S–73S.

Damge et al. (1988), *Diabetes* 37:246–251.

*Chemical Abstracts*:83 184360k, (1975).

Amino, Y., et al., *Chem. Pharm. Bull.* 36(11):4426–4434 (1988).

Baughman, R. A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".

Haas, S. et al., "Assessment Of Stability Of Proteinoid Microspheres", *Proceed. Intern. Symp. Control Rel. Bioact. Mater.*, 20 (1993), Controlled Release Society, Inc.

X. Ma, et al., *Proceed. Intern. Symp. Control. Rel. Bioact. Mater.*, 20 (1993), Controlled Release Society, Inc. "IN VITRO Mechanistic Investigation of the Proteinoid Microsphere Oral Delivery System".

Yen, H.-R H., et al., "Adsorption of Sulforhodamine 101 on Proteinoid Microspheres" *Proceed. Intern. Symp. Control. Rel. Bioact. Mater.*, 20 (1993), Controlled Release Society, Inc.

Presented at "*IBC Rational Drug Design Conference*", San Diego, Calif.–Dec. 1994.

Bergeron, Raymond J. et al., *J. Am. Chem. Soc.* 1994, 116,8479–8484 "Macromolecular Self–Assembly of Diketopiperazine Tetrapeptides".

Leone–Bay et al., Presented at "*Winter Conference on Medicinal and Bioorganic Chemistry*" Steamboat Springs, Colorado–Feb. 1995 Microsphere Formation and Drug Delivery in a Series of Derivatized Amino Acids.

Santiago et al., *Pharm. Res.* 11: 1994, p. S–298 "Oral Delivery of Heparin Microspheres made with Modified Amino Acids".

Leone–Bay et al., *Pharm. Res.* 11: 1994, p. S–121 "Oral Delivery of Heparin using Acylated Amino Acids".

Sarubbi et al., *Pharm. Res.* 11: 1994, p. S–299 "Oral Calcitonin Delivery using the PODDS Technology".

Leipold et al., *Pharm. Res.* 11: 1994, p. S–298 "Oral Delivery of Interferon in Rats and Primates".

Santiago et al., *Pharm. Res.* 11: 1994, p. S–298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., *Symposia Abstracts.* AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.*, 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., pp. 116–117.

Santiago et al. "Proteinoid Microspheres For The Oral Delivery of Heparin" *Proceed. Intern. Symp. Control Rel. Bioact. Mater.*, 19 (1992), Controlled Release Society, Inc. pp. 514–515.

Santiago et al. *American Society for Microbiology* 92nd General Meeting, Abstract of the General Meeting, p. 159, May 26–30, 1992.

Milstein et al., "Preparation And In Vitro Characterization Of Proteinoid Microspheres" *Proceed Intern. Symp. Control. Rel. Bioact. Mater.*, 19 (1992), Controlled Release Society, Inc. pp. 516–517.

Doris K. Chiappetta, *Eastern Analytical Symposium*, Nov. 17, 1992 "Solutions for Problems in Bioanalysis".

Elizabeth A. Harris. M.S., *Eastern Analytical Symposium*, Nov. 17, 1992 "Solutions for Problems in Bioanalysis".

*AAPS 6TH Ann. Meeting and Expo.*, "Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium – Advances in Gene Technology: Protein Engineering and Beyond*, Jan. 17–22, 1993.

Xinghang Ma, et al. "Stability Study of Drug–loaded Proteinoid Microsphere Formulations during Freeze–drying" *Journal of Drug Targeting*, 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems*, Ctr. for Controlled Chem. Delivery, University of Utah, Feb. 22–25, 1993, pp. 181–182.

Robert O. Dillman, M.D., Annals of Internal Medicine 1989:111 pp. 592–600, "Monoclonal Antibodies for Treating Cancer".

Brendan D. Curti, Critical Reviews in Oncology/Hematology, 1993: 14 pp. 29–39 "Physical barriers to drug delivery in tumors".

V. Hird et al, Genes and Cancer, edited by Desmond Carney & Karol Sikora, pp. 183–189, "Immunotherapy with Monoclonal Antibodies".

Michael E. Osband et al., Immunology Today, vol. 11, No. 6 1990, pp. 93–95, "Problems in the investigational study and clinical use of cancer immunotherapy".

Tibtech Feb. 1993 vol. 11, pp. 42–44 "Therapeutic antibodies – the coming of age".

Thomas A. Waldmann, Articles Jun. 21, 1991, pp. 1657–1662, "Monoclonal Antibodies in Diagnosis and Therapy".

*Chemical Abstracts*, 76(14):72994u, (1971).

*Chemical Abstracts*, 84(7):44660d, (1975).

*Chemical Abstracts*, 86(16):107529g, (1976).

*Chemical Abstracts*, 112(15):134663h, (1989).

*Chemical Abstracts*, 114(22):214519x, (1990).

Abstract, J. Györe et al., Thermal Analysis, vol. 2 – Proceeding Fourth ICTA Budapest 1974, pp. 387–394.

*Chemical Abstracts*, 99(19) 158832b, (1982).

Derwent Abstracts, JP 67008622, (1967).

PURE 9BG5 { 1 = 2 μg
2 = 0.0 μg
3 = 0.25 μg

EMPTY SPHERES { 4 = sup 25 μl
5 = pellet 25 μl mAb SPHERES { 6 = sup 25 μl
7 = pellet 25 μl

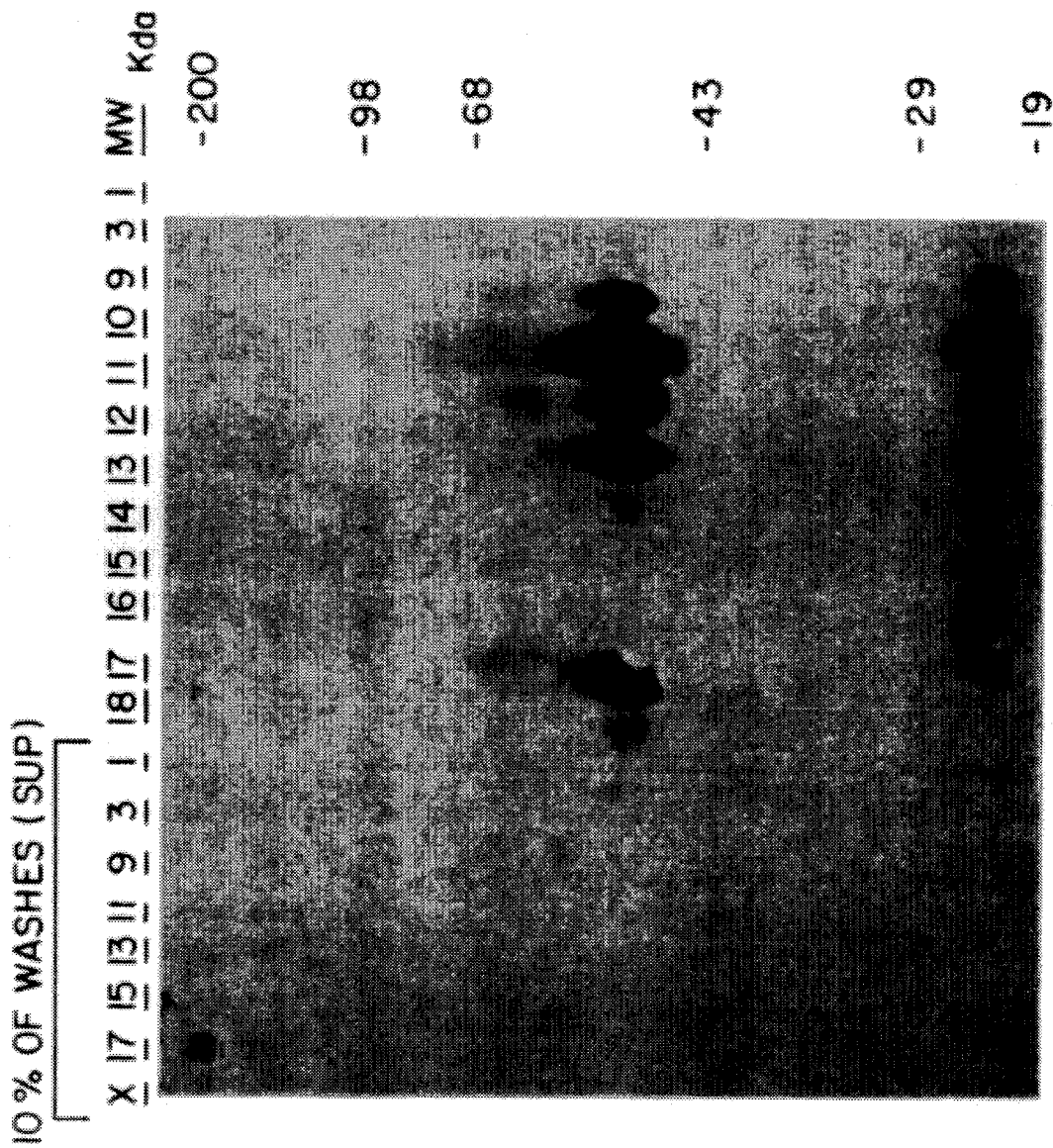

PROTEINOID MICROSPHERES AND METHODS FOR PREPARATION AND USE THEREOF

This is a division of application Ser. No. 07/920,346, filed Jul. 27, 1992 and issued as U.S. Pat. No. 5,443,841 on Aug. 22, 1995; which in turn is a continuation-in-part of Ser. No. 07/898,909, filed Jun. 15, 1992, now abandoned.

FIELD OF THE INVENTION

This invention relates to proteinoids and microspheres made from them. The microspheres releasably encapsulate active agents and have extended longer shelf life and/or photostability. Methods for the preparation of such microspheres are also disclosed.

BACKGROUND OF THE INVENTION

The available modes of delivery of pharmaceutical and therapeutic agents often are severely limited by chemical or physical barriers or both, which are imposed by the body. For example, oral delivery of many such agents would be the route of choice if not for the presence of chemical and physicochemical barriers such as extreme pH in the gut, exposure to powerful digestive enzymes, and impermeability of gastrointestinal membranes to the active ingredient. Among the numerous pharmacological agents which are known to be unsuitable for oral administration are biologically active peptides and proteins, such as insulin. These agents are rapidly destroyed in the gut by acid hydrolysis and/or by proteolytic enzymes.

A great deal of research has been devoted to developing effective oral drug delivery methods and systems for these vulnerable pharmacological agents. The proposed solutions have included:
(a) co-administration of adjuvants (such as resorcinols and non-ionic surfactants polyoxyethylene oleyl ether and n-hexadecyl polyethylene ether to increase the permeability of the intestinal walls; and
(b) co-administration of enzymatic inhibitors, such as pancreatic trypsin inhibitor, diisopropylfluorophosphate (DFF) and trasylol to avoid enzymatic degradation.

The use of such substances, in drug delivery systems, is limited however either because of:
(a) their inherent toxicity when employed at effective amounts;
(b) their failure to protect the active ingredient or promote its absorption;
(c) their adverse interaction with the drug.

Liposomes as drug delivery systems have also been described. They provide a layer of lipid around the encapsulated pharmacological agent. The use of liposomes containing heparin is disclosed in U.S. Pat. No. 4,239,754 and several studies have been directed to the use of liposomes containing insulin; e.g., Patel et al. (1976) *FEBS Letters* Vol. 62, page 60 and Hashimoto et al. (1979) *Endocrinol. Japan*, Vol. 26, page 337. The use of liposomes, however, is still in the development stage and there are continuing problems, including:
(a) poor stability;
(b) inadequate shelf life;
(c) limited to low MW (<30,000) cargoes;
(d) difficulty in manufacturing;
(e) adverse interactions with cargoes.

More recently, artificial amino acid polymers or proteinoids, forming microspheres, have been described for encapsulating pharmaceuticals. For example, U.S. Pat. No. 4,925,673 (the '673 patent), the disclosure which is hereby incorporated by reference in its entirety, describes such microsphere constructs as well as methods for their preparation and use. The '673 patent also describes microspheres which encapsutate pharmaceutical agents for delivery into the gastrointestinal tract or into the blood.

While the proteinoid microspheres described in the '673 patent are useful for their intended purposes, the physicochemical properties of the proteinoid microspheres, such as light sensitivity, shelf life and the selectivity of their solubility in various portions of the gastrointestinal tract, could be improved. Additionally, there is a need in the art for microspheres that can encapsulate a broader range of active agents such as lipophilic drugs.

The method employed in the '673 patent to prepare proteinoids produces a complex mixture of high molecular weight (MW) (>1000 daltons) and low MW ($\leq$1000 daltons) peptide-like polymers which are difficult to separate. Moreover, the method produces a small amount of the low MW proteinoids which is the microsphere-forming fraction. Hence, an improved method of preparing of the proteinoids is also desired.

Accordingly, there is a need in the art for improved proteinoid microspheres as well as improved methods for their preparation.

OBJECTS OF THE INVENTION

It is an object of this invention to provide a proteinoid which forms microspheres as a delivery system with enhanced stability towards at least one of photodegradation and decomposition over time.

It is another object of the invention to provide a proteinoid that forms microspheres with more selective solubility under various conditions such as pH.

It is yet another object of the invention to provide proteinoid microspheres encapsulating biologically active agents which are selectively releasable within particular portions of the gastrointestinal tract.

It is a further object of the invention to provide proteinoid microspheres which promote the bioavailability of pharmaceutical agents which otherwise display poor absorption in the gastrointestinal tract.

It is yet a further object of the invention to provide an improved method for producing proteinoid microspheres having particular characteristics and for improving yield of the desired microspheres.

It has been found that these objects and other advantages, which will be apparent from this specification, are achieved by the invention described below.

SUMMARY OF THE INVENTION

The present invention relates to improved proteinoid microspheres and methods of making and use thereof.

Proteinoids of a MW of about 1000 daltons and of defined amino acids are useful in preparing proteinoid microspheres with improved stability against photodegradation and/or decomposition. The proteinoids comprise a peptide polymer selected from the group consisting of:
(i) peptide polymers made from at least one first monomer selected from the group consisting of tyrosine and phenylalanine; and from at least one second monomer selected from the group consisting of glutamic acid, pyroglutamic acid, glutamine, and aspartic acid;

(ii) peptide polymers made from at least one first monomer selected from the group consisting of tyrosine and phenylalanine; and from at least one second monomer selected from the group consisting of glutamic acid, pyroglutamic acid, glutamine, and aspartic acid; and from at least one third monomer selected from the group consisting of lysine, arginine and ornithine, the proteinoid being a microsphere-forming proteinoid and being soluble within a selected pH range.

The proteinoid molecules of the invention contain between about 2 and about 20 amino acid residues, preferably between about 2 and about 8 amino acid residues, and have a molecular weight which ranges between about 500 and about 1500 daltons, preferably about 1000 daltons.

The microspheres are useful as delivery systems to releasably encapsulate and carry a broad range of cargoes including pharmaceutical agents, dye reagents and cosmetic ingredients. In particular, the microspheres are useful as oral delivery systems of sensitive pharmaceutical agents, which normally would not be administrable via the oral route, for selective release at targeted regions of the gastrointestinal tract.

DESCRIPTION OF THE DRAWINGS

FIG. 7 is a photograph of an x-ray film of a western immunoblot analysis of samples described in Example 10.

DETAILED DESCRIPTION OF THE INVENTION

Figure 1:
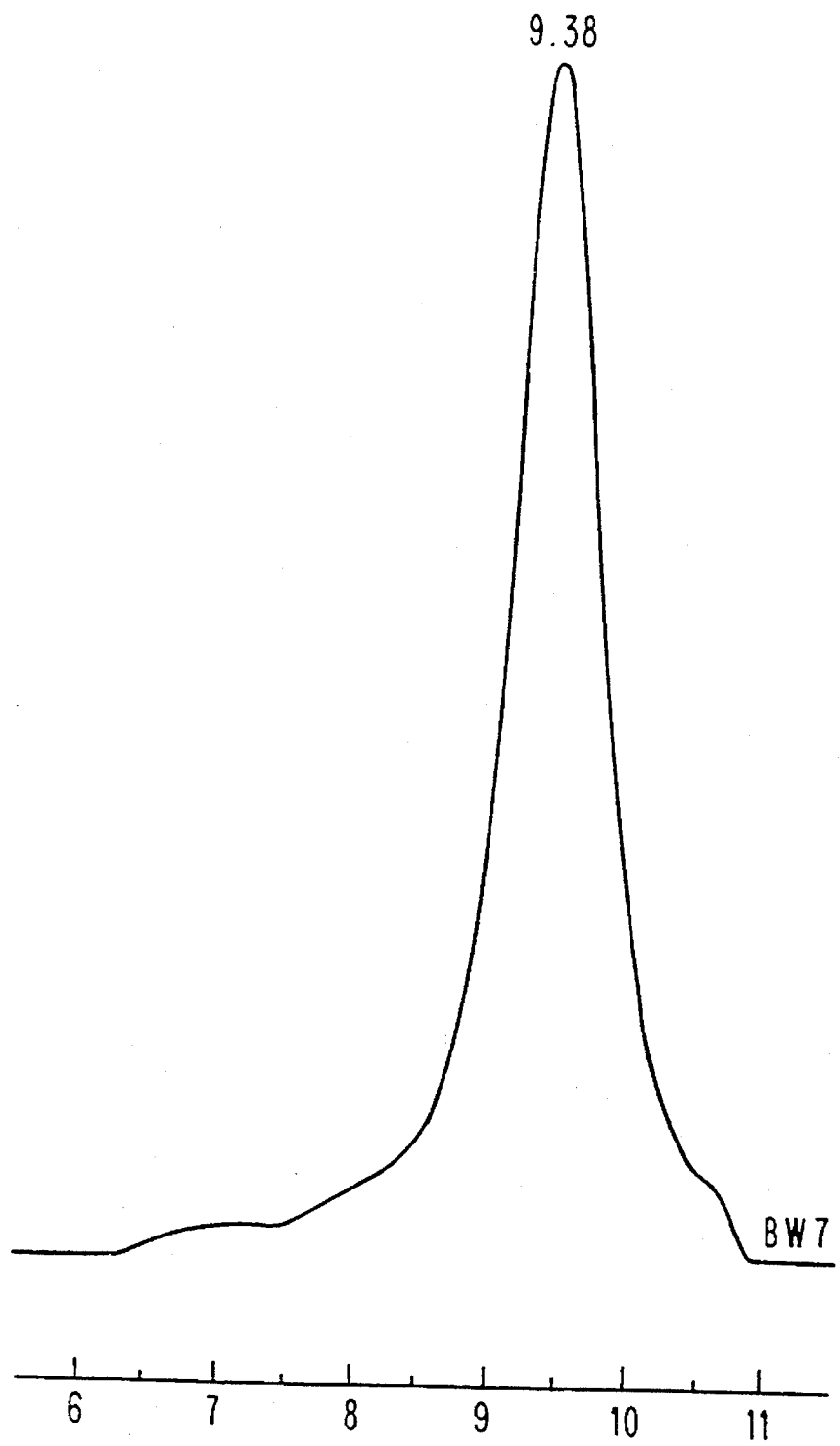
FIG. 1 illustrates the molecular weight distribution as a function of monomer concentration of poly (Asp.Bz-co-Phe) polymer prepared by the NCA method as described in Example 3.

All patents and literature references cited in this specification are hereby incorporated by reference in their entirety. In case of inconsistencies, the present description, including the definitions and interpretations, will prevail.

The instant invention arose from the discovery that proteinoids of a MW of about 1000 daltons and of defined amino acid composition can be obtained by modifying known reactions and selecting starting materials. These proteinoids form microspheres with surprisingly enhanced stability against at least one of photodegradation and decomposition over time. In addition, microspheres prepared from such proteinoids carry a broader range of pharmaceutical agents, including lipophilic drugs such as alpha-interferon, calcitonin, and M-protein, and display a selective releasability within various portions of the gastrointestinal tract, relative to prior art proteinoid microspheres.

The proteinoids of the invention comprise a peptide polymer selected from the group consisting of:

(i) peptide polymers made from at least one first monomer selected from the group consisting of tyrosine and phenylalanine; and from at least one second monomer selected from the group consisting of glutamic acid, pyroglutamic acid, glutamine, and aspartic acid;

(ii) peptide polymers made from at least one first monomer selected from the group consisting of tyrosine and phenylalanine; at least one second monomer selected from the group consisting of glutamic acid, pyroglutamic acid, glutamine, and aspartic acid; and from at least one third monomer selected from the group consisting of lysine, arginine and ornithine, the proteinoid being a microsphere-forming proteinoid and being soluble within a selected pH range.

The proteinoid molecules of the invention contain between about 2 and about 20 amino acid residues, preferably between about 2 and about 8 amino acid residues, and have a molecular weight which ranges between about 500 and about 1500 daltons, preferably about 1000 daltons.

Microspheres prepared from the proteinoid molecules, in accordance with the present invention, display a selective solubility at specific acidic or basic pH ranges, depending on the choice and amount of the second and third monomers in the proteinoid.

Proteinoid microspheres which are selectively soluble under alkaline pH environments, such as those found in the distal portion of the intestine, are prepared from base-soluble proteinoids. These proteinoids contain at least one second monomer selected from the group consisting of glutamic acid, glutamine, pyroglutamic acid, and aspartic acid such that an excess of acidic (carboxyl) residues is present in the resultant proteinoid. At a pH ranging between about 7.2 and about 11.0, the base-soluble proteinoid exists largely as the anion and is soluble. At a pH below about 7.0, the proteinoid is largely protonated and insoluble in water.

Similarly, proteinoid microspheres which are selectively soluble under acidic pH environments, such as the stomach, are prepared from acid-soluble proteinoids. In this case, the proteinoid contains at least one second monomer selected from the group consisting of glutamic acid, pyroglutamic acid, glutamine, and aspartic acid and at least one third monomer selected from the group consisting of lysine, arginine, and ornithine, such that an excess of basic (amino) residues is present in the resultant proteinoid. At a pH ranging between about 1 and about 7, the base-soluble proteinoid exists largely as the cation and is soluble. At a pH above about 7.2, the proteinoid is largely unprotonated and insoluble in water.

The pH and the solubility characteristics of the acid-soluble proteinoid depends largely, but not exclusively, upon the pH and solubilty of the last amino acid (the "capping" amino acid) present in the proteinoid. For instance, the incorporation of a basic amino acid, e.g. a third monomer, selected from the group consisting of lysine, arginine and ornithine in the acid-soluble proteinoid will result in the elevation of the pkI (pH at the isoelectric point) of the proteinoid.

The proteinoids of the present invention are preparable by a thermal condensation reaction by heating mixtures of the appropriate amino acids under conditions described in the '673 patent. In contrast with the '673 patent procedures which use as many as eighteen amino acids, mixtures of two to five specific amino acids with at least one selected from each group yield proteinoids which form microspheres with selective solubility at particular pH ranges and at high yields.

In carrying out the thermal condensation reaction, it has now been discovered that inclusion of tetramethylene sulfone, an inert, high boiling, polar solvent, maximizes the yield (>80%) of low MW proteinoids. Omission of solvent or use of other solvents such as high-boiling alcohols (e.g. glycerol), acids (e.g. phosphoric acid), ketones, and ethers, or non-polar solvents such as substituted aromatic compounds or aliphatics like mineral oil does not produce high yields of low MW proteinoids. Presumably this is due to the poor solubility of the amino acid monomers in these solvents and/or unavoidable side reactions between the monomers and the solvent under the reaction conditions.

In general, individual amino acids are added to a reaction flask containing tetramethylene sulfone which has been heated to a temperature ranging between about 130° C. and about 200° C., preferably about 175° C. to 195° C., under an inert atmosphere of argon or nitrogen gas. After each addition, the solution is stirred for a period of time ranging between about 10 minutes and about 5 hours, depending on the amino acid type and the order of addition.

Upon heating mixtures of amino acids to temperatures of about 190° C. as described above, a reaction takes place and water, ammonia and carbon dioxide are produced as side-products. Water is removed from the reaction as formed and the reaction is terminated when water formation ceases. Thereafter, the proteinoid are precipitated out of the reaction solution by quenching with excess water, under vigorous stirring. After stirring for a period of about 1 hour, the proteinoids are collected by filtration, washed with water and dried under vacuum.

Chemical condensation methods which utilize derivatized amino acids are also useful for making the proteinoids of the present invention as they permit greater control of molecular weight. Such reactions are generally conducted at lower reaction temperature and with initiators. In particular, low MW proteinoids produced by the alpha-amino acid N-carboxyanhydride (NCA) method and the diphenylphosphoryl azide (DPPA) method (N. Nishi et al. (1991) *Makromol. Chem.*, vol. 192, pages 1789–1798) were found to form protein microspheres having selected solubility within a particular pH range.

The NCA method involves the preparation of N-carboxyanhydrides of alpha-amino acid esters and their subsequent polymerization, using low MW amines as initiators. It has been discovered that non-NCA derived amino esters, e.g. α-methyl tyrosine ester, are effective initiators which are stable and soluble in many organic solvents such as tetrahydrofuran (THF). The use of amino acids as initiators, presumably due to their poor solubility in organic solvents and their low stability, are not known. The NCA reaction produces a high yield of proteinoids with high purity.

The DPPA method involves the direct condensation of benzyl esters of alpha-amino acids in the presence of DPPA and a low MW amine, followed by removal of the protective benzyl groups, contained in the proteinoid product, by alkaline hydrolysis. If catalytic hydrogenation is used in place of alkaline hydrolysis, low MW proteinoids of unexpected high purities and yields are obtained.

Proteinoids prepared by any of the above methods can be used immediately to microencapsulate an active pharmacological agent or the proteinoid can be concentrated or dried by conventional means and stored for future use.

The proteinoids of the invention are purified as follows: crude proteinoids are slurried with water and heated to about 70° C. While at this temperature, the pH of the slurry is adjusted to about pH 8 using an aqueous 40% (W/V) sodium hydroxide solution for a acid-soluble proteinoid or acidic pH using an aqueous acidic solution for a base-soluble proteinoid. The mixture is then filtered and the filter cake washed with a volume of water. The washes and filtrate are then combined and evaporated to dryness in vacuo to afford proteinoids. If necessary, this process can be repeated until proteinoids of a desired purity level are obtained.

Alternatively, the proteinoid may be purified by fractionating on a column containing solid supports which include silica gel or alumina, using methanol or propanol as mobile phase; ion exchange resin using water as the mobile phase; reverse phase column supports using trifluoroacetic acid/acetonitrile mixtures as mobile phase. The proteinoids may also be purified by extraction with a lower alcohol such as propanol or butanol to remove low molecular weight contaminants.

Proteinoid microspheres are made from purified proteinoids as follows: proteinoids are dissolved in deionized water at a concentration ranging between about 75 and about 200 mg/ml, preferably about 100 mg/ml at a temperature between about 25° C. and about 60° C., preferably about 40° C. Particulates remaining in the solution may be filtered out by conventional means such as gravity filtration over filter paper.

Thereafter, the proteinoid solution, maintained at a temperature of about 40° C., is mixed with an aqueous acid solution (also at about 40° C.) having an acid concentration ranging between about 1N and about 2N, preferably about 1.7N. The resulting mixture is further incubated at 40° C. for a period of time effective for microsphere formation as observed by light microscopy. In practicing this invention, the preferred order of addition is adding the proteinoid solution to the aqueous acid solution.

Suitable acids include any acid which does not (a) adversely effect the proteinoid, e.g. chemical decomposition; (b) interfere with microsphere formation; (c) interfere with microsphere encapsulation of cargo; and (d) adversely interact with the cargo. Preferred acids for use in this invention include acetic acid, citric acid, hydrochloric acid, phosphoric acid, malic acid and maleic acid.

In practicing the invention, a microsphere stabilizing additive preferably incorporated into the aqueous acid solution or into the proteinoid solution, prior to the microsphere formation process. The presence of such additives promotes the stability and dispersibility of the microspheres in solution.

The additives may be employed at a concentration ranging between about 0.1 and 5% (W/V), preferably about 0.5% (W/V). Suitable, but non-limiting, examples of microsphere stabilizing additives include gum acacia, gelatin, polyethylene glycol, and polylysine.

It has been found the presence of citric acid in the encapsulated microspheres interferes with a subsequent lyophilization process. Hence, microsphere encapsulates prepared with citric acid solutions are preferably dialyzed against 5% acetic acid solution for at least two hours with at least four changes of the dialysis solution to remove citric acid by an exchange process.

Thereafter, the microspheres are frozen (e.g., over liquid nitrogen or dry ice), lyophilized, and stored under desiccant at room temperature or below.

Under these conditions, the proteinoid molecules form hollow microspheres of less than 10 micron diameter (microspheres). If the proteinoid microspheres are formed in the presence of a soluble material, e.g. a pharmaceutical agent in the aforementioned aqueous acid solution, this material will be encapsulated in the hollows of the microspheres and confined within the proteinoid wall defined by the spherical structure. In this way, one can encapsulate pharmacologically active materials such as peptides, proteins, and polysaccharides as well as charged organic molecules, e.g. quinolones or antimicrobial agents, having poor bioavailability by the oral route. The amount of pharmaceutical agent which may be encapsulated by the microsphere is dependent on a number of factors which include the concentration of agent in the encapsulating solution.

The proteinoid microspheres of the invention are pharmacologically harmless and do not alter the physiological and biological properties of the active agent. Furthermore, the encapsulation process does not alter the pharmacological properties of the active agent. While any pharmacological agent can be encapsulated within proteinoid microspheres, it is particularly valuable for delivering agents which otherwise would be destroyed or rendered less effective by conditions encountered in the animal body before it reaches its target zone and which are poorly absorbed in the gastrointestinal tract.

The proteinoid microspheres of the invention are particularly useful for the oral administration of certain pharmacological agents, e.g. small peptide hormones, which, by themselves, pass slowly or not at all through the gastrointestinal mucosa and/or are susceptible to chemical cleavage by acids and enzymes in the gastrointestinal tract. Non-limiting examples of such agents include human or bovine growth hormone, interferon and interleukin-II, calcitonin, atrial natriuretic factor, antigens and monoclonal antibodies.

The choice of a particular proteinoid for use in encapsulating a pharmacological agent depends on a number of factors which include:
(1) the acidity or basicity of the agent;
(2) the targeted area for release in the gastrointestinal tract;
(3) the solubility of the drug at certain pH ranges;
(4) efficiency of encapsulation;
(5) interaction of drug with proteinoid.

For example, proteinoids made from glutamic acid, aspartic acid, tyrosine, and phenylalanine are especially suitable for encapsulating polysaccharides like heparin.

In addition to selective pH solubility, the particle size of the microsphere plays an important role in determining release of the active agent in the targeted area of the gastrointestinal tract. Microspheres having diameters between about $\leq 0.1$ microns and about 10 microns, preferably between about 5.0 microns and about 0.1 microns, and encapsulating active agents are sufficiently small to effectively release the active agent at the targeted area within the gastrointestinal tract. Large proteinoid microspheres (>10 microns) tend to be less effective as oral delivery systems.

The size of the microspheres formed by contacting proteinoids with water or aqueous solution containing active agents can be controlled by manipulating a variety of physical or chemical parameters, such as the pH, osmolarity or salt content of the encapsulating solution, and the choice of acid used in the encapsulating process.

By tailoring both the solubility characteristics of a proteinoid and the particle size of the microspheres, active agent bearing microspheres can be produced from base-soluble proteinoids which are stable in the highly acidic stomach (normal pH of from about 2 to about 6), but which dissolve in the distal portion of the intestines. Such systems are suitable for oral administration of peptide hormones, e.g. insulin, and polysaccharides, e.g. heparin, which otherwise would be quickly destroyed in the stomach. They also are suitable for protecting the stomach from gastric irritants, such as aspirin. When such aspirin containing microspheres are orally administered, they pass through the gastrointestinal mucosa and release the aspirin far more rapidly than conventional enterically coated aspirin, which first must traverse the stomach and then must enter the bloodstream from the intestine after the enteric coating has dissolved.

It also is possible to produce systems from acid-soluble proteinoids which are stable under weakly basic conditions (pH of about 8), but which release active agent under acidic conditions (pH of about 2 to 5). Such systems are suitable for the intravenous administration of pharmacological agents such as calcium regulators and redox carrier systems for dopamine or gamma-aminobutyric acid.

The microspheres of the invention may be orally administered alone as solids in the form of tablets, pellets, capsules, and granulates suitable for suspension in liquids such as water or edible oils. Similarly, the microspheres can be formulated into an orally administrable composition containing one or more physiologically compatible carriers or excipients. These compositions may contain conventional ingredients such as gelatin, polyvinylpyrrolidone and fillers such as search and methyl cellulose.

EXAMPLE 1

Preparation of a Base-soluble Proteinoid by a Thermal condensation Reaction 750 ml of tetramethylene sulfone was heated to 190° C. in an inert nitrogen atmosphere in a 4 liter flask with stirring. 294 g of glutamic acid was added and the mixture was heated for one-half hour. 266 g of aspartic acid was added and the mixture heated as rapidly as possible to 190° C. and held there for 15 minutes. 362 g of tyrosine was added and the mixture heated at 190° C. for 3 hours. 330 g of phenylalanine was added and the mixture heated at 190° C. for 1.5 hours. The hot melt was then poured into 5 liters of water with vigorous stirring. After stirring for about 1 hour, the mixture was filtered and the filtrate discarded. The cake was reslurried in 5 liters of water, filtered and the cake was again reslurried in 5 liters of water. The slurry was warmed to about 70° C. and, while at this temperature, the pH was adjusted to 8 using 40% sodium hydroxide solution. The mixture was filtered and the cake washed with a small amount of water. The washes and filtrate are combined and evaporated to dryness in vacuo to give proteinoid.

Appendices A, B, and C describe examples of other proteinoids prepared by the thermocondensation method.

EXAMPLE 2

Preparation of an Acid-soluble Proteinoid by a Thermal Condensation Reaction 750 ml of tetramethylene sulfone is heated to 190° C. in an inert nitrogen atmosphere in a 4 liter flask with stirring. 294 g of glutamic acid is added and the mixture is heated for one-half hour. 362 g of tyrosine is added and the mixture is heated at 190° C. for 3 hours. 330 g of phenylalanine is added and the mixture is heated at 190° C. for 1.5 hours. 266 g of arginine is added and the mixture is heated for an additional 1.5 hours. The hot melt is then poured into 5 liters of water with vigorous stirring. After stirring for about 1 hour, the mixture is filtered and the filtrate is discarded. The cake is reslurried in 5 liters of water, filtered and the cake is again reslurried in 5 liters of water. The slurry is warmed to about 70° C. and, while at this temperature, the pH was adjusted to 5 using 10% acetic acid solution. The mixture is filtered and the cake is washed with a small amount of water. The washes and filtrate are combined and evaporated to dryness in vacuo to give proteinoid.

Appendices A, B, and C describe examples of other proteinoids prepared by the thermocondensation method.

EXAMPLE 3

Preparation of Proteinoids by the NCA Method Using Amine Initiator

This example illustrates the NCA method for preparing copolypeptides consisting of Asp.Bz, Glu.Bz, Phe, and Tyr components. The NCA monomers of these amino acids were prepared according to the reported method.

The reactions were carried out in tetrahydrofuran (THF) or in dichloromethane using benzylamine ($BzNH_2$) or 4-methylbenzyl amine ($MeBzNH_2$) as initiator at room temperature ([M]=10%). The characterization of the resulting copolymers was performed by $^1H$ NMR and GPC. The results obtained are listed in Table 1.

As shown in Table 1, proteinoids having Asp and/or Glu as the second monomers and Phe and/or Tyr as the first monomers were obtained in high yield from the polymerization initiated with $BzNH_2$ at the ratio of [M]/[I]=5 (No. 2-1 to 2-7).

The GPC curve (FIG. 1) for poly(Asp.Bz-co-Phe), from which a polydispersity of 1.91 was determined. Similar molecular weight distributions were observed for other copolymers.

Polydispersity is defined herein as the molecular weight distribution of a sample. The distribution is assigned a numerical value derived from the molecular weight (MW) divided by the molecular number (Mn). The polydispersity value for a homopolymer is 1 because the molecular weight is equal to the molecular number. Any polymer with a polydispersity value of 1 is considered to have a very narrow distribution. A polymer with polydispersity value of 1.6 to 1.7 is considered to have medium distribution. A polymer with a polydispersity value of 2.0–2.1 is considered to have a broad distribution.

The homopolymerization of the NCA of Asp.Bz and the copolymerizations of the NCAs of Asp.Bz, Glu.Bz, Phe, and Tyr were also carried out using $MeBzNH_2$ as initiator (No. 2-11, 2-15, and 2-16). Similar results were obtained for reactions initiated by $BzNH_2$.

TABLE 1

COPOLYMERIZATION OF NCAs INITIATED WITH AMINES STORED AT ROOM TEMPERATURE FOR 4 DAYS

| POLYM. NO. | COMONOMER COMPOSITION | INITIATOR ([M]/[I]) | SOLVENT | YIELD (%) | $M_w$ |
|---|---|---|---|---|---|
| 2-1 | Asp—Glu—Phe—Tyr (1:1:1:1) | $BzNH_2$ (5:1) | THF | 84.1 | 830 |
| 2-2 | Asp—Phe (1:1) | $BzNH_2$ (5:1) | THF | 70.9 | 730 |
| 2-3 | Asp—Tyr (1:1) | $BzNH_2$ (5:1) | THF | 88.6 | 1000 |
| 2-4 | Asp—Tyr (2:1) | $BzNH_2$ (5:1) | THF | 89.3 | 1050 |
| 2-5 | Glu—Tyr (1:1) | $BzNH_2$ (5:1) | THF | 84.9 | |
| 2-6 | Glu—Phe—Tyr (2:1:1) | $BzNH_2$ (5:1) | $CH_2Cl_2$ | 68.8 | 790 |
| 2-7 | Glu—Phe—Tyr (1:1:1) | $BzNH_2$ (5:1) | $CH_2Cl_2$ | 53.7 | 1000 |
| 2-11 | Asp | $MeBzNH_2$ (5:1) | THF | 88.3 | 870 |
| 2-15 | Asp—Glu—Phe—Tyr | $MeBzNH_2$ (5:1) | THF | 76.4 | — |

TABLE 1-continued

COPOLYMERIZATION OF NCAs INITIATED WITH AMINES STORED AT ROOM TEMPERATURE FOR 4 DAYS

| POLYM. NO. | COMONOMER COMPOSITION | INITIATOR ([M]/[I]) | SOLVENT | YIELD (%) | $M_W$ |
|---|---|---|---|---|---|
| 2-16 | (1:1:1:1) Asp—Glu—Phe—Tyr (1:1:1:1) | MeBzNH$_2$ (5:1) | THF | 76.4 | 630 |

EXAMPLE 4

Preparation of Proteinoids by the NCA Method Using α-Methyl Tyrosine Ester as Initiator This example illustrates the method of conducting NCA polymerizations, using α-methyl tyrosine ester (Tyr.Me) as the initiator. The reaction conditions are essentially the same as described in Example 3 except tetrahydrofuan (THF) solvent was used. The results are listed in Table 2.

TABLE 2

PROTEINOID SYNTHESIS BY NCA INITIATED WITH AMINO ACIDS STORED AT ROOM TEMPERATURE FOR 4 DAYS

| POLYM. NO. | COMONOMER COMPOSITION | INITIATOR ([M]/[I]) | SOLVENT | YIELD (%) | $M_W$ |
|---|---|---|---|---|---|
| 2-8 | Asp—Glu—Phe (1:1:1) | Tyr.Me (1:1) | CH$_2$Cl$_2$ | 100 | 450 |
| 2-9 | Asp—Glu—Phe (1:1:1) | Tyr.Me (3:1) | CH$_2$Cl$_2$ | 71.4 | 450 |
| 2-10 | Asp—Glu—Phe (1:1:1) | Tyr.Me (5:1) | CH$_2$Cl$_2$ | 68.0 | 730 |
| 2-12 | Asp | Tyr.Me (1:1) | THF | 100 | 460 |
| 2-13 | Glu—Tyr (1:1) | β-Ala (2:1) Suc.An (2:1) | THF (reflux) | 67.4 | 480 |
| 2-14 | Asp | Tyr.Me (6:1) | THF | 91.8 | 890 |
| 2-17 | Phe | Tyr.Me (1:1) | THF | 73.0 | ND |
| 2-18 | Tyr | Tyr.Me (1:1) | THF | 65.7 | ND |
| 2-19 | Phe | Tyr.Me (5:1) | THF | 78.3 | ND |
| 2-20 | Tyr | Tyr.Me (5:1) | THF | 63.3 | ND |

It was found that the initiation by Tyr.Me is very fast (No. 2-17 to 2-20) and all the NCA has been converted after 2 hours. From GPC data, it was observed that the molecular weight of the polymer increased with increasing ratio of [M]/[Tyr.Me] and the polydispersity is quite narrow. The existence of a Tyr.Me residue in the polymers was confirmed by $^1$H NMR spectra. In conclusion, Tyr.Me is a novel and effective initiator for the polymerization of amino acid NCA's.

Sample No. 2-13 represents a polymerization initiated with β-alanine and terminated with succinic anhydride. As β-alanine is insoluble in most organic solvents, the reaction was carried out in refluxing THF. As a result, the polydispersity of the polymer obtained was broader than that of the polymers initiated by Tyr.Me.

EXAMPLE 5

Preparation of Proteinoids by the DPPA Method (#1)

This is an example of a direct polycondensation of Asp.Bz in the presence of DPPA and triethylamine (TEA) as a base under various polymerization conditions ((a), (b), (c), and (d)). The molecular weight of the polymers, as well as polydispersity, was evaluated in each case by GPC. The polymers were characterized by IR and NMR spectroscopy.

Asp.Bz was prepared by the esterification of L-aspartic acid as follows: L-aspartic acid (26.6 g, 0.2 mole) was suspended in 300 ml of freshly distilled benzyl alcohol in a 500 ml round bottom flask, followed by addition of 45 ml of concentrated hydrochloric acid (12N). The mixture was heated up to 60° C. under vigorous stirring for 30 minutes. Thereafter, the reaction solution cooled to room temperature. Triethyl amine (about 56 ml) was added to neutralize (to a pH of about 7) the solution. The crude product was collected by filtration, washed with ethanol and acetone, dried in vacuo, and crystallized twice from hot water. 18 g of product was obtained (% yield=44%). M.pt=217° C.

Commercial DPPA was used without further purification. TEA was distilled before use. Solvents for polymerization were purified by conventional methods. The direct polycondensation of Asp.Bz was carried out by stirring a dimethyl formamide (DMF) solution of the monomer in the presence of DPPA and TEA. The mixture was stirred for 1 h at 0°–10° C. followed by stirring at room temperature for two days. The resulting polymer was precipitated in a large amount of water, collected by filtration, and then dried in vacuo.

a. Effect of Monomer Concentration

Listed in Table 3 are the results for the polymerization of Asp.Bz in DMF at room temperature for two days. Poly(Asp.Bz)s were obtained from these direct polycondensations in high yield.

Figure 2:
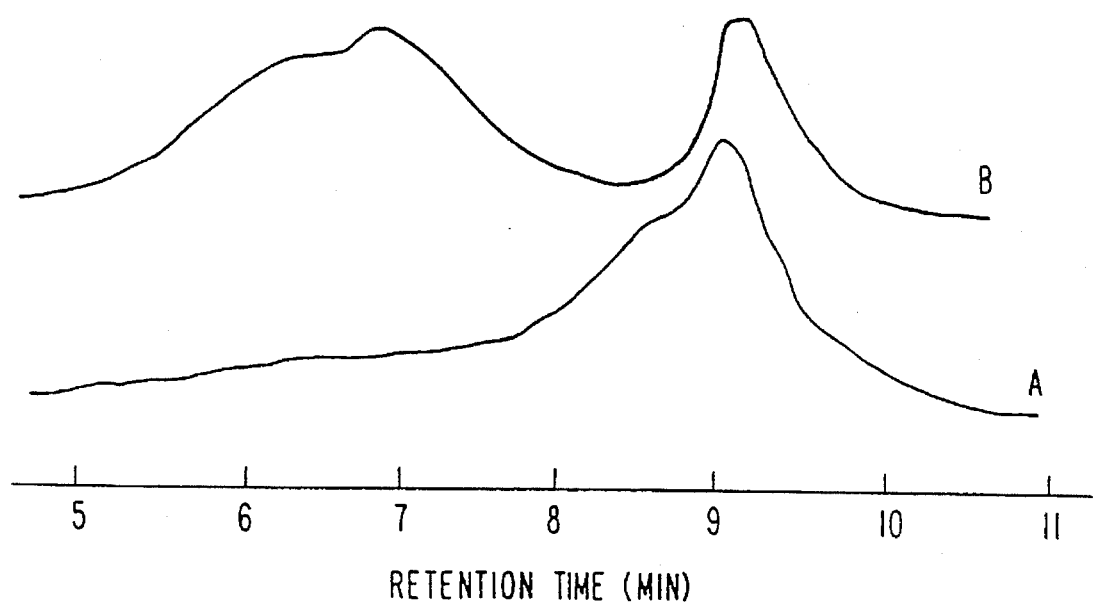
FIG. 2 illustrates the molecular weight distribution of a function of monomer concentration of poly (Asp.Bz) polymer prepared by the DPPA method as described in Example 5.

The molecular weight of the polymers was found to be dependent on the concentration of the monomer [M]. Low molecular weight polymers with broad distribution were obtained from a low [M] (M=0.025) (FIG. 2, curve A). On the other hand, when [M] was greater than 0.2 g/mL, a polymer with a bimodal molecular weight distribution was obtained (FIG. 2, curve B). The lower molecular weight oligomers (~1000) may be due to an intramolecular termination between the terminal amino and the β-carboxylic groups. After several reprecipitations from THF/methanol, a polymer with a higher molecular weight ($M_n$=22,000) and narrow polydispersity ($M_w/M_n$=1.68) was successfully isolated from the polymer mixture prepared at [M]=1g/mL. The separation was also performed using GPC column with Bio-Beads.

TABLE 3

EFFECT OF THE MONOMER CONCENTRATION ON POLYMERIZATION OF Asp.Bz BY DPPA IN DMF AT ROOM TEMPERATURE: [DPPA]/[M] = 1.3; [TEA][M] = 2.3

| [M] (g/ml) | YIELD (%) | $M_n \times 10^{-3}$ [c] | $M_w/M_n$ |
|---|---|---|---|
| 0.025 | 71.5[a] | 1.4 | 4.15 |
| 0.033 | 74.7[a] | 1.0 | 3.50 |
| 0.05 | 67.2[a] | 1.1 | 5.11 |
| 0.10 | 63.2[b] | 0.91 | 3.70 |
| 0.20 | 85.4[b] | 16.3 (60.7), 1.0 (39.3) | 1.84, 1.13 |
| 0.50 | 86.5[b] | 11.0 (59.4), 0.92 (40.6) | 2.22, 1.08 |
| 1.0 | 97.6[b] | 15.1 (71.4, 0.88 (28.6) | 1.81, 1.05 | a) The polymer was collected by centrifugation after polymerization for 2 days;
b) The polymer was collected by filtration after polymerization for 2.5 days.
c) The values in parentheses are molar percentages.

b. Effect of Reaction Time and Temperature

Figure 3:
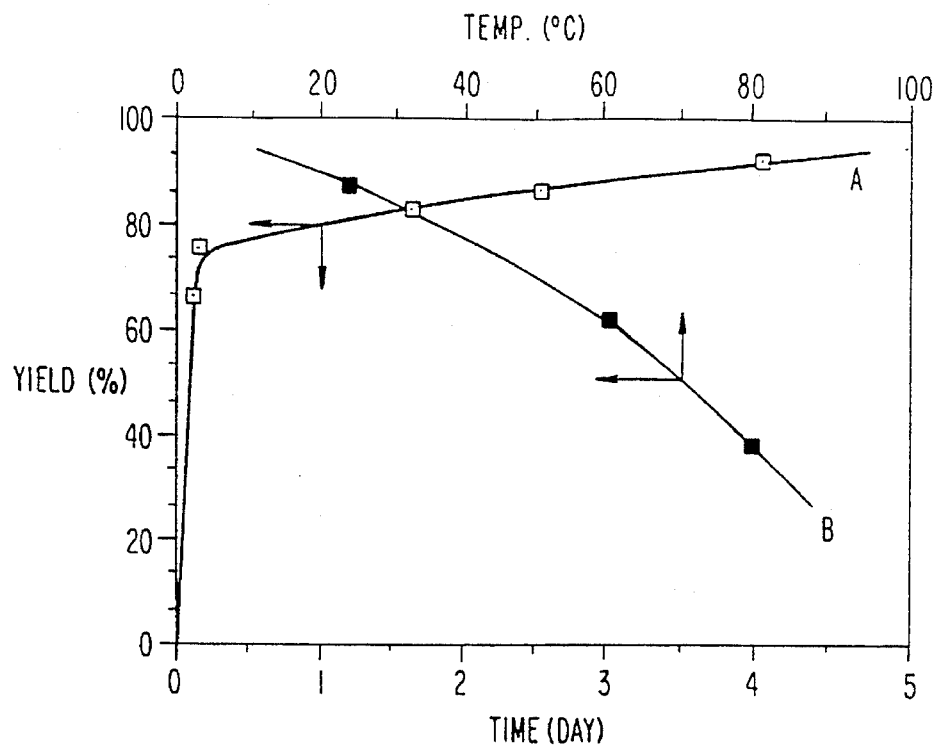
FIG. 3 illustrates the effect of reaction time duration on yields of poly (Asp.Bz) polymer prepared by the DPPA method as described in Example 5.
Figure 4:
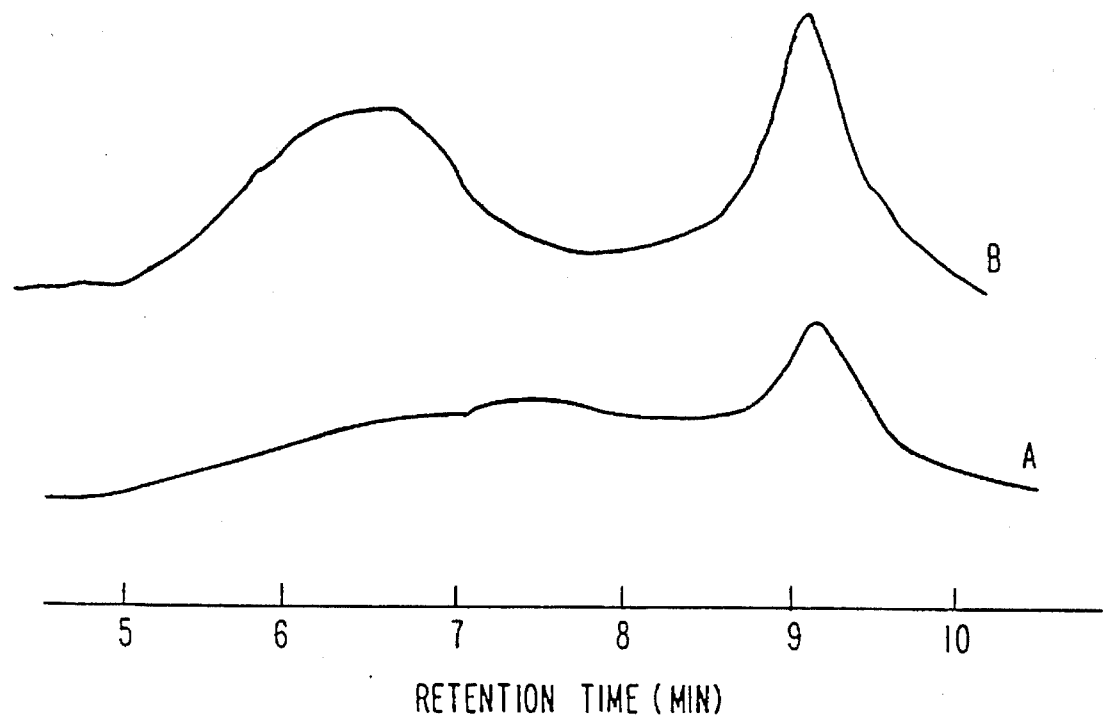
FIG. 4 illustrates the effect of temperature of the molecular weight of poly (Asp.Bz) polymer prepared by the DPPA method as described in Example 5.

The yield of the resulting polymer increased with the reaction time: 75% conversion in 5 h and 95% in 4 days (FIG. 3, curve A). The molecular weight of the resulting polymer also increased with time in the initial phase (up to 4 h) and then became almost constant (FIG. 3). The polymerization decreased with increasing temperature (FIG. 4, curve B). Polymers obtained at 60° and 80° C. were of yellow color and insoluble in THF but soluble in DMF and DMSO. This may be due to the formation of an imide ring which has been reported to occur during thermal polycondensations of aspartic acid.

c. Effect of Molar Ratios [DPPA]/[M] and [TEA]/[M]

Figure 5:
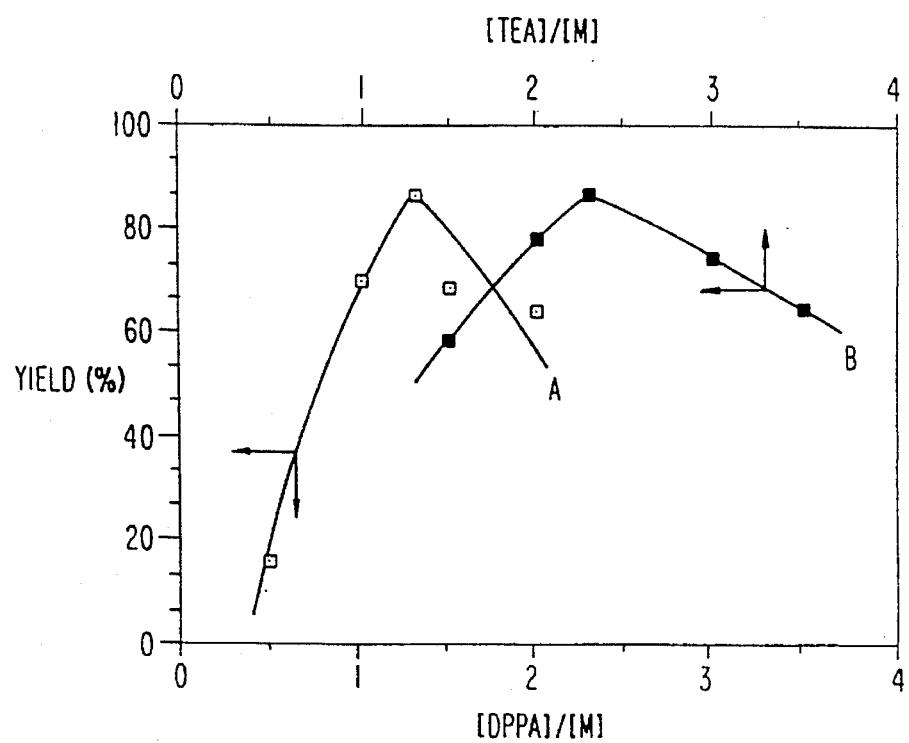
FIG. 5 illustrates the effect of changing the molar ratios of [DPPA]/[M] on the molecular weight of poly (Asp.Bz) polymer by the DPPA method as described in Example 5.

The dependence of the yield and the molecular weight of the polymer on the molar ratios of [DPPA]/[M], as well as [TEA]/[M], was investigated (Table 4). The highest yield was obtained at a [DPPA]/[M] of 1.3 and a [TEA]/[M] of 2.3 (FIG. 5). These observations are in agreement with the results reported by Nishi et al. Higher molecular weight products were obtained in the range of [DPPA]/[M]=1.3–2.0 and [TEA]/[M]=2.0–3.0, respectively.

TABLE 4

EFFECT OF THE MOLAR RATIOS OF DPPA AND TEA ON POLYMERIZATION OF Asp.Bz IN DMF AT ROOM TEMPERATURE: [M] = 0.50 g/ml

| [M]/DPPA | [M]/[TEA] | YIELD (%) | $M_n \times 10^{-3}$ [a] | $M_w/M_n$ |
|---|---|---|---|---|
| 0.5 | 2.3 | 16.3 | 0.81 | 4.09 |
| 1.0 | 2.3 | 69.6 | 3.1 (45.4), 0.39 (54.6) | 2.58, 1.48 |
| 1.3 | 2.3 | 86.5 | 11.0 (59.4), 0.92 (40.6) | 2.22, 1.08 |
| 1.5 | 2.3 | 69.4 | 15.9 (34.2), 0.83 (65.8) | 1.77, 1.21 |
| 2.0 | 2.3 | 64.3 | 13.1 (58.3), 0.89 (41.7) | 1.87, 1.09 |
| 1.3 | 1.5 | 58.4 | 6.0 (39.3), 0.63 (60.7) | 2.43, 1.37 |

TABLE 4-continued

EFFECT OF THE MOLAR RATIOS OF DPPA AND TEA ON POLYMERIZATION OF Asp.Bz IN DMF AT ROOM TEMPERATURE: [M] = 0.50 g/ml

| [M]/DPPA | [M]/[TEA] | YIELD (%) | $M_n \times 10^{-3}$ [a] | $M_w/M_n$ |
|---|---|---|---|---|
| 1.3 | 2.0 | 78.3 | 13.3 (64.3), 0.92 (35.7) | 1.87, 1.19 |
| 1.3 | 3.0 | 74.6 | 13.6 (64.8), 0.83 (35.2) | 1.98, 1.18 |
| 1.3 | 3.5 | 65.0 | 8.3 (60.0), 0.80 (40.0) | 2.70, 1.10 | a) The values in parentheses are molar percentages.

d. Effect of Solvent

A comparison of the polymerizations in different solvents is shown in Table 5. It can be seen from this table that the yield and the molecular weight of the polymer are influenced by the solvents used. Higher yields were obtained in DMF while higher molecular weights were obtained in THF and in bulk. On the other hand, the polymerization in dioxane gave a lower molecular weight product, and therefore is preferred.

TABLE 5

EFFECT OF THE SOLVENTS ON POLYMERIZATION OF Asp.Bz AT ROOM TEMPERATURE FOR 2 DAYS [M]/[DPPA] = 1.3, [M]/[TEA] = 2.3, [M] = 0.50 g/ml

| SOLVENT | YIELD (%) | $M_n \times 10^{-3}$ [b] | $M_w/M_n$ |
|---|---|---|---|
| DMF | 86.5 | 11.0 (59.4), 0.92 (40.6) | 2.22, 1.08 |
| DMSO | 70.6 | 11.5 (78.9), 1.05 (21.1) | 1.87, 1.13 |
| THF | 49.9 | 29.6 (74.6), 1.14 (25.4) | 1.31, 1.13 |
| ACETONITRILE | 71.1 | 20.3 (79.3), 1.05 (20.7) | 1.65, 1.14 |
| DIOXANE | 70.5 | 4.7 (68.5), 0.82 (31.5) | 3.80, 1.13 |
| NONE[a] | 61.2 | 29.8 (82.8), 0.86 (17.2) | 1.32, 1.16 | a) Bulk polymerization.
b) The values in parentheses are molar percentages.

EXAMPLE 6

Preparation of Proteinoids by the DPPA Method (#2)

Copolymerizations of Asp.Bz with other amino acid monomers such as γ-benzyl glutamate (Glu.Bz), β-alanine (Ala), Phenylalanine (Phe), and O-benzyl tyrosine (Tyr.OBz) in the presents of DPPA were carried out using the same procedure as that for the homopolymerization of Asp.Bz (Example 5). Random copoly(amino acids) were obtained in high yield (>77%) as shown in Table 6. This indicates that the copolymerization of amino acids using DPPA is a useful approach to copolypeptide synthesis. Bimodal molecular weight distributions were also observed in these cases similarly to the homopolymerization of Asp.Bz.

TABLE 6

COPOLYMERIZATION OF α-AMINO ACIDS IN THE PRESENCE OF DPPA AS CONDENSING AGENT IN DMF AT ROOM TEMPERATURE FOR 2 DAYS

| POLYM. NO. | COMONOMER COMPOSITION | YIELD (%) | $M_w$ | $M_w/M_n$ |
|---|---|---|---|---|
| Co.1DPPA | Asp.Bz—Glu.Bz (1:1) | 97.4 | 15900, 1080 | 1.76, 1.13 |
| Co.2DPPA | Asp.Bz-β-Ala | 91.2 | 1590 | 1.18 |

TABLE 6-continued

COPOLYMERIZATION OF α-AMINO ACIDS IN THE
PRESENCE OF DPPA AS CONDENSING AGENT IN
DMF AT ROOM TEMPERATURE FOR 2 DAYS

| POLYM. NO. | COMONOMER COMPOSITION | YIELD (%) | $M_w$ | $M_w/M_n$ |
|---|---|---|---|---|
| | (1:1) | | | |
| Co.3DPPA | Asp.Bz—Phe (1:1) | 89.7 | 13700, 800 | 1.89 1.25 |
| Co.4DPPA | Asp.Bz—Tyr.OBz (1:1) | 87.3 | 9000, 1000 | 1.78, 1.17 |
| Co.5DPPA | Asp.Bz—Glu.Bz—Phe—Tyr.OBz (1:1:1:1) | 92.5 | 16800, 960 | 1.66, 1.14 |

EXAMPLE 7

Reductive Debenzylation of Proteinoids Produced by the DPPA Method

The example illustrates a preferred method for the removal of benzyl protective groups in poly(Asp.Bz) and poly(Glu.Bz) by catalytic hydrogenation.

The hydrogenation of the polymers was carried out according to the following procedure: To a solution of the polymer in THF/methanol (1:1, v/v), Pd on active carbon (10%) was added in the amount of 1/10 of the polymer weight. After the replacement of air by nitrogen, hydrogen gas was introduced into the system and maintained with a balloon. The reaction mixture was stirred at room temperature overnight. After removing the catalyst by filtration and concentrating the solution, the mixture was poured into a large amount of petroleum ether to precipitate the polymer. The polymer obtained was then dried in vacuo.

The completion of the hydrogenation was confirmed by $^1$H NMR of the polymer. In most cases, useful water-soluble polymers were produced. The hydrogenation is an effective and lean procedure benzyl group removal.

EXAMPLE 8

Preparation of Empty Microspheres with Glu, Asp, Tyr, Phe Proteinoid

This Example illustrates a method for the preparation and cleaning of empty microspheres.

PROCEDURE

1. Reagents:
   a. Proteinoid powder prepared as described in Example 1
   b. Anhydrous citric acid (USP)
   c. Gum acacia NF
   d. Deionized water
   e. Glatial acetic acid
2. Equipment
   a. Dialysis membrane tubing (Spectrum 6, 10 mm, 50,000 MW cut off)
   b. Ph meter
   c. Ependorf pipette (0–100 ul) and tips
   d. Plastic closures for dialysis tubing (Spectrum)
   e. Water bath, 40° C.
   f. liquid Nitrogen
   g. lyophilization flasks 3. Preparation of Solutions:
   a. Proteinoid solution—Dissolve 100 mg proteinoid in 1 ml deionized water (or multiples thereof). Filter through a Whatman #1 filter paper (if necessary) and keep at 40° C. in a water bath. This is solution A.
   b. 1.7N citric acid with 0.5% acacia—Dissolve 5 g of acacia and 109 g of citric acid in 1 liter deionized water. Incubate at 40° C. This is solution B.
4. Preparation of Microspheres:
   a. Add all of solution A to solution B rapidly in one step while swirling solution B by hand, in a 40° C. water bath.
5. Cleaning of Microspheres:
   a. Transfer the suspension to dialysis tubing and seal with plastic closures, tubing should be ca. 70% full.
   b. Dialyze the microsphere suspension against 5% acetic acid (using 20 ml of acid per ml of microsphere suspension) while stirring with the magnetic stirrer.
   c. Replace the acetic acid solution every 30 minutes for two hours.
   d. After dialysis is complete, transfer to a suitable container, record total volume of microsphere suspension and measure the pH.
   e. Flash freeze in liquid nitrogen and lyophilize for 24 hours.

EXAMPLE 9

Preparation of Microsphere Encapsulated Murine IgG Monoclonal Antibody

This experiment describes encapsulation of anti-reovirus mAb 9BG5, an mAb directed against the sigma-1 gene product (Hemaglutinin, HA3) of the Reovirus Type 3. HA3 binds to the cell surface receptor for Reovirus type 3, and mAb 9GB5 interferes with viral binding to the receptor.

Mouse IgG monoclonal antibody 9BG5 was prepared and purified as described W. V. Williams et al. (1991) *J. Biol. Chem.*, Vol. 266(8), pages 5182–5190, as well as references cited therein, using a purified Reovirus type 3 preparation (W. V. Williams et al. (1988) *Proc. Natl. Acad. Sci.* U.S.A, Vol. 85, pages 6488–6492. The purified 9BG5 used in this Example had a protein concentration of 1.5 mg/ml in phosphate buffered saline (pH 7.2).

Microspheres encapsulating mAb 9BG5 were prepared having final concentrations of GluAspTyrPhe proteinoid (formulation 303) 50 mg/ml, mAb 0.7 mg/ml and gum arabic 0.5% in 0.85N citric acid. Empty microspheres were prepared to contain the same final concentrations, except mAb was omitted. Alicfuots (0.5 ml), in duplicate, of both mAb and empty microspheres preparations were centrifuged at 5000 RPM. Pellets and supernatants were frozen prior to analysis by Western blotting to determine antibody encapsulation efficiency.

Figure 6:
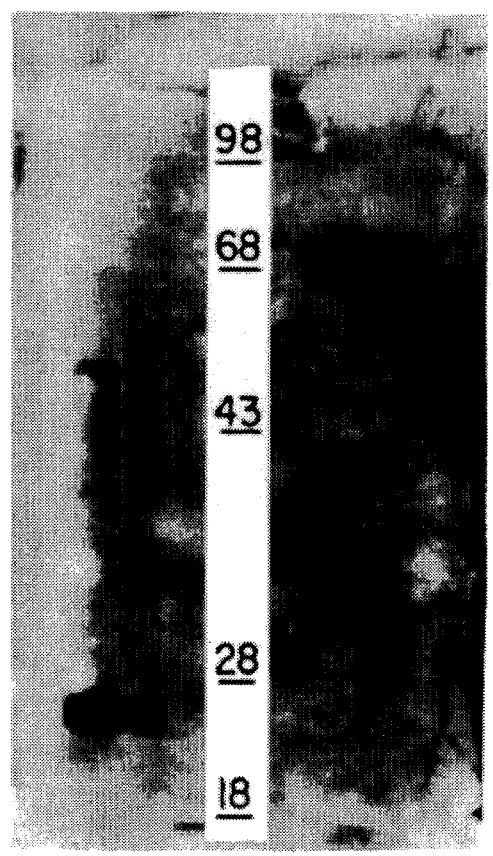
FIG. 6 is a photograph of an x-ray film of the western immunoblot analysis, as described in Example 9, of purified murine mAb 9BG5 (2 µg, lane 1; 1 mg, lane 2; and 0.25 µg, lane 3); empty microsphere supernatant after encapsulating process (no mAb) (lane 4); empty microsphere pellet (lane 5); microsphere encapsulated mAb supernatant after encapsulating process (lane 6); and microsphere encapsulated mAb pellet. Lane MW contained standard molecular weight markers.

FIG. 6 is an x-ray film of a Western blot analysis of purified mAb 9BG5, empty microspheres (no mAb added), and microspheres containing 9BG5. The analysis was done by immunoblotting with anti-mouse IgG which specifically reacted with mAb 9BG5 and contained the following:

| Lane | Sample |
|---|---|
| 1 | 2 µg 9BG5 mAb |
| 2 | 1 µg 9BG5 |

-continued

| Lane | Sample |
|------|--------|
| 3 | 0.25 µg 9BG5 |
| MW | molecular weight markers |
| 4 | Empty microsphere supernatant after encapsulation |
| 5 | Empty microsphere pellet |
| 6 | mAb containing supernatant after encapsulation |
| 7 | mAb containing microsphere pellet |

The data indicates that the 9BG5 microspheres contained about 40% of the mAb in the pellet and the remaining 60% did not incorporate in the microspheres and was left in the supernatant. The empty microspheres did not contain antibody in the supernatant or the pellet as was expected.

The relative mobility (molecular weight) of the pure mAb is slightly different than the mAb in the microspheres. This is most likely due to different salt concentrations in the samples, because the encapsulation process employed 0.8M salt solution.

EXAMPLE 10

Effect of Additives on Stability of Microspheres Encapsulated with Murine mAB 9BG5

Various proteinoid microsphere formulations were screened, with or without additives, to determine optimal microsphere-forming conditions and concentrations of mAb required for microsphere formation.

The mAb 9BG5 preparations used to prepare the encapsulated microspheres had a protein concentration of approximately 2 mg/ml in phosphate buffered saline.

Final proteinoid concentration was 50 mg/ml and 5% w/w) gum acacia ("gum") or gelatin ("gel"). All spheres were prepared in 0.85N citric acid. Empty spheres were included for use as controls, and they were prepared in the same manner with the omission of mAb. Duplicate (0.5 ml) aliquots of microsphere suspension were centrifuged at 5000 RPM. Pellets and supernatants were frozen in dry ice prior to analysis.

Table 7 lists samples that were prepared.

TABLE 7

| SAMPLE | PROTEINOID | ADDITIVE | FINAL PROTEIN (mg/ml) |
|--------|-----------|----------|----------------------|
| 1 | 326 | Gum | 0 |
| 3 | 326 | Gel | 0 |
| 5 | 334 | Gum | 0 |
| 7 | 334 | Gel | 0 |
| 9, 10 | 326 | Gum | 0.5 |
| 11, 12 | 326 | Gum | 0.25 |
| 13 | 326 | Gel | 0.25 |
| 15, 16 | 334 | Gum | 0.25 |
| 17, 18 | 334 | Gel | 0.25 |

In order to test resistance to freeze and thawing and the integrity of the microspheres containing mAb, one of each pair of duplicate pellets were washed by gentle resuspension in 0.25 ml of 0.85N citric acid. The pellets were then analyzed next to the unwashed pellets to test whether any mAb was lose in the washing.

The samples were analyzed by conventional Western blotting as described in Example 9. Pellets were dissolved in sodium dodecyl sulfate with 0.05N NaOH and analyzed under reducing conditions (breaks up the mAb into 50 kDa and 25 kDa bands). Aliquots (50 µl) of supernatants were analyzed under non-reducing conditions (expected intact 150 kDa mAb). This was done to determine differentially whether the mAb left behind is denatured or intact.

As can be seen from the X-ray film from the Western Blots (FIG. 7), pellets of samples 9 and 10, and 11 and 12 contain between 5 and 10 µg of mAb. The washed samples did not lose any significant amount of mAb, suggesting that the microspheres remained intact after freeze-thawing.

The supernatants of samples 9 and 11 had no significant amount of mAb, indicating that unincorporated material was lost during preparation.

Sample 17 had some mAb encapsulated which was lost after washing (see number 18). This sphere preparation was not resistant to freeze-thawing. Additionally, a band at a MW of 150 kDa for sample 17 supernatants indicates that a significant amount of mAb is left behind after microsphere formation.

Based on these results, it appears that the mAb remains intact and therefore the encapsulating procedure does not degrade it. The empty microsphere controls did not produce any bands, as expected because they have no mAb.

EXAMPLE 11

Efficacy of Encapsulated Murine IgG Monoclonal Antibody

In this Experiment, a mAb 9BG5 microsphere preparation and unencapsulated mAb 9BG5 were evaluated in rats.

The mAb 9BG5 (1 mg/ml), prepared as described in Example 9, was encapsulated in GluAspTyrPhe proteinoid microsphere formulation with gum arabic. The mAb microspheres were prepared (at 40° C.) from a proteinoid suspension containing 0.25 mg/ml mAb and 50 mg/ml proteinoid in 0.85N citric acid-0.5% gum. Empty microspheres were prepared similarly, but did not contain mAb. Since 30% of the mAb was found to be encapsulated, the mAb microspheres were estimated to contain 0.075 mg/ml mAb and this value was used to determine dosages. The mAb microspheres were examined microscopically and appear to be a fairly homogeneous preparation.

For animal dosing, appropriate aliquots of microspheres were centrifuged at 5000 RPM for 15 minutes, and Fellers were resuspended in 1.0 ml of 0.85N citric acid-0.5% gum.

A purified mAb solution (0.95 mg/ml mAb in 0.85N citric acid-0.5% gum) was used for oral garage. This solution bas prewarmed to 40° C. prior to administration. For IV administration, a purified mAb solution (1 mg/ml mAb in phosphate buffer saline) was used.

The amounts and administration routes employed in the experiment are as follows:

1. Empty microspheres (no mAb):1 ml aliquot containing 50 mg empty microspheres by oral garage (rats #2312 and 2313).
2. mAb 9BG5 microspheres:3.7 mg mAb/kg body weight of rat by oral gavage (rat #2287, 2288, 2290, and 2291).
3. unencapsulated mAb 9GB5:0.73 mg/kg body weight of rat by
   intravenous administration (rats #2292, 2293, and 2311).
4. unencapsulated mAb 9BG5:3.7 mg/kg body weight of rat by oral garage (rats #2314 and 2315).

Baseline blood samples (1 ml aliquots) were withdrawn from each rat just prior to dosing ("0" time). After dosing, blood samples were drawn at 1 h, 6 h and 24 h. The blood samples were processed immediately and sera were stored frozen at −20° C.

Thawed serum taken from the experimental animals were analyzed by conventional ELISA techniques, in triplicate, using purified reovirus type 3 and $V_L$SH dimeric peptides immobilized ran multi-well plates (W. V. Williams et al (1991) *J. Biol. Chem.*, Vol. 266(8), pages 5182–5190). Control plates included wells having no immobilized reovirus and $V_L$SH peptides to which mAb (1 mg/ml) was added. $V_L$SH peptide (W. V. Williams et al. ibid, Table 1) is a synthetic variant of $V_L$ peptide, the latter which corresponds to a portion of the light chain variable CDR II region of 87.92.6 antibody. The 87.92.6 antibody displays idiotypic and anti-idiotypic behavior towards reovirus type 3 receptor and mAb 9BG5, respectively (W. V. Williams et al. ibid). The bound protein content of each well were measured by standard protein methods, e.g. Lowry method, and the results for each multi-well plate are shown in FIGS. 8(a–c), respectively.

Figure 8A:
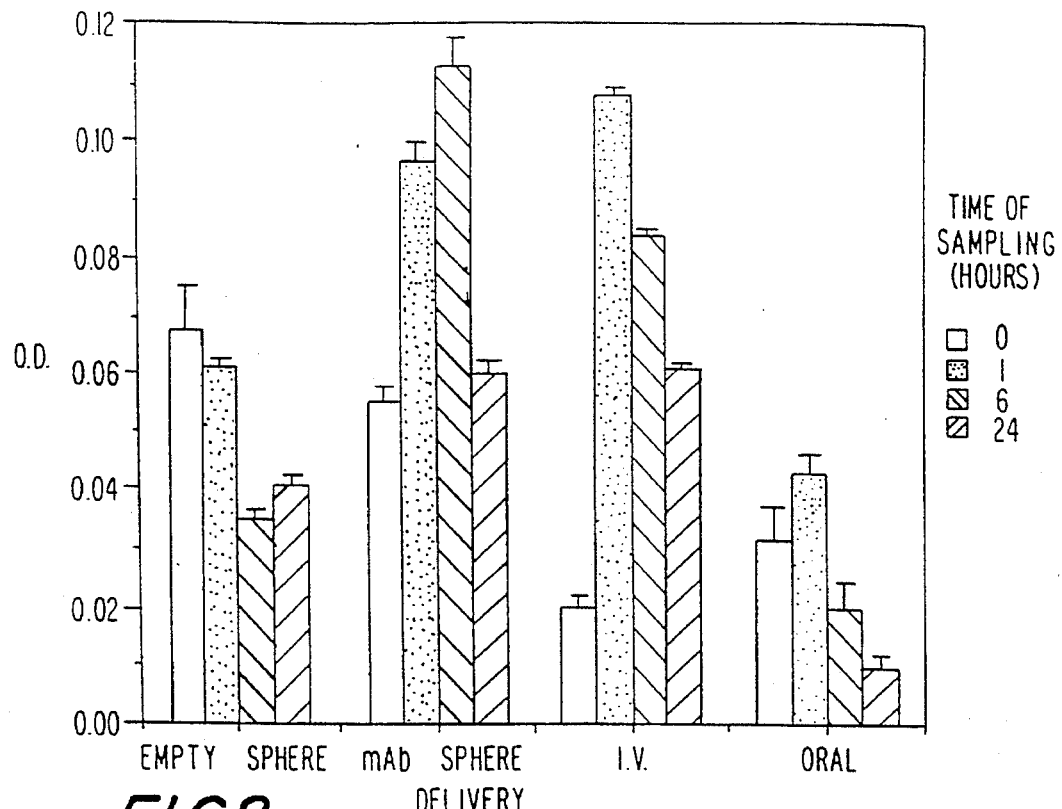
FIGS. 8 (a–c) illustrate the levels of serum proteins which bound to immobilized reovirus type 3 and $V_L$SH under ELIZA conditions as described in Example 11. "Empty spheres" refers to animals orally administered empty microspheres (no mAb 9BG5); "mAb spheres" refers to animals orally administered mAb 9BG5 encapsulated microspheres; "IV" refers to animals intravenously adminstered unencapsulated mAb 9BG5; and "oral" refers to animals orally administered unencapsulated mAb 9BG5.
Figure 8B:
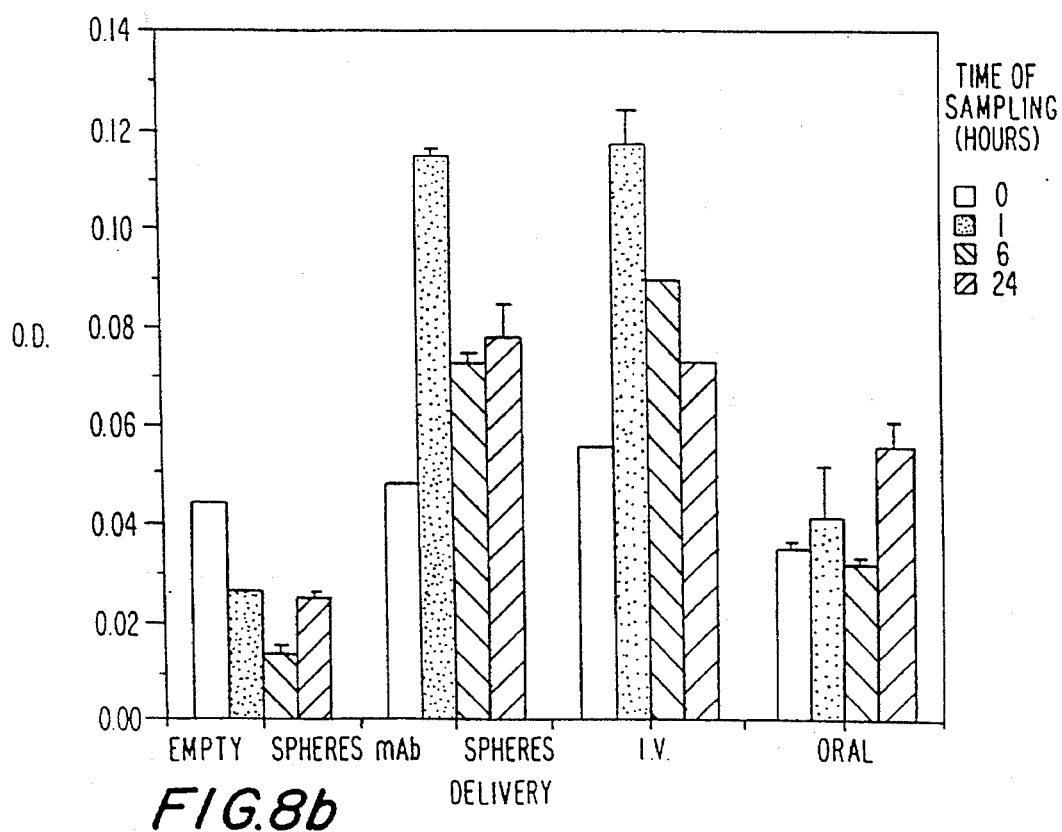
Figure 8C:
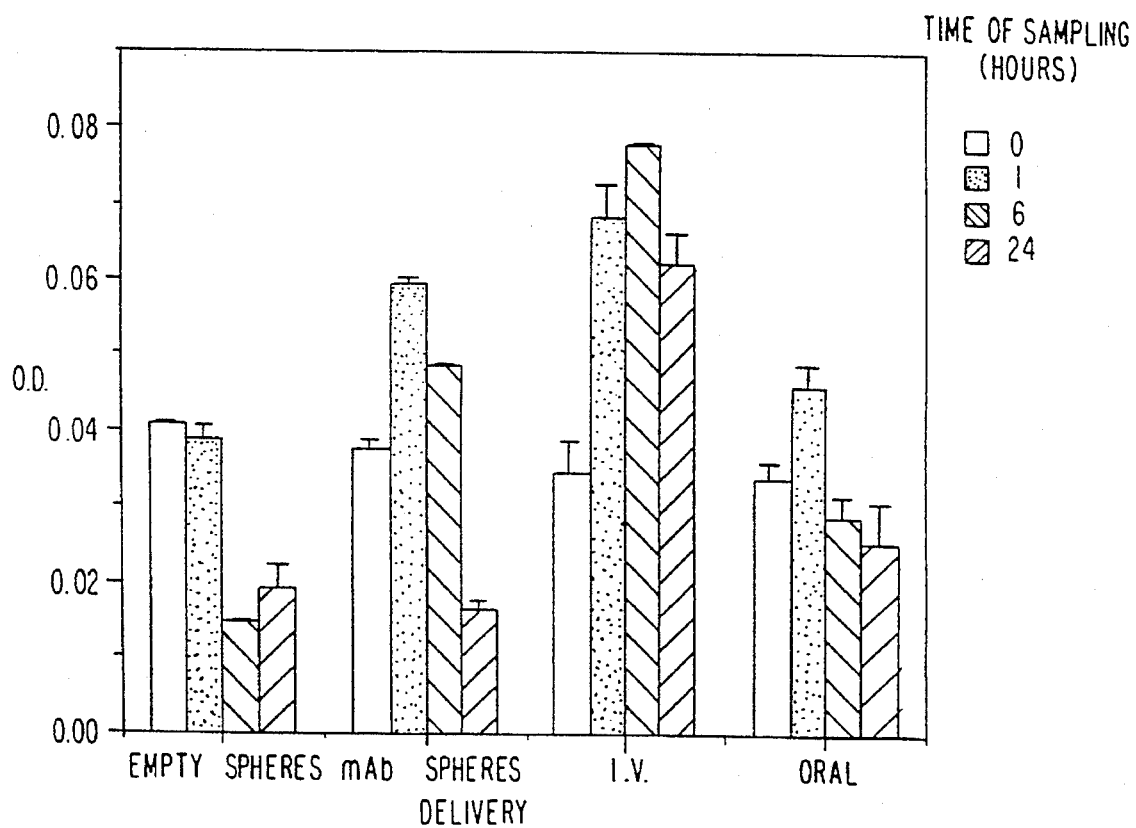

FIGS. 8 (a–c) illustrate the levels of serum proteins which bound to immobilized reovirus type 3 and $V_L$SH as detected by measurement of protein concentration. These Figures show that the serum levels of bound proteins, after 24 hours post-dosing, were highest for animals orally administered mAb microspheres and animals administered unencapsulated mAb by the IV route. Lower levels of bound serum proteins were found in animals orally adminstered uncapsulated mAb. Serum taken from the animals receiving empty microspheres (no mAb) showed non-specific serum IgG protein binding, as expected, under the assay conditions.

Figure 9A:
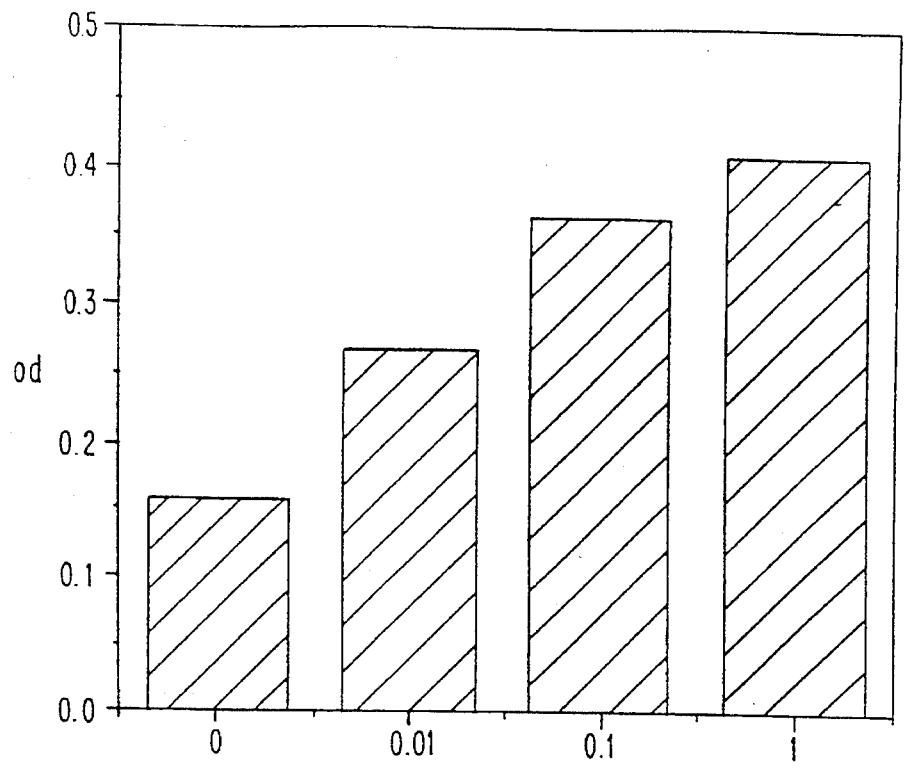
FIG. 9 show mAb binding under conventional ELIZA procedures using immobilized reovirus type 3 and $V_L$SH proteins with serial dilutions of purified mAb in 0.85N citrate-0.5% gum (FIG. 9(a)) or phosphate buffered saline (FIG. 9 (b)) as described in Example 11.
Figure 9B:
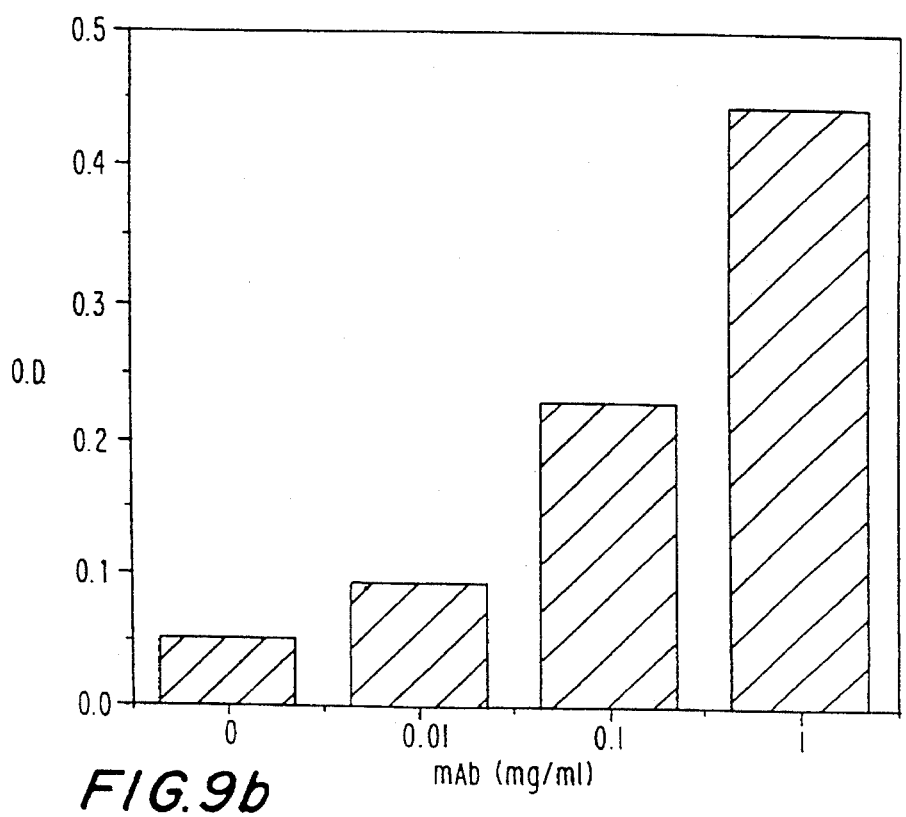

FIG. 9 show mAb binding under conventional ELIZA procedures using immobilized reovirus type 3 and $V_L$SH proteins. Serial dilutions of mAb treated with 0.85N citrate-0.5% gum FIG. 9(a) or phosphate buffered saline (FIG. 9 (b) were employed. The Figures shows that the bound protein levels were higher for mAb in citrate buffer than for mAb in phosphate. Without being bound by any theory of operation for this invention, it is believed that the binding enhancement may be due to changes in the three dimensional conformation resulting from citrate-protein binding.

In sum, serum levels of mAb, as reflected by the absorbance of bound proteins, were greater in animals receiving encapsulated mAb by the oral route or unencapsulated mAb by the IV route, than an animal receiving orally administered unencapsulated mAb.

EXAMPLE 12

Preparation of Microsphere Encapsulated Heparin

This Example describes a method for the preparation and cleaning of heparin microspheres.

PROCEDURE

1. Reagents:
   a. Proteinoid powder prepared as described in Example 1
   b. Heparin
   c. Anhydrous citric acid (USP)
   d. Gum acacia NF
   e. Deionized water
   f. Desiccant
   g. Liquid nitrogen
2. Equipment:
   a. Magnetic stirrer
   b. Buret
   c. Microscope
   d. Clinical centrifuge
   e. Dialysis membrane tubing (Spectrum 6, 10 mm, 50,000 M. W. Cutoff)
   f. pH meter
   g. Lyophilizer (Labconco #75035)
   h. Lyophilizing flasks (150–300 mL)
   i. Rotating shell freezer
   j. Isopropanol/dry ice bath or liquid $N_2$
   k. Mortar and pestle
   l. Storage containers (500 mL)
   m. Eppendorf piper (0–100 uL)
   n. Plastic closures for dialysis tubing (Spectrum)
   o. 2 mL syringe with 0.45 um Acrodisk
3. Preparation of Solutions:
   a. Proteinoid Solution A* (80 mg/ml): Add 160 mg proteinoid and dissolve to 1 ml with deionized water. Using a 2 ml syringe filter through a 0.45 um Acrodisk into a 10 ml test tube. Keep at 40° C.

*or multiples thereof.

b. Solution B (1.7N citric acid with 1% gum): Dissolve 10 g of acacia and 109 g of citric acid in 1 liter deionized water.
   c. Solution C (Heparin solution): Dissolve heparin in Solution B at 150 mg/mL and keep at 40° C.
4. Preparation of Microspheres:
   a. Add all of solution A to solution C quickly while swirling solution C slowly, by hand, in a 40° C. water bath.
5. Cleaning of Microspheres:
   a. Transfer the suspension with a syringe (no needle) to dialysis tubing and seal with plastic closures. Tubing should be no more than 70% full.
   b. Discard any amorphous material sedimented and/or aggregated on the surface.
   c. Dialyze the microsphere suspension against acetic acid (using 20 mL of acetic acid solution per ml of microsphere suspension) while stirring the acetic acid solution with a magnetic stirrer.
   d. Replace the acetic acid solution every hour. Continue dialyzing for a total of 3 hours.
6. Lyophilization:
   a. Add one part of 50% trehalose (Sigma) into nine parts of dialyzed microsphere solution. Flash freeze microspheres in a freeze-drying flask using the shell freezer adjusted to rotate at ca. 190 rpm and immersed in a liquid nitrogen bath.
   b. Freeze dry for 24 hours or until dry as evidenced by lack of self-cooling.
   c. Record weight of dry microspheres.
   d. Grind to a fine powder with mortar and pestle.
   e. Transfer to amber container, seal with desiccant, and store at room temperature.
7. Resuspension:
   a. Weigh the lyophilized powder and calculate the amount of proteinoid in the powder.
   b. Add 0.85N citric acid into the lyophilized powder at 40° C. The final concentration of proteinoid is 80 mg/ml.

EXAMPLE 13

Preparation of Microsphere Encapsulated Insulin

This Example illustrates a method for the preparation insulin microspheres.

PROCEDURE

1. Reagents:
   a. Proteinoid powder (Emisphere)
   b. Anhydrous citric acid (USP)
   c. Gelatin (USP)
   d. Porcine insulin (Novo Nordisk)
   e. Deionized water (USP)
2. Equipment:
   a. Water bath
   b. 0.2 micron Acrodisk filter
   c. Sterile syringe (10 cc)
   d. Glass or plastic vessel of appropriate volume for desired amount of microsphere solution.
3. Preparation of Solutions:
   a. 1.7N citric acid with 5.0% gelatin: Dissolve 109 mg anhydrous citric acid and 50 mg gelatin per 1 ml of deionized water at desired volume** and incubate in water bath at 40° C. until gelatin is completely dissolved. This may be prepared and stored at 40° C. for later use.

**Proteinoid and Insulin solutions should each be prepared an one-half the total volume of the final microsphere solution desired.

b. Insulin solution: Dissolve 12 mg insulin per 1 ml of 1.7N citric acid with 5% gelatin at 40° C. at desired volume.
   c. Proteinoid solution: Dissolve 100 mg proteinoid per 1 ml deionized water at room temperature and desired volume. Using syringe and 0.2 micron Acrodisk, filter the solution to ensure a clear liquid and incubate in a water bath at 40° C. See Section 5b.
4. Preparation of Microspheres:
   a. Proteinoid solution and insulin solution are combined at equal volumes sufficient to produce the final desired volume of microspheres.
   b. Rapidly add the filtered proteinoid solution to the insulin solution at 40° C. while simultaneously and constantly swirling the insulin solution to ensure a thorough mixing.

EXAMPLE 14

Procedure for Preparation of Encapsulated Erythropoietin Microspheres

Encapsulation of human erythropoietin (EPO) in proteinoid microspheres was performed in the same manner described in Example 13. EPO was obtained from Genetic Institute (Cambridge, Mass., USA, now available from Amgen Corp., Thousand Oaks, Calif., USA) and a 150 mg/mL EPO solution in 1.7N citric acid with 1% gum is prepared as described in Example 13.

EXAMPLE 15

Evaluation of Microsphere Encapsulated Erythropoietin in Rats

Rats weighing 150–200 grams are anesthetized with ketamine (8.5 mg/kg) and thorazine 3.75 mg/kg) with intramuscular injection. The rat is then administered either unencapsulated erythropoietin or encapsulated erythropoietin by oral garage. In brief, an 8 French Nelaton catheter is inserted down the esophagus of the rat until the 10 cm mark on the catheter is even with the incisors. The test or control solution is drawn up into a syringe and attached to the catheter. Holding the animal upright, the solution is expressed into the stomach of the rat.

| ERYTHROPOIETIN EXPERIMENTAL SYNOPSIS | | | |
|---|---|---|---|
| Batch | Dose | Rats Responding | Comments |
| Control | 15 µg/kg | 0/4 | Fasted 15 hours. |
| 251 < 3K | 15 µg/kg | 0/4 | Access to bedding. |
| 254 < 3K | 15 µg/kg | 2/4 | Gavaged |
| Control | 15 µg/kg | 0/2 | |
| 251 < 3K | 15 µg/kg | 0/2 | Fasted 36 hours. |
| 254 < 3K | 15 µg/kg | 1/4 | 5% sucrose. |
| 270K | 15 µg/kg | 1/3 | No bedding. |
| 270G | 15 µg/kg | 3/3 | Gavaged. |
| Control | 15 µg/kg | 1/5 | Fasted 24 hours. |
| 264CP | 15 µg/kg | 1/4 | Access to bedding. |
| 270G | 15 µg/kg | 1/6 | Gavaged. |
| Control | 10 µg/kg | 0/5 | Fasted 24 hours. |
| 270G | 10 µg/kg | 3*/6 | No bedding. |
| Control | 30 µg/kg | 0/3 | Fasted 24 hours. |
| Control | 60 µg/kg | 1/4 | No bedding. |
| 270G | 30 µg/kg | 1/3 | Direct injection |
| 270G | 60 µg/kg | 1/4 | into the stomach. |
| Control | 50 µg/kg | 0/3 | |
| Control + Pepsin | 50 µg/kg | 0/4 | Direct injection |
| 270G | 50 µg/kg | 2/4 | into the intestine. |
| 270G + Pepsin | 50 µg/kg | 0/4 | |
| Control | 100 µg/kg | 1/5 | Multiple Dosing |
| 270G | 100 µg/kg | 1/5 | (5 dosing intervals |
| I.V. | 50 µg/kg | 2/2 | at t ½) |
| S.C. | 50 µg/kg | 2/2 | Gavage by stomach tube. |

*Rats were foaming at nostrils.

Figure 10:
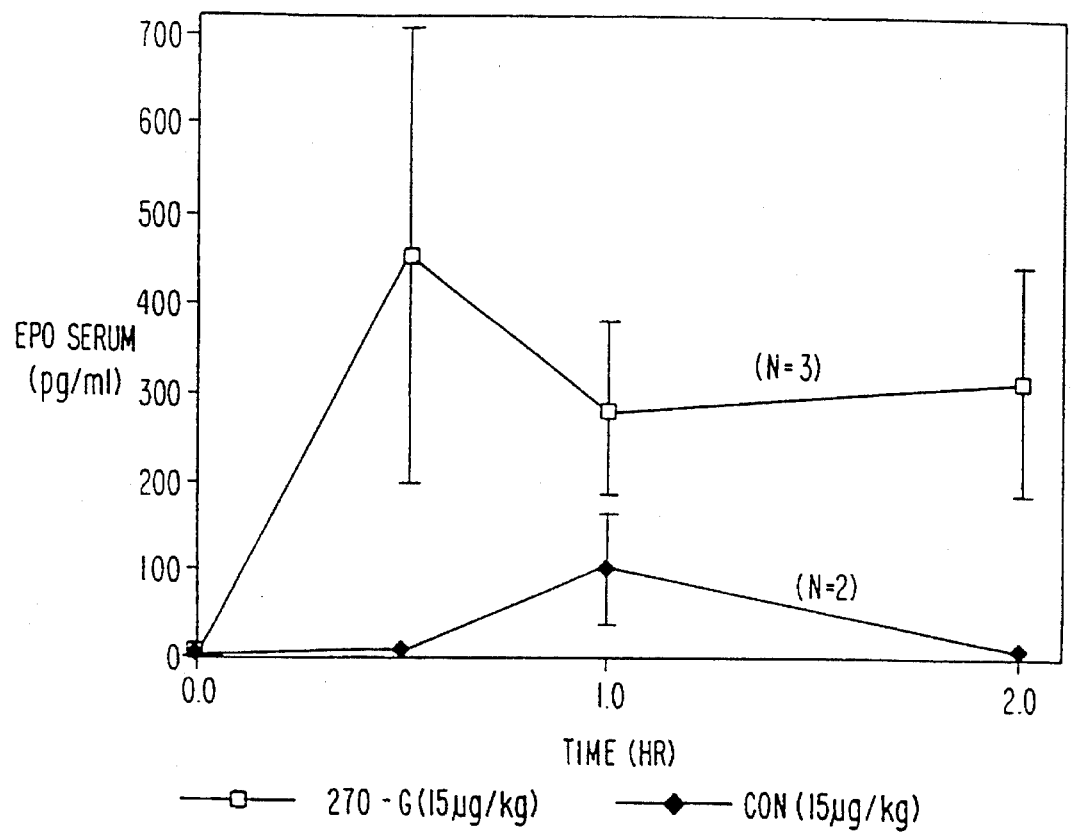
FIG. 10 illustrates levels of erythropoietin (EPO) detected in rat serum taken from rats administered microsphere encapsulated EPO (15 µg EPO/kg body weight) and encapsulated EPO (15 µg EPO/kg body weight) as described in Example 15.

FIG. 10 illustrates levels of erythropoietin (EPO) detected in rat serum taken from rats administered glutamic acid/Asp/Tyr/Phe proteinoid microsphere encapsulated EPO (15 µg EPO/kg body weight) and unencapsulated EPO (15 µg EPO/kg body weight) at t=0.5, 1, and 2 hours. Serum erythropoietin levels were determined over time with a erythropoietin enzyme immunoassay kit (Amgen, Thousand Oaks, Calif., USA). The results show that EPO serum levels in rats administered erythropoietin microspheres were relatively higher at all time points compared to rats (control) which received unencapsulated material. At t=2 hours, the EPO levels remained at approximately 300 pg/mL serum in rats administered erythropoietin microspheres while the control rats had undetectable EPO levels.

Figure 11:
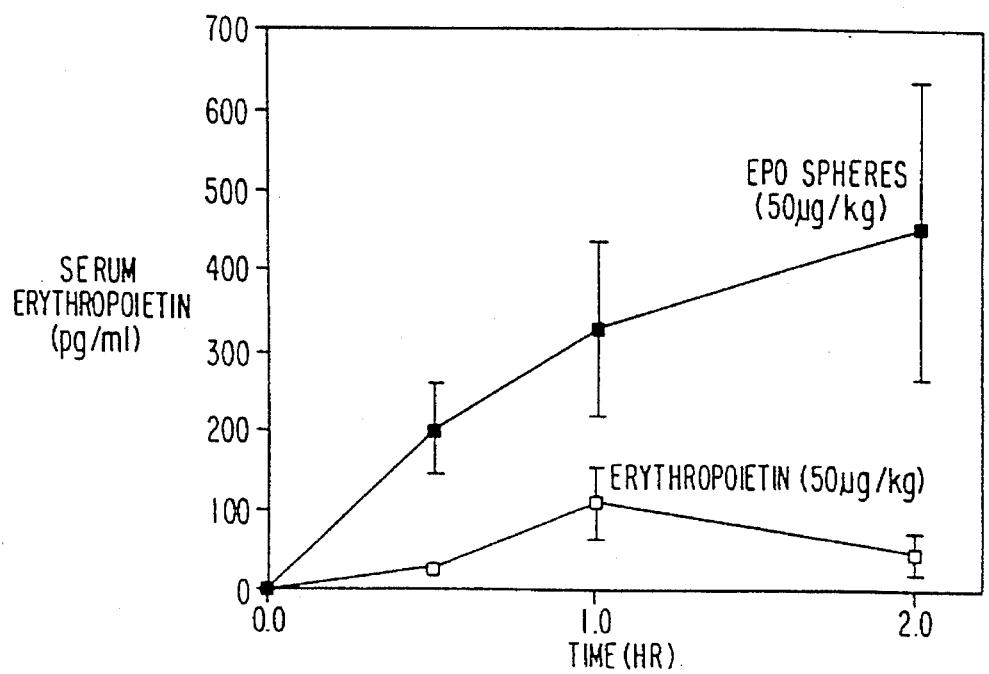
FIG. 11 illustrates EPO serum levels in rats that were administered either erythropoietin (50 µg/kg) or encapsulated erythropoietin (50 µg/kg) directly into the proximal duodenum as described in Example 15. Serum erythropoietin levels were determined over time with an erythropoietin enzyme immunoassay kit.

FIG. 11 illustrates EPO serum levels in rats that were administered either erythropoietin (50 µg/kg) or glutamine/Asp/Tyr/Phe proteinoid microsphere encapsulated erythropoietin (50 µg/kg) directly into the proximal duodenum. Serum erythropoietin levels were determined over time with the aforementioned erythropoietin enzyme immunoassay kit. The results show that EPO serum levels in rats administered erythropoietin microspheres steadily increased at a rate of approximately 50 pg/mL per hour over a range of two hours. In contrast, rats (control) which received unencapsulated EPO had EPO levels peaked at 100 pg/mL at 1 hour following administration and steadily decreased to about 50 pg/mL at the end of 2 hours.

Figure 12:
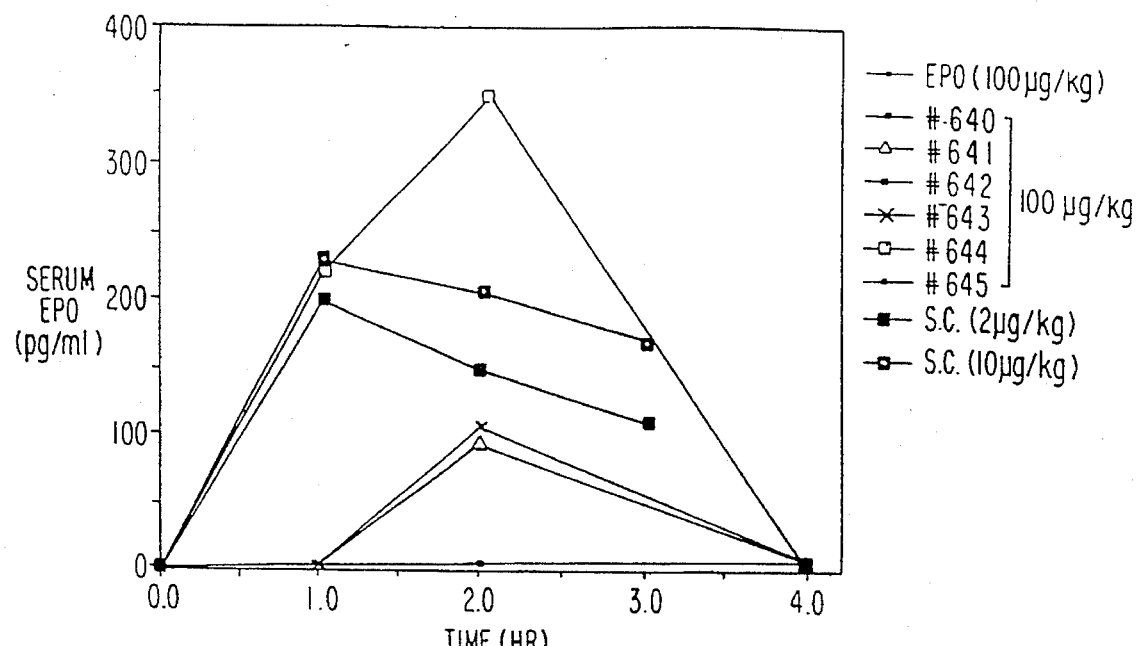
FIG. 12 illustrates EPO serum levels in rats who were orally garaged with either encapsulated or unencapsulated erythropoietin (100 µg/kg) or received a subcutaneous injection of either 2 µg/kg or 10 µg/kg as described in Example 15. Serum erythropoietin levels were determined over time with an erythropoietin enzyme immunoassay kit.

FIG. 12 illustrates EPO serum levels in rats who were orally gavaged with either glutamine/Asp/Tyr/Phe proteinoid microsphere encapsulated or unencapsulated erythropoietin (100 µg/kg); or received a subcutaneous injection of either 2 µg/kg or 10 µg/kg. Serum erythropoietin levels were determined over time with the aforementioned erythropoietin enzyme immunoassay kit. The results show that EPO serum levels in rats (#640–645) orally administered erythropoietin microspheres were relatively higher up to t=2 hours, compared to rats (EPO) which received unencapsulated material.

EXAMPLE 16

Preparation of Microsphere Encapsulated Calcitonin

Encapsulation of salmon calcitonin in proteinoid microspheres was performed in the same manner described in Example 13. Calcitonin was obtained from Sandoz (Basil, Switzerland) and a 150 mg/mL calcitonin solution in 1.7N citric acid solution with 1% gum was prepared as described in Example 13.

EXAMPLE 17

Evaluation of Calcitonin Microspheres in Monkeys

In this Example, the calcitonin microspheres prepared as described in Example 16 were evaluated in Monkeys. A single oral dose of calcitonin microspheres (0.25 mg/kg body weight) was administered to each of four monkeys according to a specified treatment. The dosage was based on the body weight taken on the morning of dosing. Blood samples were collected at hourly intervals, starting at t=0 prior to administration of the microspheres. Animals were anesthetized (approximately 10 mg/kg ketamine HCl) and placed in a primate restraint chair for dose administration by nasal gavage and initial blood sampling. When the animals were determine to be alert (head and eyes follow technician), blood samples were taken. Approximately 15 minutes prior to dose administration, the animals were allowed to drink 20–30 ml of calcium-free orange juice. After 15 minutes, a naso-gastric tube was passed into the stomach, and a 10 ml syringe was used to attempt to withdraw a small amount of stomach contents to ensure placement of the catheter. After withdrawal of the contents (or vacuum response by the syringe if no contents can be aspirated), the test material was administered, followed by a 1 ml flush of 0.85N citric acid (pH 2.0–3.0). Subsequent blood collections were then taken. Animals remained in the chairs for approximately 6 hours.

Figure 13:
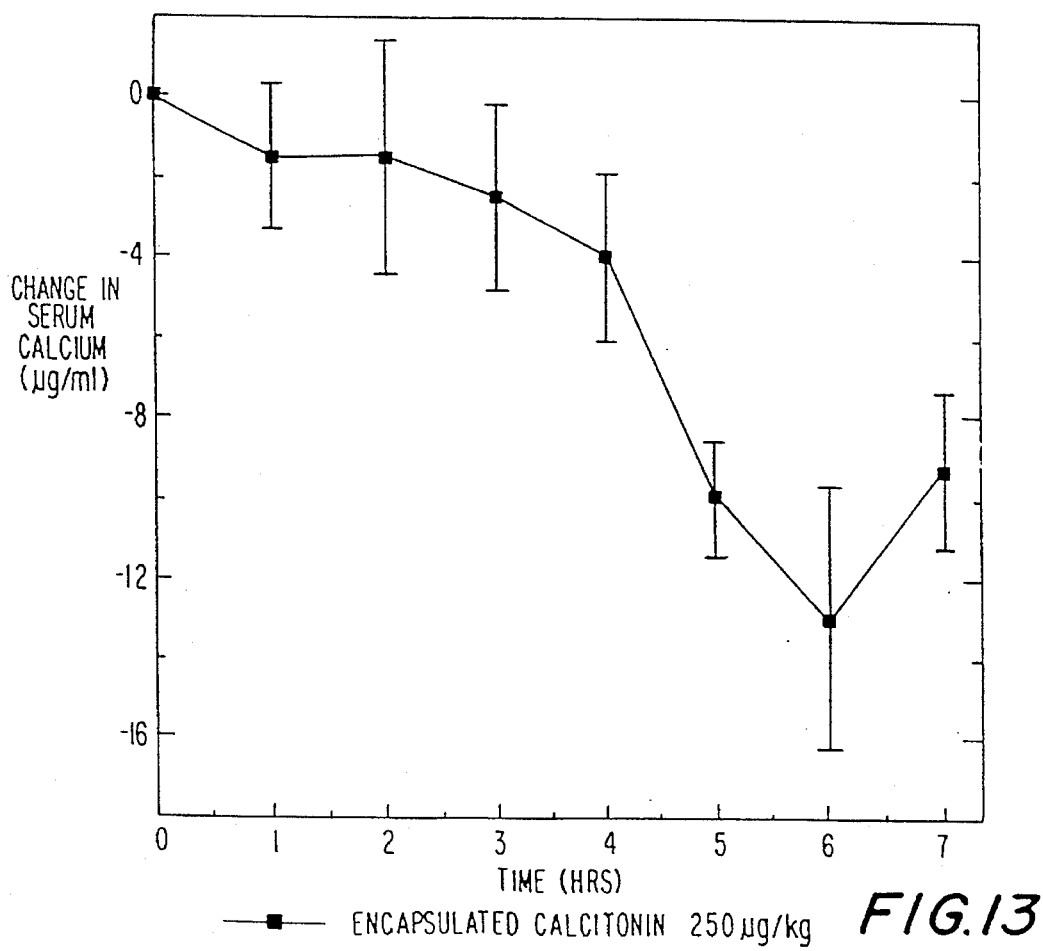
FIG. 13 illustrates serum calcium levels after oral administration of microsphere encapsulated salmon calcitonin (0.25 mg/kg body weight) in monkeys as described in Example 18.

FIG. 13 illustrates calcium serum levels after oral administration of glutamine/Asp/Tyr/Phe proteinoid microsphere encapsulated salmon calcitonin (0.25 mg/kg body weight) in four monkeys.

Figure 14:
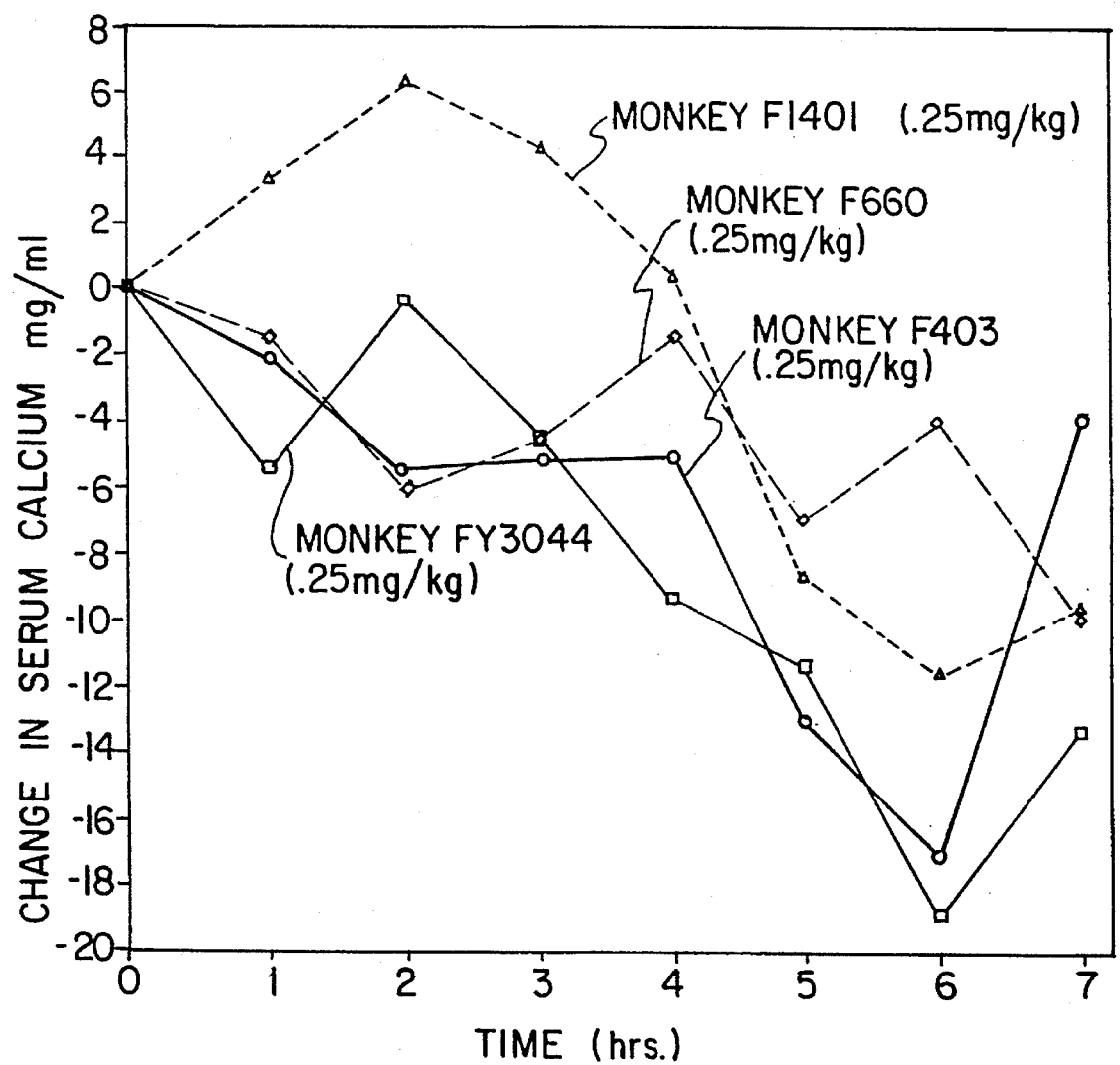
FIG. 14 illustrates the median serum calcium levels after oral administration of microsphere encapsulated salmon calcitonin (0.25 mg/kg body weight) in monkeys as described in Example 18.

FIG. 14 illustrates the median calcium serum levels at various time intervals for the four monkeys administered the calcitonin microspheres as shown in FIG. 11. The results show that encapsulated calcitonin, when orally administered, effectively reduces calcium levels gradually over a period of 6 hours.

EXAMPLE 18

Evaluation of Calcitonin Microspheres in Rats

In this Example, the calcitonin microspheres prepared in accordance with Example 17 are evaluated in rats. Nine rats are divided into three groups as follows:
1. oral calcitonin microspheres: 60 ug calcitonin/kg body weight by oral gavage (3 rats);
2. oral calcitonin microspheres: 30 ug calcitonin/kg body weight by oral gavage (3 rats); and
3. oral unencapsulated microspheres: 60 ug calcitonin/kg body weight by oral gavage (3 rats) (Control).

Oral gavage dosing of rats is performed. Calcitonin microspheres are prepared immediately prior to dosing and Group 1 rats and Group 2 rats each receive an appropriate dosage of the microsphere suspension. Group 3 rats receives the unencapsulated calcitonin. Approximately 0.5 ml of blood is withdrawn from each rat just prior to dosing ("0" time) and 1 h, 2 h and 3 h post-dosing. Serum from the blood samples are stored at −20° C.

Figure 15:
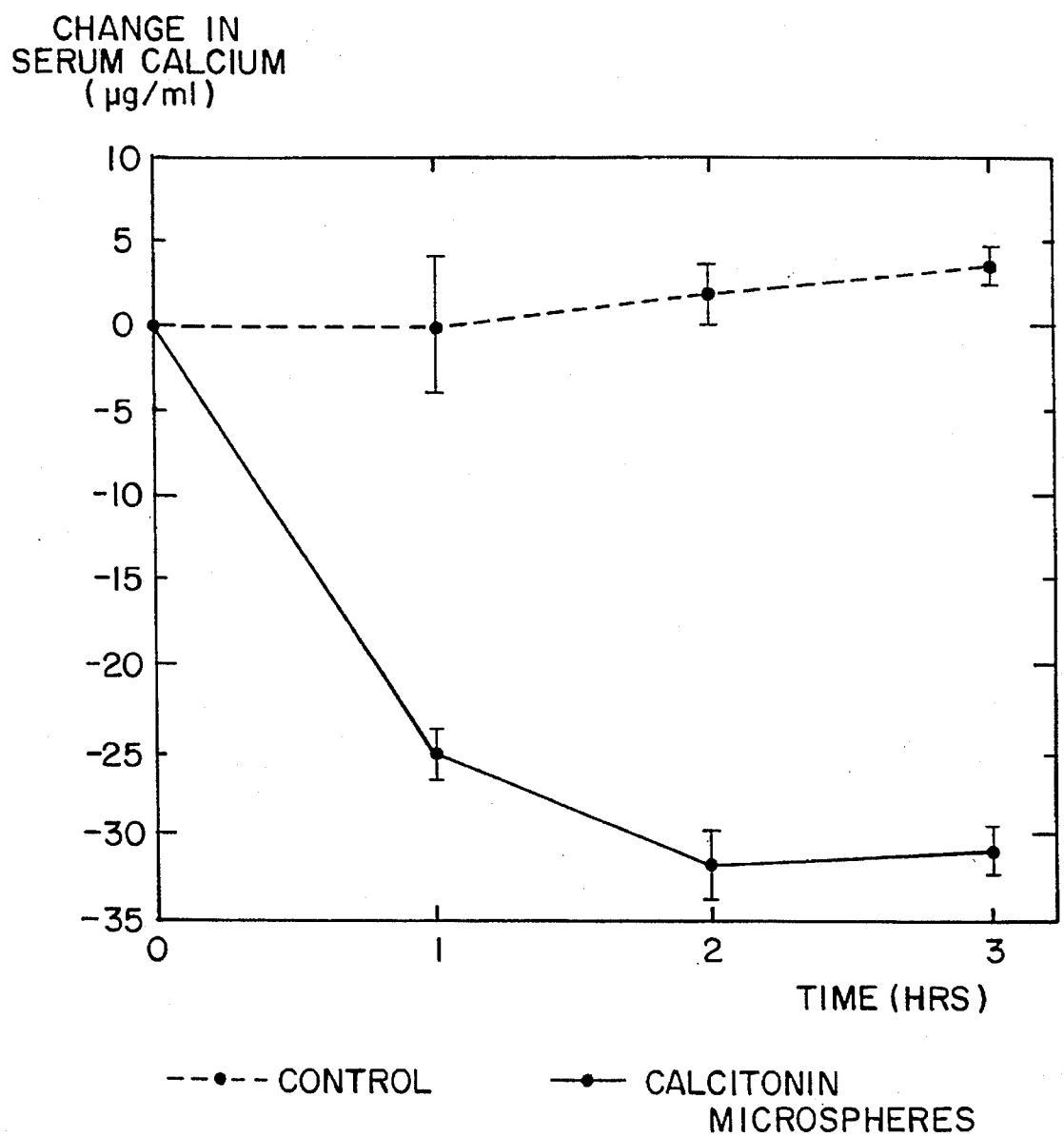
FIG. 15 illustrates serum calcium levels after oral administration of microsphere encapsulated salmon calcitonin (30 or 60 ug/kg body weight) in rats as described in Example 19.

The calcium levels of thawed serum taken from group 1–3 rats are analyzed by conventional methods. As shown in FIG. 15, sharp decreases in serum calcium levels were observed in groups 1 and 2 rats receiving the encapsulated calcitonin. In contrast, the calcium levels in group 3 rats slightly increased from t=0. The results show that encapsulated calcitonin had a greater biological effect, when administered orally, in contrast to unencapsulated calcitonin.

54

Appendix A
p 1 of 9

PROTEINOID BATCHES

| Bt. No. | #AA | COMPOSITION | ADDITIVE | TEMP C | TIME (hr) | SPHERE RATING | BATCH SIZE molar | Operator | Date |
|---|---|---|---|---|---|---|---|---|---|
| 085 | 3 | GLU2 ASP2 ILEU | --- | 170 | 3.0 | INS5 HT1 | 0.0 | | |
| 086 | 3 | GLU2 ASP2 VAL | --- | 170 | 3.0 | INS4 HT0 HEP0 | 0.0 | | |
| 087 | 3 | GLU ASP LEU | --- | 170 | 3.0 | INS5 HT3 HEP5 | 0.0 | | |
| 088 | 2 | GLU2 ASP2 EQU | SEE MEMO | 0.0 | | | 0.0 | | |
| 089 | 2 | GLU2 ASP2 EQU | --- | 170 | 3.0 | INS5 HT0 | 0.0 | | |
| 090 | 3 | GLU2 ASP2 VAL | --- | 170 | 3.0 | INS3 HT0 HEP1 | 0.0 | | |
| 091 | 3 | GLU ASP LEU | --- | 170 | 3.0 | INS2 HT1 | 0.0 | | |
| 092 | 3 | GLU ASP THR | --- | 170 | 3.0 | INS2 HT0 | 0.0 | | |
| 093 | 4 | GLU2 ASP2 VAL PRO | --- | 170 | 3.0 | INS2 HT2 | 0.0 | | |
| 094 | 3 | GLU ASP CYS-H | --- | 170 | 3.0 | INS1 HT1 | 0.0 | | |
| 095 | 4 | PRO SER THR CYS | --- | 170 | 3.0 | | 0.0 | | |
| 096 | 3 | GLU ASP VAL2 | --- | 170 | 3.0 | INS3 HT0 HEP4 | 0.0 | | |
| 097 | 3 | GLU ASP VAL | --- | 170 | 3.0 | INS2 HT1 | 0.0 | | |
| 098 | 3 | GLU ASP CYS-H | --- | 170 | 3.0 | INS4 HT1 | 0.0 | | |
| 099 | 2 | GLU2 ASP2 EQU | --- | 170 | 3.0 | INS4 | 0.0 | | |
| 186 -cp | 4 | PYGLU ASP TYR PHE | PA | 176 | 4.0 | INS0 HT4 HEP5 | 0.3 | | |
| 199 -cp | 4 | GLU ASP TYR PHE | H2O | 100 | 99.0 | HT0 INS0 HEP0 | 0.0 | | |
| 202A-cp | 4 | GLU2.4 ASP2 VAL2 GLY | --- | 170 | 4.0 | INS3 HT0 | 0.6 | | |
| 202B-cp | 4 | GLU2.4 ASP2 VAL2 GLY | --- | 170 | 4.0 | HT0 INS3 | 0.6 | | |
| 206A-cp | 4 | GLU ASP-TYR PHE | SULFA | 175 | 4.5 | INS4 HT4 HEP3 | 0.6 | | |
| 206B-cp | 4 | GLU ASP_TYR PHE | SULFA | 175 | 4.5 | | 0.6 | | |
| 206C>3K | 4 | GLU ASP-TYR PHE | SULFA | 175 | 4.5 | | 0.6 | | |
| 207A-cp | 4 | GLU ASP-TYR PHE | SULFA | 175 | 10.0 | INS5 HT4 HEP4 | 2.0 | | |
| 207E-cp | 4 | GLU ASP-TYR PHE | SULFA | 175 | 10.0 | HT5 INS4 HEP4 | 2.0 | | |
| 211A-cp | 4 | GLU ASP-VAL LYSFB | SULFA | 190 | 4.3 | INS5 HT5 HEP5 w | 0.3 | | |
| 211E-cp | 4 | GLU ASP-VAL LYSFB | SULFA | 190 | 4.5 | | 0.3 | | |
| 212A-cp | 3 | GLU2-TYR PHE | SULFA | 185 | 5.0 | INS4 HT3 HEP4 | 0.3 | | |
| 212B-cp | 3 | GLU2-TYR PHE | SULFA | 185 | 5.0 | | 0.3 | | |
| 214 -cp | 3 | GLU LYSFB-ARG | SULFA | 180 | 7.0 | INS0 HT0 HEP0 | 0.0 | | |
| 223 -cp | 4 | LYSFB2 ARG2 LEU PGLU | SULFA | 180 | 8.0 | INS0 HT0 HEP2 | 0.3 | | |
| 227A-cp | 2 | VAL2 GLY2 | SULF | 180 | 1.5 | INS0 HT0 HEP0 | 0.1 | | |
| 227B-cp | 2 | VAL2 GLY2 | SULFA | 180 | 1.5 | HT0 INS0 HEP0 | 0.1 | | |
| 228A-cp | 3 | VAL2 GLY2 PGLU | SULF | 180 | 2.5 | INS0 HT0 HEP0 | 0.1 | | |
| 228B-cp | 3 | VAL2 GLY2 PGLU | SULFA | 180 | 2.5 | HT0 INS0 HEP0 | 0.1 | | |
| 248 -cp | 3 | GLU ASP LEU | --- | 190 | 4.0 | INS3 HT0 HEPa | 0.0 | | |
| 265A-cp | 4 | GLU ASP-TYR PHE | SUL | 155 | 4.0 | INS4 HT4 HEP5 | 1.0 | | |
| 265B | 4 | GLU ASP -TYR PHE | SULFOLANE | 155 | 4.0 | | 1.0 | | |
| 265C | | | | | .0 | | .0 | | |
| 296A-cp | 4 | GLU LYSE PHE ASP | SUL-H | 180 | 3.0 | INS4 HT2 HEP0 | 0.6 | | |
| 296B-cp | 4 | GLU LYSE PHE ASP | SUL-H | 180 | 3.0 | | 0.6 | | |
| 298 -cp | 4 | GLU ASP-TYR PHE | SUL-H | 190 | 1.5 | INS1a HT3 HEP4 | 0.5 | | |
| 301 -cp | 4 | GLU ASP-TYR PHE | SUL | 175 | 8.0 | INS4 HT2 HEP3 | 2.0 | | |
| 302 -cp | 4 | GLU ASP-TYR PHE | HHePO | 190 | 1.5 | INS4 HT2 HEP3 | 0.3 | | |
| 308 -cp | 4 | GLU ASP TYR PHE | HHP | 170 | 1.0 | INS4 HT4 HEP4 | 0.3 | | |
| 309 -CP | 4 | -GLU1.3 ASP1.3 TYR PHE1.3 | SULFOLANE | 190 | 1.5 | INS4aHT3oaHEP4a | 0.3 | | |
| 310 -cp | 4 | -GLU ASP TYR PHE | SULFALANE | 190 | 4.0 | INS4 HT2 HEP5 | 1.0 | | |

Glossary: a=amorphous   o=oil   * =varying temperature   + =cook time change page 46 of 222

PROTEINOID BATCHES   Appendix A

| Bt. No. | #AA | COMPOSITION | ADDITIVE | TEMP C | TIME (hr) | SPHERE RATING | BATCH SIZE molar | Operator | Date |
|---|---|---|---|---|---|---|---|---|---|
| 038 | 2 | GLU2 ASP2 EQU | --- | 150 | 1.5 | | 0.0 | | |
| 039 | 3 | ASP2 ARG ILEU | --- | 170 | 0.0 | HT0 | 0.0 | | |
| 040 | 2 | GLU2 ASP2 EQU | --- | 175 | 3.0 | | 0.0 | | |
| 041 | 2 | GLU2 ASP2 EQU | PA | 170 | 3.0 | | 0.0 | | |
| 042 | 2 | GLU2 ASP2 EQU | GLYC | 170 | 3.0 | HT0 | 0.0 | | |
| 043 | 2 | GLU2 ASP2 EQU | GLYC | 170 | 3.0 | INS4 HT4 | 0.0 | | |
| 044 | 2 | GLU2 ASP2 EQU | GLYC | 170 | 3.0 | HT0 | 0.0 | | |
| 045 | 2 | GLU2 ASP2 EQU | PA | 170 | 3.0 | HT1 | 0.0 | | |
| 046 | 2 | GLU2 ASP2 EQU | GLYC | 190 | 6.0 | HT0 | 0.0 | | |
| 047 | 2 | GLU2 ASP2 EQU | PA | 190 | 6.0 | HT0 | 0.0 | | |
| 048 | 2 | GLU2 ASP2 EQU | --- | 190 | 6.0 | HT0 | 0.0 | | |
| 049 | 2 | GLU2 ASP2 EQU | --- | 190 | 3.0 | HT0 | 0.0 | | |
| 050 | 2 | GLU2 ASP2 EQU | --- | 170 | 3.0 | HT0 | 0.0 | | |
| 051 | 2 | GLU2 ASP2 EQU | --- | 170 | 6.0 | | 0.0 | | |
| 052 | 2 | GLU2 ASP2 EQU | --- | 170 | 6.0 | HT0 | 0.0 | | |
| 053 | 2 | GLU2 ASP2 EQU | --- | 170 | 4.0 | INS0 HT0 | 0.0 | | |
| 054 | 2 | GLU2 ASP2 EQU | --- | 200 | 3.5 | INS4 HT0 | 0.0 | | |
| 055 | 2 | GLU2 ASP2 EQU | --- | 150 | 3.5 | HT-VERY SM | 0.0 | | |
| 056 | 2 | GLU2 ASP2 EQU | --- | 110 | 4.3 | HT0 | 0.0 | | |
| 057 | 2 | GLU2 ASP2 EQU | --- | 150 | 3.5 | HT0 | 0.0 | | |
| 058 | 2 | GLU2 ASP2 EQU | --- | 180 | 5.0 | | 0.0 | | |
| 059 | 2 | GLU2 ASP2 EQU | --- | 150 | 3.0 | INS0 HT0 | 0.0 | | |
| 060 | 2 | GLU2 ASP2 EQU | --- | 160 | 3.0 | HT3 | 0.0 | | |
| 061 | 2 | GLU2 ASP2 EQU | --- | 165 | 3.0 | HT & NO AM | 0.0 | | |
| 062 | 2 | GLU2 LEU | --- | 170 | 3.0 | HT0 | 0.0 | | |
| 063 | 2 | GLU2 ASP2 EQU | --- | 170 | 3.0 | | 0.0 | | |
| 064 | 2 | GLU2 LEU | --- | 170 | 3.0 | INS2 HT0 | 0.0 | | |
| 065 | 3 | GLU2 ASP2 LEU | --- | 170 | 3.0 | INS5 HEPO E | 0.0 | | |
| 066 | 2 | GLU2 GLY | --- | 170 | 3.0 | HT0 | 0.0 | | |
| 067 | 2 | ASP2 LEU | --- | 165 | 3.0 | | 0.0 | | |
| 068 | 2 | ASP2 LEU | --- | | 0.0 | | 0.0 | | |
| 069 | 2 | GLU2 ASP2 EQU | --- | 170 | 3.0 | INS5 & AMORPHOU | 0.0 | | |
| 070 | 3 | GLU2 ASP2 LEU | --- | 170 | 6.0 | HE | 0.0 | | |
| 071 | 3 | GLU ASP3 LEU | --- | 170 | 2.6 | | 0.0 | | |
| 072 | 2 | GLU2 ASP2 EQU | --- | 170 | 3.0 | INS0 HT0 | 0.0 | | |
| 073 | 3 | GLU ASP PRO | --- | 170 | 4.0 | INS0 HT0 HEPO | 0.3 | | |
| 074 | 2 | GLU2 ASP2 EQU | --- | 170 | 3.0 | INS5 | 0.0 | | |
| 076 | 2 | GLU2 ASP2 EQU | --- | 170 | 3.0 | HT3 NO AMO | 0.0 | | |
| 077 | 2 | GLU2 ASP2 EQU | --- | 170 | 4.5 | INS5 | 0.0 | | |
| 078 | 2 | GLU2 ASP2 EQU | --- | 170 | 4.0 | INS5 | 0.0 | | |
| 079 | 4 | GLU ASP PRO LYS3 | --- | 170 | 4.5 | LOST BATCH | 0.0 | | |
| 080 | 3 | GLU2 ASP2 ILEU | --- | 170 | 4.0 | INS4 HT0 HEPO | 0.0 | | |
| 081 | 2 | ARG LYS EQU | --- | 170 | 3.0 | | 0.0 | | |
| 082 | 2 | GLU2 ASP2 EQU | --- | 170 | 4.0 | INS4 HT3 | 0.0 | | |
| 083 | 3 | GLU2 ASP2 ILEU | --- | 170 | 6.0 | INS4 HT1 HEP4 | 0.0 | | |
| 084 | 3 | GLU2 ASP2 ILEU | --- | 170 | 3.0 | INS4 HT3 | 0.0 | | |

Glossary: a=amorphous   o=oil   * =varying temperature   + =cook time change

Appendix A
Page 3 of 9

PROTEINOID BATCHES

| Bt. No. | /AA | COMPOSITION | ADDITIVE | TEMP C | TIME (hr) | SPHERE RATING | BATCH SIZE molar | Operator |
|---|---|---|---|---|---|---|---|---|
| 311 -cp | 4 | -GLU2 LYSB2 PHE2 ASP | SULFALANE | 190 | 1.7 | INS4o HT3o HEP3 | 1.7 | |
| 312 -cp | 4 | -GLU2 LYSB2 PHE2 ASP | SULFALANE | 190 | 0.7 | INS4 HT2 HEP4a | 17.9 | |
| 313 -cp | 4 | -GLU2 LYSB2 PHE2 ASP | SULFALANE | 180 | 3.0 | INS3 HT3 HEP3ao | 0.6 | |
| 314 -cp | 4 | -ASP TYR PHE PGLU | SOLFOLANE | 190 | 2.5 | INS2a HT4aHEP4a | 0.6 | |
| 315 -cp | 4 | GLU ASP-VAL LYSFB | sulfolane | 190 | 4.0 | INS4 HT4 HEP3 | 0.3 | |
| 316 -cp | 4 | GLU ASP-TYR PHE | sulfolane | 180 | 21.0 | INS4 HT3a HEPa | 0.3 | |
| 317 -CP | 4 | GLN-ASP TYR PHE | SULFALANE | 175 | 4.0 | INS5 HT5 HEP5 | 0.3 | |
| 318 -cp | 5 | GLU2 ASP2 TYR2 PHE2 ORN | sulfalane | 180* | .0 | HT1 INS4 HEP3a | 1.0 | |
| 319 -cp | 4 | -TYR PHE ASP PGLU | SULFALANE | 190 | 2.5 | INS4aHT4 HEP4a | 0.3 | |
| 320 -CP | 4 | -TYR PHE PGLU ASP | Sulfolane | 190 | 1.5 | INS4aHT4 HEP4 | 0.3 | |
| 321 -cp | 5 | GLU2 ASP2 TYR2 PHE2 ORN | SULFOLANE | 180* | 3.0 | INS3aHT2aHEP4a | 1.0 | |
| 322 -cp | 4 | GLU2 LYSB2 PHE2 ASP- | SULFOLANE | 192 | 1.2 | INS2 HT2 HEP2 | 0.6 | |
| 323 -cp | 4 | GLU ASP TYR PHE- | SULFOLANE | 190 | .0 | ABORT | 16.0 | |
| 324 -cp | 4 | -GLU ASP TYR PHE | SULFOLANE | 190 | 3.0 | INS4 HT4 HEP5a | 2.0 | |
| 325 -cp | 5 | GLU2 ASP2 TYR2 PHE2 ORN | SULFOLANE | 180* | 3.0 | INS5a HT2a HEP | 1.0 | |
| 326 -CP | 4 | -GLU ASP TYR PHE | SULFOLANE | 190 | 6.5 | INS3a HT0a HEP3 | 16.0 | |
| 326.-CP | 4 | -GLU ASP TYR PHE | SOLFOLANE | | .0 | INS4a HT4 HEP4a | .0 | |
| 327 -CP | 4 | -GLU ASP TYR PHE | SULFOLANE | 190 | 4.0 | INS4a HT5a HEP3 | 17.0 | |
| 328 -CP | 4 | -GLU ASP TYR PHE | SULFOLANE | 190 | 3.0 | INS5a HT3aHEP3a | 17.0 | |
| 328 -7e | 4 | -GLU ASP TYR PHE | SULFOLANE | | .0 | INS3a HT0a HEP4 | .0 | |
| 329 -cp | 4 | -GLN ASP TYR PHE | SULFOLANE | 175 | 6.5 | INS5a HT3a HEP5 | 1.0 | |
| 330 -cp | 2 | ASP PHE | SULFOLANE | 180 | 3.0 | INS0a HT1a HEP0 | 0.5 | |
| 331 -CP | 2 | ASP2 PHE | SULFOLANE | 180 | 3.0 | INS0a HT0a HEP0 | 0.5 | |
| 332 332 | 2 | ASP3 PHE | SULFOLANE | 180 | 3.0 | INS3aHT1aHEP0c | 0.5 | |
| 333 -7a | 4 | -GLU ASP TYR PHE | SULFOLANE | 190 | 5.0 | INS2aHT4a HEP5a | 17.0 | |
| 334 -7ov | 4 | -GLU ASP TYR PHE | SULFOLANE | 190 | 5.0 | INS4aHT5a HEP4a | 17.0 | |
| 335 -CP | 2 | -ASP PHE2 | SULFOLANE | 180 | 3.0 | INS1aHT2aHEP1a | 0.5 | |
| 336 -11 | 5 | -GLU2 ASP2 TYR2 PHE2 ORN | SULFOLANE | 180 | .0 | INS3a HT3a HEP4 | 2.0 | |
| 337 337 | 2 | -ASP2 TYR | SULFOLANE | 180 | 6.5 | INS2aHT0cHEP0c | 0.5 | |
| 338 -CP | 2 | -ASP TYR | SULFOLANE | 180 | 3.0 | INS0 HT0 HEP0 | 1.0 | |
| 339 -CP | 2 | -ASP3 TYR | SULFOLANE | 180 | 3.0 | INS0a HT0 HEP0 | 0.5 | |
| 340 | 4 | -GLU ASP TYR PHE | SOLFOLANE | | .0 | | 1.5 | |
| 341 | 4 | -GLU ASP TYR PHE | SOLFOLANE | | .0 | | 17.0 | |
| 342 342 | 2 | -ASP TYR2 | SOLFOLANE | | .0 | INS0HT0HEP0 | 0.5 | |
| 342 -CP | 2 | -ASP TYR2 | SOLFOLANE | | .0 | INS0a HT0 HEP0 | 0.5 | |
| 343 | 4 | -GLU ASP TYR PHE | SOLFOLANE | | .0 | | 17.0 | |
| 344 | 4 | -GLU ASP TYR PHE | SOLFOLANE | | .0 | | 2.0 | |
| 345 -CP | 2 | - ASP2 PHE | SOLFOLANE | | .0 | INS0a HT0 HEP0 | .0 | |
| 346 -CP | 4 | -GLN ASP TYR PHE | SOLFOLANE | | .0 | INS0aHT1aHEP2A | .0 | |
| 347 | 4 | - GLU2 ASP2 TYR5 PHE5 | SOLFOLANE | | .0 | | .0 | |
| 348 | 2 | -ASP2 PHE | SULFOLANE | | .0 | | .0 | |
| 349 | 2 | -PHE ASP2 | SULFOLANE | | .0 | | .0 | |
| 350 | 2 | -ASP2 PHE | SULFOLANE | | .0 | | .0 | |
| 351 351 | 3 | -GLU2 TYR PHE | SULFOLANE | | .0 | INS3aHT2aHEP3a | .0 | |
| 352 | 5 | -GLU2 ASP2 TYR2 PHE2 ORN | SULFOLANE | | .0 | | .0 | |
| 353 | 5 | -GLU2 ASP2 TYR2 PHE2 ORN | SULFOLANE | | .0 | | .0 | |

Glossary: a=amorphous    o=oil    * =varying temperature    + =cook time change

PROTEINOID BATCHES

Appendix A
page 4 of 9

| Bt. No. | #AA | COMPOSITION | ADDITIVE | TEMP C | TIME (hr) | SPHERE RATING | BATCH SIZE molar | |
|---|---|---|---|---|---|---|---|---|
| 295 -cp | 1 | ASP | SUL-H | 180 | 1.5 | INS2aHT2aHEP3oa | 0.3 | |
| 297 -cp | 4 | GLU ASP-TYR PHE | SUL-H | 190 | 1.5 | INS2a HT4a HEP3 | 0.5 | |
| 299 -cp | 4 | GLU LYS PHE ASP | SUL-H | 190 | 1.7 | INS5 HT4 HEP2 | 0.6 | |
| 300 -cp | 5 | GLU ORN ASP LYS PHE | --- | 180 | 3.0 | INS3 HT3 HEP3 | 0.3 | |
| 303 -cp | 4 | GLU ASP-TYR PHE | SUL-H | 175 | 8.0 | INS4 HT2 HEP3a | 2.0 | |
| 304 -cp | 5 | GLU ASP-TYR PHE ORN0.5 | SUL-H | 180 | 3.0 | INS4 HT2 HEP3 | 2.0 | |
| 305 | 4 | -PGLU ASP.5TYR PHE | SUL | | 0.0 | INS3 HT2 HEP3 | 0.3 | |
| 306 -cp | 4 | -GLU ASP .5TYR PHE | SUL | | 0.0 | INS3aHT2aHEP2a | 0.3 | |
| 307 -cp | 4 | GLN ASP TYR PHE | SULFOLANE | 175 | 4.0 | INS4o HT4 HEP4o | 0.3 | 1 |
| - | | | | | .0 | | .0 | |
| 000 | | | | | .0 | | .0 | |
| 001 | 2 | GLU2 ASP2 EQU | --- | 170 | 4.0 | | 0.0 | |
| 002 | 2 | GLU ASP EQU | --- | 149 | 0.0 | | 0.0 | |
| 003 | 2 | GLU ASP EQU | --- | 163 | 0.0 | | 0.0 | |
| 004 | 0 | | --- | 204 | 0.0 | | 0.0 | |
| 005 | 2 | GLU ASP EQU | --- | 176 | 3.0 | | 0.0 | |
| 006 | 2 | GLU ASP EQU | --- | 154 | 3.0 | | 0.0 | |
| 007 | 2 | GLU ASP EQU | --- | 196 | 2.0 | | 0.0 | |
| 008 | 2 | GLU ASP EQU | --- | 154 | 3.6 | | 0.0 | |
| 009 | 2 | GLU2 ASP2 EQU | --- | 192 | 3.0 | | 0.0 | |
| 010 | 2 | GLU2 ASP2 EQU | --- | 163 | 4.0 | | 0.0 | |
| 011 | 2 | GLU2 ASP2 EQU | --- | 160 | 5.0 | | 0.0 | |
| 012 | 2 | GLU2 ASP2 EQU | --- | 154 | 4.0 | | 0.0 | |
| 013 | 2 | GLU2 ASP2 EQU | --- | 176 | 4.0 | | 0.0 | |
| 014 | 2 | GLU2 ASP2 EQU | --- | 174 | 3.5 | | 0.0 | |
| 016 | 2 | GLU2 ASP2 EQU | --- | 170 | 3.5 | | 0.0 | |
| 017 | 2 | GLU2 ASP2 EQU | --- | 170 | 3.5 | | 0.0 | |
| 018 | 2 | GLU2 ASP2 EQU | --- | 170 | 3.5 | | 0.0 | |
| 019 | 2 | GLU ASP EQU | --- | 180 | 3.5 | | 0.0 | |
| 020 | 2 | GLU2 ASP2 EQU | --- | 180 | 4.5 | HT | 0.0 | |
| 021 | 2 | GLU2 ASP2 EQU | --- | 180 | 3.5 | | 0.0 | |
| 022 | 2 | GLU2 ASP2 EQU | --- | 180 | 3.5 | | 0.0 | |
| 023 | 2 | GLU2 ASP2 EQU | --- | 180 | 3.3 | | 0.0 | |
| 024 | 2 | GLU2 ASP2 EQU | --- | 175 | 3.3 | | 0.0 | |
| 025 | 2 | GLU2 ASP2 EQU | --- | 175 | 3.0 | | 0.0 | |
| 026 | 3 | GLU2 ASP2 ASPG | --- | 175 | 3.0 | | 0.0 | |
| 027 | 3 | GLU2 ASP2 SER | --- | 195 | 5.0 | | 0.0 | |
| 028 | 2 | GLU2 ASP2 EQU | --- | 175 | 3.5 | | 0.0 | |
| 029 | 2 | GLU2 ASP2 EQU | --- | 175 | 3.5 | | 0.0 | |
| 031 | 2 | GLU2 ASP2 EQU | --- | 170 | 3.3 | | 0.0 | |
| 032 | 2 | GLU2 ASP2 EQU | --- | 170 | 3.5 | HTO | 0.0 | |
| 033 | 2 | GLU2 ASP2 EQU | --- | 175 | 3.0 | HTO | 0.0 | |
| 034 | 2 | GLU2 ASP2 EQU | --- | 180 | 0.0 | HTO | 0.0 | |
| 035 | 2 | GLU2 ASP2 EQU | --- | | 3.0 | HTO | 0.0 | |
| 036 | 2 | GLU2 ASP2 EQU | --- | 175 | 3.6 | HTO | 0.0 | |
| 037 | 2 | GLU2 ASP2 EQU | --- | 175 | 21.0 | | 0.0 | |

Glossary: a=amorphous   o=oil   * =varying temperature   + =cook time change

PROTEINOID BATCHES

Appendix A
page 5 of 9

| Bt. No. | #AA | COMPOSITION | ADDITIVE | TEMP C | TIME (hr) | SPHERE RATING | BATCH SIZE molar |
|---|---|---|---|---|---|---|---|
| 249 <3K | 4 | GLU2LEU2LYS2PGLU | --- | 180 | 3.0 | INS0 MT0 HEP0 | 0.1 |
| 250 <3K | 5 | PGLUARGH2LYS2LEUASP2 | --- | 180 | 3.0 | INS0 MT0 HEP0 | 0.1 |
| 251 <3K | 4 | GLU2ASP2TYR5-PHE5 | SUL-H | 180 | 3.0 | INS4 MT4 HEP2 | 0.1 |
| 252 -cp | 4 | (GLU+ASP)VAL LYS | --- | 170 | 3.0 | INS1 MT2 HEP1 | 0.0 |
| 253 -cp | 4 | GLU ASP-TYR PHE | SUL-H | 180 | 4.5 | INS1 MT0 HEP0 | 2.0 |
| 253 | 4 | GLU ASP-TYR PHE | SUL-H | 180 | 10.0 | INS4 MT4 HEP4 | 1.0 |
| 254 -cp | 5 | GLU2ASP2-TYR2PHE2ORN | SUL-H | 180 | 8.5 | INS4 MT4 HEP4 | 0.1 |
| 255 -cp | 5 | GLU ASPTYR-PHE ORN | SUL-H | 180 | 3.0 | INS2 MT4 HEP4 | 0.3 |
| 256 -cp | 4 | GLU2LYS2PHE2PGLU | --- | 180 | 3.0 | INS0 MT0 HEP0 | 0.1 |
| 257 -cp | 4 | GLU ASP ARGH ORNH | --- | 180 | 3.0 | INS0 MT0 HEP0 | 0.0 |
| 258 <3K | 3 | GLU ASP ARGH | --- | 180 | 3.0 | INS1 MT1 HEP0 | 0.0 |
| 259 <3K | 4 | GLU ASP-TYR PHE | SUL-H | 180 | 3.0 | INS3 MT3 HEP3 | 0.3 |
| 260 <3K | 4 | GLU ASP-TYR PHE | SUL-H | 180 | 2.5 | INS2 MT3 HEP2 | 0.3 |
| 261 -cp | 4 | GLU ASP-TYR PHE | SUL-H | 180 | 3.0 | INS0 MT0 HEP0 | 0.3 |
| 262 -cp | 4 | GLU LORN ASP LYSFB | SUL-H | 180 | 3.5 | INS0 MT1 HEP4 | 0.3 |
| 263 -cp | 4 | GLU2 LYS2 PHE2 ASP | --- | 190 | 3.0 | INS3 MT3 HEP0 | 0.3 |
| 264 -cp | 4 | GLU2 LYS2 PHE2 ASP | --- | 180 | 3.2 | INS5 MT3 HEP4 | 0.3 |
| 266 -cp | 4 | GLU2 LYS2 PHE2 ASP | --- | 180 | 3.0 | INS4 MT4 HEP4 | 0.3 |
| 267 -cp | 3 | GLU LYSFB ASP LYSFB | SUL-H | 180* | 3.0 | INSa MTc HEPc | 0.3 |
| 268 | 4 | GLU ASP-TYR PHE | SUL-H | 190 | 2.5 | INS0 MT0 HEP0 | 0.3 |
| 269 -cp | 4 | GLU ORNH ASP-LYSFB | SUL-H | 180 | 4.0 | INSc MTc HEPc | 0.1 |
| 270 -cp | 4 | GLU ASP-TYR PHE | SUL-H | 180 | 1.5 | INS5 MT4 HEP0 | 1.5 |
| 271 | 3 | GLU LYSFB-PHE | SUL-H | 190 | 1.5 | INS3aMT4oHEP4o | 0.0 |
| 272 -cp | 4 | GLU2 LEU2 LYS2 TYR1 | --- | 180 | 3.0 | INSc MT1 HEP4 | 0.1 |
| 273 -cp | 4 | GLU2 LEU2 LYS2 PHE1 | --- | 180 | 3.0 | INS2aMT2 HEP2,a | 0.1 |
| 274 -cp | 4 | GLU LEU ARG TYR | --- | 180 | 3.0 | INSc MTc HEPc | 0.1 |
| 275 -cp | 4 | GLU ARGH-TYR | SUL | 190 | 1.5 | INSc MTc HEPc | 0.3 |
| 276 -cp | 4 | GLU2 LEU2 ARG2 PHE | --- | 180 | 3.0 | INS3 MT3 HEP4 | 0.1 |
| 277 -cp | 3 | GLU LYS TYR | SUL-H | 190 | 1.5 | INSc MTc HEP4o | 0.3 |
| 278 -cp | 3 | GLU LYS PHE | SUL-H | 190 | 1.5 | INSc MTc HEP4 | 0.3 |
| 279 -cp | 3 | GLU LYS ALA | --- | 190 | 1.5 | INSc MTc HEPc | 0.3 |
| 280 -cp | 4 | GLUGLUASPGLUTYRGLPHE | SUL-H | 190 | 1.5 | INS4 MT3 HEP4 | 0.4 |
| 281 -cp | 4 | GLU1 ASP1 TYR2.5-PHE2.5 | SUL-H | 180 | 3.0 | INS4 MTa HEP2a | 1.0 |
| 282 -cp | 3 | GLU2 LYS5 PHE2 | --- | 190 | 1.5 | INS0 MT0 HEP2 | 0.3 |
| 283 -cp | 4 | GLU2 LYS5 PHE5 TYR2 | --- | 190 | 1.5 | INS0 MT0 HEP3 | 0.1 |
| 284 | 5 | GLU2ASP2-TYR2PHE2ORN | SUL-H | 180 | 3.0 | INS4aMT4oHEP2a | 1.0 |
| 285 -cp | 2 | GLU(2X) ASP(2X) | --- | 180 | 3.0 | INSc MTc HEPc | 0.3 |
| 286 -cp | 2 | GLU ASP(2X) | --- | 180 | 2.5 | INSc MTc HEPc | 0.3 |
| 287 -cp | 2 | GLU PHE | --- | 180 | 3.5 | INS3 MT2 HEP3 | 0.3 |
| 288 -cp | 3 | GLU ORN PHE | --- | 180 | 3.0 | INSc MTc HEPc | 0.3 |
| 289 | 2 | GLU ARG | --- | 180 | 1.0 | | 0.3 |
| 290 -cp | 3 | GLU ARG PHE | --- | 180 | 3.0 | INS2 MT2 HEP2 | 0.3 |
| 291 -CP | 3 | GLU LYS PHE | SUL-H | 190 | 1.5 | INS4 MT3o HEP4o | 0.3 |
| 292 -cp | 5 | GLU ASP ARG ORN PHE | SUL-H | 180 | 3.0 | INS0 MT0 HEP0 | 0.3 |
| 293 -cp | 4 | GLU ASP ARG ORN PHE | SUL-H | 180 | 3.0 | INS3 MT3 HEP3 | 0.3 |
| 294 -cp | 4 | GLU2 LYS2 PHE2 ASP | --- | 180 | 3.0 | INS3 MT4 HEP4 | 0.3 |

Glossary: a=amorphous   o=oil   * =varying temperature   + =cook time change

PROTEINOID BATCHES

| Bt. No. | #AA | COMPOSITION | ADDITIVE | TEMP C | TIME (hr) | SPHERE RATING | BATCH SIZE molar |
|---|---|---|---|---|---|---|---|
| 192 -cp | 3 | GLU LYSFB ASP | --- | 195 | 3.0 | INS4 HTO | 0.3 |
| 193 >6K | 4 | (GLU+ASP) TYR PHE | PA | 175 | 4.0 | HTO HEP0 | 0.3 |
| 194 -cp | 3 | GLU LYSFB ASP | TRIGL | 195 | 3.0 | INS1 HTO HEP2 | 0.3 |
| 195 -cp | 3 | GLU ASP VAL2 | --- | 170 | 3.2 | INS2 HT1 HEP0 | 0.3 |
| 196 -cp | 4 | GLU ASP TYR PHE | PA | 175 | 4.2 | INS2 HT5 HEP4 | 1.0 |
| 197 -cp | 4 | GLU ASP TYR PHE | SUL | 175 | 2.7 | INS2 HT5 HEP5 | 0.3 |
| 198 -cp | 3 | GLU LYSFB ASP | --- | 195 | 3.2 | INS3 | 1.0 |
| 200 -cp | 3 | GLU LYSH ASP | PA | 185 | 3.0 | INS4 HTO HEP0 | 0.3 |
| 201 -cp | 3 | GLU LYSFB ASP | SULFA | 195 | 3.0 | INS4 HTO HEP3 | 0.3 |
| 203 -cp | 4 | GLU ASP VAL LYS | --- | 170 | 3.0 | INS5 HT5 HEP | 0.3 |
| 204 -cp | 3 | GLU LYS ASP | --- | 185 | 3.0 | INS4 HTO HEP0 | 0.3 |
| 205 -cp | 4 | GLU ASP-TYR PHE | SULFA | 175 | 3.7 | INS4 HTO | 0.6 |
| 208 | 3 | GLUH LYSH ASPH | NaHCO&MeOH | 80 | 8.0 | INS0 HTO HEP0 | 0.0 |
| 209 -cp | 4 | GLU ASP-VAL LYS | SULFA | 170 | 3.2 | INS4 HT4 HEP3 W | 0.3 |
| 210 -cp | 4 | GLU ASP-VAL LYSFB | SULFA | 170 | 3.0 | INS4 HT4 HEP3 | 2.0 |
| 213 -cp | 3 | GLU-LYS HIS | SULFA | 180 | 3.0 | INS0 HTO HEP0 | 0.3 |
| 215 -cp | 3 | GLU ASP GLY2 | --- | 180 | 5.5 | INS3 HTO HEP0 | 0.3 |
| 216 -cp | 4 | GLU ASP-TYR PHE | SULFA | 175 | 3.0 | INS4 HT4 HEP4 | 2.0 |
| 217 | 3 | GLUASPLYS(DIETESTER) | MEOH/Et3N | 75 | 29.0 | | 0.0 |
| 218 -cp | 4 | GLU ASP-TYR PHE | SULFA | 175 | .0 | INS0 HTO HEP0 A | 0.3 |
| 219 -cp | 3 | GLU-LYS-LEU | sul/POCl3 | 180* | 8.5 | INS2 HTO HEP2 | 0.3 |
| 220 -cp | 4 | GLU ASP-TYR PHE | SULFA | 180 | 20.5 | INS4 HT4 HEP5 | 0.3 |
| 221 -cp | 3 | -ASP2 TYR PHE | SULFA | 180 | 22.0 | INS2 HTO HEP0 | 0.3 |
| 222 -cp | 3 | -LYSFB2 ARG2 LEU | SULFA | 180 | 4.0 | INS0 HTO HEP2 | 0.3 |
| 224 -cp | 4 | GLU ASP-TYR PHE- | SU/PA | 180 | 6.0 | INS3 HTO HEP0 | 0.3 |
| 225 -cp | 3 | PRO-SER TYR | SULF | 180 | 3.5 | INS2 HTO HEP0 | 0.3 |
| 226 <3K | 4 | GLU ASP TYR PHE | SULF | 180 | 4.0 | INS3 HT4 HEP3 | 0.3 |
| 229 <3K | 4 | -GLU ASP TYR PHE | SULF | 180 | 5.5 | INS3 HTO HEP0 | 0.3 |
| 230 -cp | 2 | GLU TYR | --- | 180 | 4.0 | INS4 HTO HEP0 | 0.3 |
| 231 -cp | 3 | GLU LYSFB PHE | SULF | 180 | 3.5 | INS2 HTO HEP0 | 0.3 |
| 232 -cp | 3 | GLU LEU ARG | --- | 180 | 4.0 | INS0 HTO HEP0 | 0.3 |
| 233 -cp | 3 | GLU LEU LYSH | --- | 180 | 4.0 | INS0 HTO HEP0 | 0.3 |
| 234 -cp | 4 | -(GLU ASP TYR PHE) | SULF | 150 | 27.0 | INS3 HTO HEP0 | 0.3 |
| 235 -cp | 4 | -(GLU ASP)TYR10PHE10 | SULF | 180 | 22.0 | INS0 HTO HEP0 | 0.0 |
| 236 -cp | 3 | GLU TYR LYSHCL | --- | 180 | 2.0 | INS0 HTO HEP0 | 0.3 |
| 237 <3K | 4 | GLU2 LEU2 LYSE2 ASP | --- | 180 | 3.0 | INS0 HTO HEP0 | 0.1 |
| 238 <3K | 4 | GLU ASP TYR5 PHE5 | SULF | 180 | 3.0 | INS0 HTO HEP0 | 0.1 |
| 239 -cp | 3 | -GLU ASP LEU | SUL-H | 190 | 1.0 | INS3 HTO HEP0 | 0.0 |
| 240 -cp | 3 | -(GLU ASP) LEU | SUL-H | 170 | 4.0 | INS4 HTO HEP0 | 0.0 |
| 241 <3K | 3 | -(GLU ASP) LEU | SUL-H | 190 | 5.0 | INS3 HTO HEP0 | 0.0 |
| 242 -cp | 3 | (GLU ASP LEU) | SUL-H | 170 | 2.5 | INS0 HtO HEP0 | 0.0 |
| 243 -cp | 5 | PGLU2ASPARG2LYS2LEU | --- | 180 | 3.0 | INS0 HTO HEP0 | 0.1 |
| 244 -cp | 3 | (GLU ASP) LEU | --- | 190 | 2.5 | INS0 HTO HEP0 | 0.0 |
| 245 -cp | 3 | (GLU ASP) LEU | --- | 170 | 1.0 | INS3 HT1 HEP0 | 0.0 |
| 246 <3K | 5 | GLU2 LYSH2 PHE2 ASP | --- | 180 | 6.0 | INS4 HT4 HEP4 | 0.0 |
| 247 -cp | 3 | GLU ASP LEU | --- | 170 | 5.0 | INS0 HTO HEP0 | 0.0 |

Glossary: a=amorphous   o=oil   * =varying temperature   + =cook time change

Appendix A
Page 7 of 9

PROTEINOID BATCHES

| Bt. No. | #AA | COMPOSITION | ADDITIVE | TEMP C | TIME (hr) | SPHERE RATING | BATCH SIZE molar | Operator | Date |
|---|---|---|---|---|---|---|---|---|---|
| 145 | 3 | GLU ASP LYSFB | PPA | 185 | 6.0 | MT0 | 0.0 | | |
| 146 | 3 | GLU ASP VAL2 | PPA | 170 | 3.5 | INS2 MT0 | 0.0 | | |
| 147 | 4 | GLU ASP PHE ALA | --- | 170 | 3.0 | INS4 MT3 HEP4 | 0.0 | | |
| 148 | 4 | GLU ASP TYR PHE | PA | 170 | 3.0 | MT0 HEP4 | 0.0 | | |
| 149 | 3 | GLU ASP PHE2 | --- | 170 | 3.0 | | 0.0 | | |
| 150 | 4 | GLU ASP LEU PHE | PA | 170 | 24.0 | MT0 HEP0 | 0.0 | | |
| 151 | 4 | GLU ASP TYR PHE | PA | 170 | 6.0 | INS4 MT4 HEP4 | 0.0 | | |
| 152 | 4 | GLU ASP TYR PHE | PA | 170 | 5.0 | | 0.0 | | |
| 153 | 3 | GLU LYSFB PHE | PA | 170 | 24.0 | | 0.0 | | |
| 154 | 4 | GLU ASP TYR PHE | PA | 170 | 4.0 | | 0.0 | | |
| 155 | 3 | GLU2 TYR PHE | PA | 170 | 4.0 | INS4 MT5 HEP3 | 0.0 | | |
| 156 | 3 | GLU4 LYS2 PHE | --- | 170 | 6.0 | INS0 MT0 HEPc | 0.0 | | |
| 157 | 3 | GLU2 TYR LEU | PA | 170 | 5.0 | INS2 MT1 HEP0 | 0.0 | | |
| 158 | 3 | GLU2 PHE LEU | PA | 175 | 5.0 | INS4 MT0 HEP4 | 0.0 | | |
| 159 | 3 | GLU3 PHE TYR | PA | 175 | 5.0 | INS4 MT4 HEP4 | 0.0 | | |
| 160 | 4 | GLU6 LYS2 PHE TYR | PA | 170 | 6.0 | INSa MTc HEPc | 0.0 | | |
| 161 | 4 | GLU4 PHE2 TYR2 CYS | PA | 170 | 4.0 | INS4 MT HEP | 0.0 | | |
| 162 | 3 | GLU2 TYR PHE | PA | 170 | 5.5 | INS3 MT0 HEP2 | 0.0 | | |
| 163 | 3 | GLU2 PHE TYR | PA | 170 | 5.0 | INS3 MT2 HEP3 | 0.0 | | |
| 164 | 3 | GLU2 PHE TYR | PA | 170 | 5.0 | INS4 MT4 HEP4 | 0.0 | | |
| 165 | 4 | GLU3 ASP PHE2 TYR2 | PA | 170 | 3.0 | INS3 MT0 HEP0 | 0.0 | | |
| 166 | 3 | GLU LYSFB PGLU | PA | 170 | 7.0 | | 0.0 | | |
| 167 | 4 | GLU ASP TYR PHE | PA | 170 | 6.5 | | 0.0 | | |
| 168 | 3 | GLU ASP LYSFB | PPA | 185* | 72.0 | MT0 | 0.0 | | |
| 169 | 3 | GLU ASP LYSFB | PPA | 185 | 72.0 | MT0 | 0.0 | | |
| 170 | 3 | GLU ASP LYSFB | --- | 195 | 7.0 | MT5 | 0.0 | | |
| 171 | 3 | GLU LSYHCL ASP | M.OIL | 180 | 7.0 | MT0 | 0.0 | | |
| 172 | 4 | GLU ASP TYR PHE | PA | 170 | 6.0 | MT1 | 0.0 | | |
| 173 | 3 | GLU LYS ASP | mineral o. | 185 | 3.0 | ABORT | 0.3 | | |
| 174 >6K | 3 | GLU LYS ASP | GLycerin | 185 | 3.0 | INS2 MT1 HEP3 | 0.3 | | |
| 175 >6K | 4 | GLU ASP TYR PHE | PA | 172 | 3.5 | | 1.0 | | |
| 176 >6K | 3 | GLU2 LYS2 LYS | --- | 180 | 3.0 | INS0 MT0 HEP0 | 0.3 | | |
| 177 >6K | 3 | GLU ARG ASP | --- | 180 | 3.2 | INS0 MT2 HEP0 | 0.3 | | |
| 178 >6K | 3 | GLU LYS ASP | --- | 190 | 3.2 | INS0 MT0 HEP1 | 0.3 | | |
| 179 >6K | 4 | GLU ASP TYR PHE | PA | 175 | 4.0 | | 1.0 | | |
| 180 >6K | 4 | GLU ASP TYR PHE | PA | 175 | 7.0 | See Notes. | 1.0 | | |
| 181 >6K | 3 | GLU LYS ASP | --- | 185 | 3.0 | INS0 MT0 | 0.3 | | |
| 182 >6K | 4 | GLU ASP TYR PHE | PA | 175 | 3.7 | MT1 HEP1 | 0.3 | | |
| 183 | 4 | PGLU ASP TYR PHE | PA | 175 | 4.0 | ABORT-RETRY | 0.3 | | |
| 184 -cp | 4 | GLU ASP TYR PHE | PA | 175 | 3.5 | MT2 HEP4 | 0.3 | | |
| 185 -cp | 4 | GLU ASP TYR PHE | PA | 176 | 4.2 | INS MT4 HEP4 | 1.0 | | |
| 187 | 3 | ASP TYR PHE | PA | 170 | .0 | ABORT | 0.3 | | |
| 188 -cp | 3 | ASP TYR PHE | PA | 150 | 21.2 | INS0 MT0 HEP0 | 0.3 | | |
| 189 -cp | 4 | GLU ASP TYR PHE | PA | 176 | 4.0 | MT4 HEP5 | 1.0 | | |
| 190 -cp | 4 | GLU ASP TYR PHE | PA | 175 | 4.0 | MT5 HEP4 | 1.0 | | |
| 191 -cp | 3 | ASP2 TYR PHE | PA | 150 | 24.0 | MT0 HEP0 | 0.3 | | |

Glossary: a=amorphous    o=oil    * =varying temperature    + =cook time change

PROTEINOID BATCHES

| Bt. No. | #AA | COMPOSITION | ADDITIVE | TEMP C | TIME (hr) | SPHERE RATING | BATCH SIZE molar |
|---|---|---|---|---|---|---|---|
| 015 | 2 | GLU2 ASP2 EQU | --- | 170 | 2.5 | | 0.0 |
| 100 | 3 | GLU ASP VAL2 | --- | 170 | 3.0 | | 0.0 |
| 101 | 3 | GLU ASP VAL2 | --- | 170 | 3.0 | | 0.0 |
| 102 | 3 | GLU ASP VAL2 | --- | 170 | 3.0 | | 0.0 |
| 103 | 4 | GLU ASP GLY VAL | --- | 170 | 3.5 | INS4 | 0.0 |
| 104 | 4 | GLU ASP VAL LEU | --- | 170 | 3.5 | INS4 HT2 HEP5 | 0.0 |
| 105 | 3 | GLU ASP GLY2 | --- | 180 | 4.0 | INS4 HT2 | 0.0 |
| 106 | 4 | GLU ASP VAL LEU | --- | 170 | 5.0 | | 0.0 |
| 107 | 4 | GLU2 ASP2 GLY VAL2 | --- | 170 | 3.0 | INS5 | 0.0 |
| 108 | 4 | GLU2 ASP2 GLY VAL2 | --- | 170 | 4.0 | INS4 NO AMORPHO | 0.0 |
| 109 | 4 | GLU2 ASP2 GLY VAL2 | --- | 170 | 4.0 | INS4 HT1 | 0.0 |
| 110 | 4 | GLU2 ASP2 GLY2 VAL | --- | 170 | 3.5 | | 0.0 |
| 111 | 5 | GLU ASP GLY VAL CYS | --- | 170 | 3.0 | | 0.0 |
| 112 | 4 | GLU ASP GLY PHE | --- | 170 | 4.0 | INS4 HT3 HEP4 | 0.0 |
| 113 | 4 | GLU ASP VAL2 GLY | --- | 170 | 3.0 | INS2 HT0 | 0.0 |
| 114 | 3 | GLU ASP VAL | --- | 170 | 3.0 | INS4 HT0 | 0.0 |
| 115 | 3 | GLU VAL TYR | --- | 170 | 4.0 | | 0.0 |
| 116 | 4 | GLU ASP VAL LYS | --- | 170 | 4.0 | | 0.0 |
| 117 | 3 | GLU VAL TYR | --- | 170 | 3.0 | INS5 | 0.0 |
| 118 | 2 | GLU TYR | --- | 170 | 3.5 | INS5 HT0 HEP0 | 0.0 |
| 119 | 2 | GLU2 ASP2 EQU | --- | 170 | 3.5 | INS5 HT1 | 0.0 |
| 120 | 3 | GLU ASP TYR | --- | 170 | 4.5 | INS0 HT0 HEP0 | 0.0 |
| 121 | 4 | GLU ASP TYR PHE | --- | 170 | 4.0 | INS5 HT3 HEP4 | 0.0 |
| 122 | 4 | GLU ASP VAL TYR | --- | 170 | 3.0 | INS3 HT0 HEP0 | 0.0 |
| 123 | 1 | GLU | --- | 170 | 4.5 | CAN'T DRY | 0.0 |
| 124 | 3 | GLU TYR VAL | --- | 170 | 3.5 | INS4 HT3 HEP3 | 0.0 |
| 125 | 3 | PGLU VAL TYR | --- | 170 | 3.5 | INS3 HT2 | 0.0 |
| 126 | 4 | GLU ASP VAL2 GLY | --- | 170 | 4.0 | INS1 | 0.0 |
| 127 | 4 | GLU2 ASP2 VAL2 PHE | --- | 170 | 4.0 | INS3 HT2 HEP4 | 0.0 |
| 128 | 2 | GLU2 ASP2 EQU | --- | 170 | 3.5 | HT0 | 0.0 |
| 129 | 2 | GLU2 ASP2 EQU | --- | VARY | 4.0 | INS3 HT0 | 0.0 |
| 130 | 2 | GLU2 ASP2 EQU | --- | 220 | 3.0 | INS5 HT0 | 0.0 |
| 131 | 2 | GLU2 LYSFB | --- | 185 | 3.0 | INS1 HT0 | 0.0 |
| 132 | 3 | GLU ASP LYSFB | --- | 185 | 3.0 | INS3 HT2 HEP2 | 0.0 |
| 133 | 3 | GLU ASP LYSFB | PA | 180 | 6.2 | INS5 HT1 HEP2 | 0.0 |
| 134 | 4 | GLU ASP LYS VAL | PA | 185 | 3.0 | | 0.0 |
| 135 | 3 | GLU ASP LYSFB | GLYC | 185 | 6.5 | INS1 HT1 | 0.0 |
| 136 | 2 | GLU2 ASP2 EQU | --- | 155 | 3.0 | HT0 | 0.0 |
| 137 | 5 | GLU2ASP2LEU THY VAL | --- | 185 | 4.0 | INS0 HT0 | 0.0 |
| 138 | 4 | GLU ASP VAL TYR | --- | 185 | 4.5 | INS1 HT3 | 0.0 |
| 139 | 4 | GLU ASP VAL TYR | PPA | 160* | 72.0 | INS2 HT3 | 0.0 |
| 140 | 3 | GLU ASP LYSFB | PPA | 120* | 72.0 | INS5 HT2 HEP4 | 0.0 |
| 141 | 3 | GLU LYSFBSYNPEPagqp | --- | 185 | 6.0 | | 0.0 |
| 142 | 3 | GLU ASP LYSFB | PPA | 120* | 72.0 | INS1 HT1 | 0.0 |
| 143 | 3 | GLU VAL TYR | --- | 170 | 3.0 | INS2 HT2 | 0.0 |
| 144 | 4 | GLU2 ASP2 GLY VAL2 | --- | 170 | 3.0 | INS1 HT1 | 0.0 |

Glossary: a=amorphous   o=oil   * =varying temperature   + =cook time change

Appendix A
page 9 of 9

PROTEINOID BATCHES

| Bt. No. | #AA | COMPOSITION | ADDITIVE | TEMP C | TIME (hr) | SPHERE RATING | BATCH SIZE molar |
|---|---|---|---|---|---|---|---|
| 354 | 5 | -(GLU ASP TYR PHE)2 ORN | SULFOLANE | | | .0 | .0 |

Sphere rating:   0= worst    5= best

INT = insulin
MT  = empty microsphere
HEP = heparin

Glossary: a=amorphous   o=oil   * =varying temperature   + =cook time change

Appendix B
page 1 of 2

IEF TABLES
Proteinoid sorting, pKa and composition
Chemical basis for microsphere ODS

| Material ID No. | Composition ---> (*no asp) | Sphere frac number | Sphere pH range | Sphere IEF rating | Sphere Matrix rating | Max UV Frac.No. | Max UV pH |
|---|---|---|---|---|---|---|---|
| 202B | Glu2.4 Asp2Val2GLy * | no spher | ---- | ---- | INS4 MT0 HEP3 | ---- | ---- |
| 210>1K | Glu Asp Val Lys | 14-20 | 2.3-4.4 | 2-3 | INS4 MT4 HEP3 | 14-19 | 4.4-3.0 |
| 213>1k | Glu LysFB HisFB | 16-19 | 1.7-2.1 | 2 | INS0 MT0 HEP0 | 11-16 | 7.6-2.1 |
| 218<3k | Glu Asp Tyr Phe | 18-20 | 3.2-2.7 | 2 | INS0 MT0 HEP0 | 1-7 | 12.2-9.3 |
| 129 | Glu Asp Equ | 10-18 | 2.5-4.4 | 3 | INS3 MT0 | 15-18 | 2.9-2.5 |
| 214>1k | Glu LysFB Arg | no spher | ---- | ---- | INS0 MT0 HEP0 | 1-4 | 11.8-9.2 |
| 176 | Glu2 LysFB2 LysFB | no spher | ---- | ---- | INS0 MT0 HEP0 | 5-6 | 9-8.6 |
| 222-cp | Arg2 LysFB2 Leu | ?1-4? | 9.9-11.7 | 2? | INS0 MT0 HEP2 | 2-6 | 8.5-11.5 |
| 202B | Glu2.4 Asp2 Val2 Gly | 8-12 | 3.3-5 | 2,1-2 | INS4 MT0 HEP3 | 8-12 | 5-3.3 |
| 223-cp | Arg2 LysFB2 Leu pGlu | 1 | 10.3 | 2-3 | INS0 MT0 HEP2 | 1 | 10.3 |
| 223-cp | Arg2 LysFB2 Leu pGlu | 1-5 | 9.0-12 | 2 | INS0 MT0 HEP2 | 3 | 10.7 |
| 170a | Glu Asp LysFB | 16-20 | 2.3-5.0 | 2-3 | MT5 | 16-20 | 5-2.3 |
| 216<3K | Glu Asp Tyr Phe(sul) | 14-20 | 2.4-3.9 | 2 | INS4 MT4 HEP4 | 14-17 | 3.9-2.8 |
| 125 | pGlu Val Tyr | 13-20 | 2.7-3.6 | 1-2 | INS3 MT2 | 14-20 | 3.2-2.7 |
| 228-H2O | sul Val2 Gly2 pGlu | no spher | --- | --- | INS0 MT0 HEP0 | 9-13 | 5-3.4 |
| 228-AB | sul Val2 Gly2 pGlu | no spher | --- | --- | INS0 MT0 HEP0 | 16-18 | 3.8-3.3 |
| 177 | Glu Asp Arg | 14-19 | 5.2-3.9 | 2-3 | INS0 MT2 HEP0 | 14-19 | 5.2-3.9 |
| 118 | Glu Tyr | 12-14 | 5.2-6.0 | 1-2 | INS5 MT0 HEP0 | 12-19 | 6-4.2 |
| 153 | Glu LysFB Phe | no spher | --- | --- | | 8-9 | 9.1-10.2 |
| 131 | Glu2 Lys | no spher | --- | --- | INS1 MT0 | 14-17 | 4.3-3.6 |
| 162 | Glu2 Tyr Phe | 16-17 | 4.1-3.7 | 2-3 | INS3 MT0 HEP2 | 16-17 | 4.1-3.7 |
| 156 | Glu4 Lys2 Phe | no spher | --- | --- | INS0 | 20 | 4.5 |
| 124 | Glu Val Tyr | no spher | --- | --- | INS4 MT3 | 13-14 | 3.7-3.5 |
| 210>1K | Glu Asp Lys Val * | 12-20 | 3.6-3.1 | 1-2 | INS4 MT4 HEP3 | 12-19 | 3.6-3.2 |
| 156 | Glu4 Lys2 Phe | 14-17 | 3.6-3.1 | 2 | INS0 | 14 | 3.6 |
| 231 | Glu Lys Phe sul | no spher | --- | --- | INS2 MT0 HEP3 | 18 | 9.1 |
| 232 | Glu Leu Lys | no spher | --- | --- | INS0 MT0 HEP2 | 6 | 10.9 |
| 233 | Glu Leu Arg | no spher | --- | --- | INS0 MT0 HEP2 | 9 | 10 |
| blank | 2% ampholytes | --- | --- | --- | --- | --- | --- |
| 216<3k | Glu Asp sul Tyr Phe | 14-20 | 4.1-2.6 | 2 | INS4 MT4 HEP4 | 18-20 | 3-2.6 |
| 230>1k | Glu Tyr | 13-20 | 3.9-3 | 3 | INS4 MT4 HEP0 | 15-20 | 3.3-3 |
| 170a | Glu Asp LysFB | 15-20 | 3.9-2.2 | 2 | MT5 | 18-19 | 3.3-2.6 |
| 236-cp | Glu Tyr Lys-HCl | 19-20 | 3.0 | 0-1 | INS2 MT0 HEP0 | 19-20 | 3 |
| 216<3k | Glu Asp sul TyrPhe * | 14-20 | 3.3-2.2 | 2 | INS4 MT4 HEP4 | 20 | 2.2 |
| 216<3k | Glu Asp sul Tyr Phe | 16-20 | 3.9-2.3 | 1-2 | INS4 MT4 HEP4 | 20 | 2-3 |
| 237-cp | Glu2 Leu2 Lys2 Asp | no spher | --- | --- | INS0 MT0 HEP0 | 9-12 | 4.6-4 |
| 243-cs | pGluArg2Lys2LeuAsp | no spher | --- | --- | INS0 MT0 HEP0 | 15-17 | 8.5-7 |
| 246-cs | Glu2 LysH2 Phe2 Asp | 17-20 | 4.1-2.2 | 2-3 | INS4 MT4 HEP0 | 17-20 | 4.1-2.2 |
| 250-cs | pGluArg2LysH2LeuAsp2 | no spher | --- | --- | INS0 MT0 HEP0 | 11-14 | 8-6.8 |
| 249<3K | Glu2 Leu2 LysH2 pGlu | no spher | --- | --- | INS0 MT0 HEP0 | | |
| 254-cp | GluAspsulTyrPheOrn.5 | 18 | 5.4-2.5 | 2 | INS3 MT4 HEP4 | 14-20 | 3.7-2.1 |
| 253-cp | Glu Asp sul Tyr Phe | 18-20 | 3-4 | 2 | INS0 MT0 HEP0 | 1-4,19-20 | 11.5,3-3.5 |
| 235<3k | GluAspsulTyr10Phe10 | 18-20P | 2.6-3.2 | 1-2 | INS0 MT0 HEP0 | 1-3 | 11 |
| 256-cp | Glu2 LysH2 Phe2 pGlu | 13-20 | 3.7-4.0 | 1-2 | INS0 MT0 HEP0 | 2-5,14-20 | 2.7-4,7-10 |
| 238<3K | GluAspsulTyr5Phe5 | no spher | --- | --- | INS1 MT3 HEP4 | 2 | 11.4 |
| 255-CP | Glu AspTyrsulPheOrn | 13-20 | 5.3-3.1 | ? | INS1 MT3 HEP4 | 1-6,19-20 | 11-9.3,6-3 |
| 251<3K | Glu2Asp2sulTyr5Phe5 | 16-20 | 5.5-3.3 | 2 | INS4 MT4 HEP4 | 17-20 | 5.8-3.8 |

Appendix B
page 2 of 2

IEF TABLES
Proteinoid sorting, pKa and composition
Chemical basis for microsphere ODS

| Run No. | Material ID No. | Composition --->(*no_asp) | Sphere frac number | Sphere pH range | Sphere IEF rating | Sphere Matrix rating | Max UV Frac.No. | Max UV pH |
|---|---|---|---|---|---|---|---|---|
| 47 | 257-CP | Glu Asp ArgH OrnH | no spher | --- | --- | INS0 HT0 HEP0 | 19-20 | 5-3 |
| 48 | 257-CP | Glu Asp ArgH OrnH* | no spher | --- | --- | INS0 HT0 HEP0 | 15-17 | 8.9-8.5 |
| 49 | 258<3K | Glu Asp ArgH | no spher | --- | --- | INS0 HT0 HEP0 | 1,17-20 | 9.8,4-2.5 |
| 50 | 262-CP | Glu Orn Asp LysFB | 11-18 | 6.8-3.5 | 2 | INS0 HT1 HEP4 | 15 | 4.8 |
| 51 | 262-FILT | Glu Orn Asp LysFB | 4-11 | 7.7-5.4 | 1-2 | ins0 ht1 hep4 | 1-2,12-20 | 9.4.6-1.8 |
| 52 | 267-cp | Glu LysFB Asp LysFB | no spher | --- | --- | INSa HTc HEPc | 14-20 | 6.3-3.8 |
| 53 | 268-cp c | Glu Asp sul Tyr Phe | 15-20 | 4.5-2.34 | 2-3 | INS4oHT4oHEP4a | 1-10,18-20 | 12-2.5 |
| 54 | 269-cp | Glu OrnH Asp LysFB | 17-20 | 2.91-1.4 | 1 | INSc HTc HEPc | 4,7,9 | 9-7.5 |
| 55 | 273-cp | Glu Leu LysH Phe | 17-20 | 3-1.2 | 1-2 | INS2a HT2 HEP2a | 19 | 2 |
| 56 | 272/273 | Glu Leu LysH | no spher | --- | --- | --- | 3-9,13-15 | 9.8.5,8-8. |
| 57 | 276 | Glu Leu Arg Phe | 12-18 | 3.57-1.4 | 1-2,2 | INS2 HT2 HEP3 | 1-7,17-20 | 9-6,1.5-1. |
| 58 | 274 | Glu Leu Arg Tyr | no spher | --- | --- | INSc HTc Hepc | 16-20 | 4.14-1.4 |
| 59 | 272 | Glu Leu LysH Tyr | no spher | --- | --- | INSc HTc HEPc | 1-2 | 9.4-9.3 |
| 60 | 274A | Glu Leu Arg | no spher | --- | --- | --- | all frac. | --- |
| 61 | 278 | Glu Lys Phe sul | 16-20 | 4.8-3.5 | 1-2 | INSc HTc HEP4 | all frac. | --- |
| 62 | 284E | GluAspTyrPhesulOrn | 14-20 | 3.8-2.1 | 1-2 | INS4oHT4oHEP3 | 15-20 | 3.3-2.1 |
| 63 | 267-cp | Glu Phe | 10-20 | 3.55-2.3 | 2 | INS3 HT2 HEP3 | 18-20,1-7 | 2.4-2.3,8 |
| 64 | 284-E | Glu2Asp2Tyr2Phe2Orn | 14-20 | 3.95-1.6 | 2 w/oil | INS4a HT4aHEP2a | 3-8 | 12.3-7.76 |
| 65 | 288-cp | Glu Orn Phe | no spher | --- | --- | INSc HTc HEPc | 17-20 | 2.7-1.02 |
| 66 | 293-cp | Glu Asp sul Tyr Phe | 1-8 | 1.9-3.9 | 1-2 | INS1 HT2 HEP1a | | |
| 67 | 290-cp | Glu Arg Phe | 1-7 | 1.05-3.8 | 1-2 | INS1 HT1 HEP1 | 18-20 | 12.1-12.6 |
| 68 | 292-cp | Glu Asp Arg | no spher | --- | --- | INS HT HEP | 16-20 | 3.19-1.5 |
| 69 | 300-cp | Glu Orn Asp Lys Phe | 15-19 | 4.05-1.5 | 1-2 | INS3 HT3 HEP3? | all frac. | --- |
| 70 | 297-cp | GLU ASP SUL TYR PHE | 1-7 | 2.38-4.15 | 2-3 | INS2 HT4 HEP | 1-2 | 2.38-2 |
| 71 | 301<3K | GLU ASP SUL TYR PHE | --- | --- | --- | INS4 HT2 HEP3 | 1-20 | --- |
| 72 | 303 | GLU ASP SUL TYR PHE | 1-8 | 2.83-3.76 | 2-3 | INS4 HT2 HEP3a | 1-3,18-20 | 2.88/1 |
| 73 | 299 | GLU2 LYS2 PHE2 ASP | 1-7 | 1.13-3.82 | 1 | INS4a HT4 HEP2a | 3-7 | 1.58-3 |
| 74 | 305 | PGLU ASP.5 TYR PHE | 1-12 | 2.12-4.20 | 2-3 | INS3 HT2 HEP3 | 11-20 | 5.54-1 |
| 75 | 307-CP | GLN ASP TYR PHE | 1-9 | 2.43-4.48 | 2-3 | INS4o HT4 HEP4a | 1-13 | 2.43-7.0 |
| 76 | 305 | PGLU ASP.5 TYR PHE | 1-6 | 2.05-5.56 | 2-3 | INS3 HT2 HEP3 | 4-7 | 3.3-7.0 |
| 77 | 124/156 | GLU TYR VAL/GLU2 LYS2 PHE | --- | --- | --- | I4 M3 H3/IOHOHO | 1 | 10.58 |
| 78 | 223-CP | LYS ARG LEU PGLU | | | | INS0 HT0 HEP2 | | |
| 79 | 319-CP | SUL-U TYR PHE ASP PGLU | 1-10 | 2.28-5.3 | 2-3o | INS4aHT4hEP4a | 2-8,19-20 | 2.3-4,12 |
| 80 | 314-CP | SUL TYR PHE ASP PGLU | 1-11 | 1.93-5.30 | 2 | INS2aHT4aHEP4a | 18 | 8.95 |
| 81 | 320-CP | SUL TYR PHE PGLU ASP | 1-7 | 2.12-4.4 | 2a | INS4aHT4HEP4 | 16-20 | 9.3-10.25 |
| 82 | 188>6K | ASP2 TYR PHE | 1-6 | 1.85-5 | 0a | INSOHTOHEP0 | 18-20 | 12-12.5 |
| 83 | 286-CP | GLU ASP | 14-18 | 2.38-2.02 | PARTICLES | INSCHTCHEPC | 14-18 | 2.38 |
| 84 | 288/188 | ASP2 TYR PHE/GLU ORN PHE | 14-17 | 4.9-3.1 | 1-2 | INSCHTCHEPC | 17-19 | 3.1-1.65 |
| 85 | 66 | GLU2 GLY | ---- | ---- | ---- | HT0 | 16-19 | 2.85-2.55 |
| 86 | 0112-2A | GLU ASP TYR PHE | 1-10 | 3.17-13.48 | 1,0-1 | INS5aHT3aHEP3a | 14,2 | 9.20,3.32 |

Sphere Testing of Externally Prepared Proteinoids   Appendix C
Page 1 of 3

| SOI No. | Composition | pH | 0.85 CA | 5% AA | 0.85 CA +GM | 5% AA +GM | INS/CA GM/GL/CD | INS/AA GM/GL/CD | EEP/CA + GM |
|---|---|---|---|---|---|---|---|---|---|
| 91EHIP001F20B1SA0° GLU ASP TYR PHE | Rating Desc. pH | ---- | 1-2 a ---- | 1-2 a ---- | 3 ---- ---- | 2-3 a ---- | 2-3 a ---- | 0 a ---- | 2-3 a ---- |
| 91EHIP001F21B1SA07 GLU ASP TYR PHE | Rating Desc. pH | ---- | 2-3 a,ag ---- | 2-3 a,ag ---- | 3-4 a ---- | 3-4 a ---- | 2-3 a,p ---- | 4 a,ag ---- | 4-5 a,p ---- |
| 91EHIP001F21B1SA07 GLU ASP TYR PHE | Rating Desc. pH | ---- | 3 ag,a ---- | 3 a ---- | 4-5 a ---- | 3 ag,p ---- | 3-4 ag,p ---- | 3-4 ag,p ---- | 4-5 a,p ---- |
| 91EHIP001F22B1SA7 GLU ASP TYR PHE | Rating Desc. pH | ---- | 2-3 ---- ---- | 2-3 a ---- | 3 ---- ---- | 4-5 a,o ---- | 0 a ---- | 3-4 o ---- | 4-5 a ---- |
| 91EHIP011F23B1SA8 GLU ASP TYR PHE ORN | Rating Desc. pH | ---- | 2-3 a,p ---- | 3 a ---- | 4 ---- ---- | 4 ---- ---- | 0-1 a ---- | 4 a,o ---- | 3-4 a,o ---- |
| 91EHIP011F24SA7 GLU ASP TYR PHE ORN | Rating Desc. pH | ---- | 2 a ---- | 2 a ---- | 2-3 o ---- | 3 ---- ---- | 4 a ---- | 0-1 a,o ---- | 5 p ---- |
| 91EHIP001F25B1SA21 GLU ASP TYR PHE | Rating Desc. pH | ---- | 0-1 ---- ---- | 0 a,p ---- | 3-4 a ---- | 0 ---- ---- | 3-4 a ---- | 4-5 a ---- | 4-5 a ---- |
| 91EHIP001F25B1SA5 GLU ASP TYR PHE | Rating Desc. pH | ---- | 0-1 a ---- | 1 a ---- | 2-3 a ---- | 2-3 ---- ---- | 0-1 a ---- | 3-4 a,o ---- | 2-3 a ---- |
| 91EHIP001F26B1SA2A GLU ASP TYR PHE | Rating Desc. pH | ---- | 2-3 ---- ---- | 2-3 a ---- | 3 ---- ---- | 3-4 ---- ---- | 2 a ---- | 2-3 ---- ---- | 3-4 o ---- |

CA= citric acid     INS= insulin
GM= gum acacia     HEP = heparin
GL= gelatin         CD = cyclodextrin
a = amorphous       o = oil
p = particulate     ag = aggregate rating: 0 worst   5=best Sphere Testing of Externally Prepared Proteinoids Appendix C
page 2 of 3

| SOI No. | Composition | pH | 0.85 CA | 5% AA | 0.85 CA +GH | 5% AA +GH | INS/CA GH/GL/CD | INS/AA GH/GL/CD | EEP/CA + GH |
|---|---|---|---|---|---|---|---|---|---|
| 91CTAP001F014B02 | GLU ASP TYR PHE | ---- | Rating 2-3 | 3 | 5 | 4-5 | 4-5 | 2-3 | 3 |
| | | | Desc. a | a | a | ---- | a | a | a |
| | | | pH ---- | ---- | ---- | ---- | ---- | ---- | ---- |
| 91CTAP001F014B02 | GLU ASP TYR PHE | ---- | Rating 2 | 4-5 | 5 | 5 | 5 | 5 | 5 |
| | | | Desc. ---- | a | ---- | ---- | ---- | ---- | ---- |
| | | | pH ---- | ---- | ---- | ---- | ---- | ---- | ---- |
| 91CTAP001F014B02 | GLU ASP TYR PHE | ---- | Rating 2-3 | 3 | 5 | 4-5 | 4-5 | 2-3 | 3 |
| | | | Desc. a | a | a | ---- | a | a | a |
| | | | pH ---- | ---- | ---- | ---- | ---- | ---- | ---- |
| 91CTAP001F014B03 | GLU ASP TYR PHE | ---- | Rating 2 | 2 | 3-4 | 3-4 | 5 | 3 | 3-4 |
| | | | Desc. a | a | a | a | a | a | a |
| | | | pH ---- | ---- | ---- | ---- | ---- | ---- | ---- |
| 91CTAP001F014B03 | GLU ASP TYR PHE | ---- | Rating 0-1 | 0-1 | 5 | 5 | 5 | 2-3 | 4 |
| | | | Desc. a,ag | a,ag | a,ag | a,ag | a,ag | a | ---- |
| | | | pH ---- | ---- | ---- | ---- | ---- | ---- | ---- |
| 91CTAP001F014B03 | GLU ASP TYR PHE | ---- | Rating 2-3 | 2-3 | 5 | 5 | 5 | 3 | 5 |
| | | | Desc. ag | ag | a,ag | ---- | a,ag,o | ag,a | ---- |
| | | | pH ---- | ---- | ---- | ---- | ---- | ---- | ---- |
| 91CTAP001F014B03 | GLU ASP TYR PHE | ---- | Rating 2 | 2 | 3-4 | 3-4 | 5 | 3 | 3-4 |
| | | | Desc. a | a | a | a | a | a | a |
| | | | pH ---- | ---- | ---- | ---- | ---- | ---- | ---- |
| 91CTAP001F014B04 | GLU ASP TYR PHE | ---- | Rating 0-1 | 0-1 | 4 | 5 | 2-3 | 0 | 5 |
| | | | Desc. a | a | a | a | a | a | a |
| | | | pH ---- | ---- | ---- | ---- | ---- | ---- | ---- |
| 91CTAP001F014B05 | GLU ASP TYR PHE | ---- | Rating 3 | 3-4 | 5 | 4-5 | 4 | 4 | 4 |
| | | | Desc. ---- | a | a | ---- | a | a | a |
| | | | pH ---- | ---- | ---- | ---- | ---- | ---- | ---- |
| 91CTAP001F014B04 | GLU ASP TYR PHE | ---- | Rating 3 | 3-4 | 5 | 4-5 | 4 | 4 | 4 |
| | | | Desc. ---- | a | a | ---- | a | a | a |
| | | | pH ---- | ---- | ---- | ---- | ---- | ---- | ---- |
| 91EMIP011F15B1 | GLU2ASP2TYR2PHE2ORN | ---- | Rating 2-3 | 3 | 4 | 3-4 | 0 | 3-4 | 4 |
| | | | Desc. a,ag | ag | ---- | a,o | a | ---- | ---- |
| | | | pH ---- | ---- | ---- | ---- | ---- | ---- | ---- |
| 91EMIP001F20B1SA07 | GLU ASP TYR PHE | ---- | Rating 2 | 2-3 | 3 | 2-3 | 4 | 3 | 4 |
| | | | Desc. ag | ag | ---- | ---- | a,o | a,o | ---- |
| | | | pH ---- | ---- | ---- | ---- | ---- | ---- | ---- |

Sphere Testing of Externally Prepared Proteinoids

Appendix C
page 3 of 3

| SOI No. | Compostion | pH | 0.85 CA | 5% AA | 0.85 CA +GH | 5% AA +GH | INS/CA GH/GL/CD | INS/AA GH/GL/CD | EEP/CA + GH |
|---|---|---|---|---|---|---|---|---|---|
| | | | Rating Desc. pH | | | | | | |
| 91EM1P00IF25B1SA3a | | 6.52 | Rating 2-3 Desc. aq,a pH ---- | 2-3 aq ---- | 3-4 ---- ---- | 4 ---- ---- | 3-4 a,p ---- | 4 o ---- | 5 ---- ---- |
| 91CTAP001F012B01 | GLU ASP TYR PHE | 7.5 | Rating 2-3 Desc. a pH ---- | 2 a ---- | 5 ---- ---- | 5 ---- ---- | 4 a ---- | 5 ---- ---- | 5 a ---- |
| F005-B01 | GLU2 LYSE2 PHE2 ASP | 9.0 | Rating ---- Desc. ---- pH ---- | ---- ---- ---- | 3-4 a,o ---- | ---- ---- ---- | 4 a,o ---- | 3 a,o ---- | 3 a,o ---- |
| 91CTAPR001F010B01 | GLU2 LYSE2 PHE2 ASP | ---- | Rating 2-3 Desc. a pH ---- | 2 a ---- | 4 ---- ---- | 4 ---- ---- | 4 a ---- | 4 a ---- | 4 a ---- |
| F003-B01 | GLU2 LYSE2 PHE2 ASP | ---- | Rating ---- Desc. ---- pH ---- | ---- ---- ---- | 4 a ---- | 3-4 o ---- | 3 a ---- | 4-5 a ---- | 3 a,o ---- |
| F004-B01 | GLU2 LYSE2 PHE2 ASP | ---- | Rating ---- Desc. ---- pH ---- | ---- ---- ---- | 3-4 a,o ---- | 2-3 a ---- | 2-3 a ---- | 4 a ---- | 2-3 a ---- |
| 91CTAP001F011B01 | GLU ASP TYR PHE ORN | ---- | Rating ---- Desc. ---- pH ---- | ---- ---- ---- | ---- ---- ---- | ---- ---- ---- | ---- ---- ---- | ---- ---- ---- | ---- ---- ---- |
| 91CTAP001F013B01 | GLU ASP TYR PHE | 7.9 | Rating 2-3 Desc. ---- pH ---- | 2-3 a ---- | 4-5 ---- ---- | 4-5 a,o ---- | 4-5 a,o ---- | 4 a,o ---- | 5 a ---- |
| 91CTAP001F014B01 | GLU ASP TYR PHE | 8.0 | Rating 0 Desc. a pH ---- | 0-1 a ---- | 4-5 a ---- | 4-5 ---- ---- | 4-5 a ---- | 3-4 a ---- | 4 a ---- |
| 91CTAP001F014B01 | GLU ASP TYR PHE | ---- | Rating 0-1 Desc. a pH ---- | 0-1 a ---- | 5 a,o ---- | 4 a,o ---- | 4 a,o ---- | 3 a,o ---- | 3-4 a,o ---- |
| 91CTAP001F014B01 | GLU ASP TYR PHE | ---- | Rating 2 Desc. aq pH ---- | 2 aq,a ---- | 5 aq ---- | 5 ---- ---- | 5 aq,a ---- | 3 aq,a ---- | 5 ---- ---- |

What is claimed is:

1. A method for delivering a biologically active agent to a mammal in need of said agent, said method comprising orally administering a composition comprising:
   (A) a biologically active agent encapsulated,
   (B) within a microsphere carrier, said carrier comprising a proteinoid comprising
      (i) at least one monomer selected from the group consisting of tyrosine and phenylalanine;
      (ii) at least one monomer selected from the group consisting of glutamic acid, pyroglutamic acid, glutamine, and aspartic acid; and
      (iii) optionally at least one monomer selected from the group consisting of lysine, arginine, and ornithine, and
   (C) a physiologically compatible excipient said proteinoid being soluble within a selected pH range.

2. A method as defined in claim 1, wherein said proteinoid forms a wall and said biologically active agent is encapsulated within said wall.

3. A method as defined in claim 1, wherein said proteinoid is an acid-soluble proteinoid.

4. A method as defined in claim 3, wherein the monoclonal antibody in murine IgG.

5. A method as defined in claim 1, wherein said proteinoid is a base-soluble proteinoid.

6. A method as defined in claim 1, wherein said biologically active agent is a monoclonal antibody.

7. A method as defined in claim 1, wherein said biologically active agent comprises at least one protein.

8. A method as defined in claim 7, wherein said protein comprises erythropoietin.

9. A method as defined in claim 8, wherein said protein comprises human growth factor.

10. A method as defined in claim 8, wherein said protein comprises bovine growth factor.

11. A method as defined in claim 7, wherein said protein comprises alpha interferon.

12. A method as defined in claim 7, wherein said protein comprises calcitonin.

13. A method as defined in claim 7, wherein said protein comprises insulin.

14. A method as defined in claim 7, wherein said protein comprises atrial natriuretic factor.

15. A method as defined in claim 7, wherein said protein comprises interleukin II.

16. A method as defined in claim 7, wherein said protein comprises M-protein.

17. A method as defined in claim 1, wherein said biologically active agent comprises at least one polysaccharide.

18. A method as defined in claim 7, wherein said polysaccharide comprises heparin.

19. A method as defined in claim 1, wherein said biologically active agent comprises an antigen.

20. A method as defined in claim 1, wherein said biologically active agent comprises aspirin.

21. A method as defined in claim 1, wherein said biologically active agent comprises a quinolone.

22. A method as defined in claim 1, wherein said biologically active agent comprises an antimicrobial agent.

* * * * *